United States Patent
Swamy

(10) Patent No.: US 9,336,302 B1
(45) Date of Patent: May 10, 2016

(54) INSIGHT AND ALGORITHMIC CLUSTERING FOR AUTOMATED SYNTHESIS

(71) Applicant: Zuci Realty LLC, Lexington, MA (US)

(72) Inventor: Gitanjali Swamy, Lexington, NY (US)

(73) Assignee: ZUCI REALTY LLC, Lexington, MA (US)

( * ) Notice: Subject to any disclaimer, the term of this patent is extended or adjusted under 35 U.S.C. 154(b) by 363 days.

(21) Appl. No.: 13/826,338

(22) Filed: Mar. 14, 2013

Related U.S. Application Data

(60) Provisional application No. 61/673,914, filed on Jul. 20, 2012.

(51) Int. Cl.
   *G06F 17/30* (2006.01)

(52) U.S. Cl.
   CPC ...... *G06F 17/3071* (2013.01); *G06F 17/30306* (2013.01); *G06F 17/30648* (2013.01)

(58) Field of Classification Search
   None
   See application file for complete search history.

(56) References Cited

U.S. PATENT DOCUMENTS

| | | |
|---|---|---|
| 4,081,607 A | 3/1978 | Vitols et al. |
| 4,257,703 A | 3/1981 | Goodrich |
| 4,773,093 A | 9/1988 | Higgins et al. |
| 4,855,923 A | 8/1989 | Fullmer |
| 4,965,580 A | 10/1990 | Tasaki et al. |
| 5,020,411 A | 6/1991 | Rowan |
| 5,253,307 A | 10/1993 | Wayner et al. |
| 5,285,291 A | 2/1994 | Schiller |
| 5,327,521 A | 7/1994 | Savic et al. |
| 5,442,792 A | 8/1995 | Chun |
| 5,448,684 A | 9/1995 | Holt |
| 5,463,702 A | 10/1995 | Trueblood |
| 5,497,486 A | 3/1996 | Stolfo et al. |
| 5,506,801 A | 4/1996 | Tawel |
| 5,566,078 A | 10/1996 | Ding et al. |
| 5,574,837 A | 11/1996 | Clark et al. |
| 5,625,704 A | 4/1997 | Prasad |
| 5,627,040 A | 5/1997 | Bierre et al. |
| 5,668,897 A | 9/1997 | Stolfo |
| 5,699,507 A | 12/1997 | Goodnow, II et al. |
| 5,710,916 A | 1/1998 | Barbara et al. |
| 5,717,915 A | 2/1998 | Stolfo et al. |
| 5,724,571 A | 3/1998 | Woods |
| 5,731,989 A | 3/1998 | Tenny et al. |
| 5,748,780 A | 5/1998 | Stolfo |

(Continued)

FOREIGN PATENT DOCUMENTS

WO    WO 01/50347    *   7/2001    ............ G06F 17/30

*Primary Examiner* — Son T Hoang
(74) *Attorney, Agent, or Firm* — Steven M. Hoffberg, Esq.; Ostrolenk Faber LLP

(57) ABSTRACT

A decision support system and method, which receives user inputs comprising: at least one user criterion, and at least one user input tuning parameter representing user tradeoff preferences for producing an output; and selectively produces an output of tagged data from a clustered database in dependence on the at least one user criterion, the at least one user input tuning parameter, and a distance function; receives at least one reference-user input parameter representing the at least one reference-user's analysis of the tagged data and the corresponding user inputs, to adapt the distance function in accordance with the reference-user inputs as a feedback signal; and clusters the database in dependence on at least the distance function, wherein the reference-user acts to optimize the distance function based on the user inputs and the output, and on at least one reference-user inference.

27 Claims, 5 Drawing Sheets

(56) References Cited

U.S. PATENT DOCUMENTS

| | | |
|---|---|---|
| 5,764,283 A | 6/1998 | Pingali et al. |
| 5,795,727 A | 8/1998 | Bierre et al. |
| 5,809,490 A | 9/1998 | Guiver et al. |
| 5,813,002 A | 9/1998 | Agrawal et al. |
| 5,872,850 A | 2/1999 | Klein et al. |
| 5,889,523 A | 3/1999 | Wilcox et al. |
| 5,920,852 A | 7/1999 | Graupe |
| 5,926,820 A | 7/1999 | Agrawal et al. |
| 5,940,529 A | 8/1999 | Buckley |
| 5,940,833 A | 8/1999 | Benson |
| 5,949,367 A | 9/1999 | Trompf et al. |
| 6,041,311 A | 3/2000 | Chislenko et al. |
| 6,049,777 A | 4/2000 | Sheena et al. |
| 6,085,151 A | 7/2000 | Farmer et al. |
| 6,092,049 A | 7/2000 | Chislenko et al. |
| 6,100,825 A | 8/2000 | Sedluk et al. |
| 6,112,186 A | 8/2000 | Bergh et al. |
| 6,121,969 A | 9/2000 | Jain et al. |
| 6,122,628 A | 9/2000 | Castelli et al. |
| 6,140,643 A | 10/2000 | Brown et al. |
| 6,185,314 B1 | 2/2001 | Crabtree et al. |
| 6,192,364 B1 | 2/2001 | Baclawski |
| 6,203,987 B1 | 3/2001 | Friend et al. |
| 6,249,241 B1 | 6/2001 | Jordan et al. |
| 6,263,088 B1 | 7/2001 | Crabtree et al. |
| 6,263,334 B1 | 7/2001 | Fayyad et al. |
| 6,282,538 B1 | 8/2001 | Woods |
| 6,295,367 B1 | 9/2001 | Crabtree et al. |
| 6,295,504 B1 | 9/2001 | Ye et al. |
| 6,295,514 B1 | 9/2001 | Agrafiotis et al. |
| 6,300,965 B1 | 10/2001 | Sowizral et al. |
| 6,331,859 B1 | 12/2001 | Crinon |
| 6,351,712 B1 | 2/2002 | Stoughton et al. |
| 6,373,485 B2 | 4/2002 | Sowizral et al. |
| 6,389,169 B1 | 5/2002 | Stark et al. |
| 6,400,831 B2 | 6/2002 | Lee et al. |
| 6,411,953 B1 | 6/2002 | Ganapathy et al. |
| 6,415,046 B1 | 7/2002 | Kerut, Sr. |
| 6,421,612 B1 | 7/2002 | Agrafiotis et al. |
| 6,424,971 B1 | 7/2002 | Kreulen et al. |
| 6,424,973 B1 | 7/2002 | Baclawski |
| 6,437,796 B2 | 8/2002 | Sowizral et al. |
| 6,445,391 B1 | 9/2002 | Sowizral et al. |
| 6,453,246 B1 | 9/2002 | Agrafiotis et al. |
| 6,463,433 B1 | 10/2002 | Baclawski |
| 6,466,695 B1 | 10/2002 | Potzsch et al. |
| 6,468,476 B1 | 10/2002 | Friend et al. |
| 6,470,094 B1 | 10/2002 | Lienhart et al. |
| 6,473,522 B1 | 10/2002 | Lienhart et al. |
| 6,484,168 B1 | 11/2002 | Pennock et al. |
| 6,487,554 B2 | 11/2002 | Ganapathy et al. |
| 6,496,834 B1 | 12/2002 | Cereghini et al. |
| 6,505,191 B1 | 1/2003 | Baclawski |
| 6,519,591 B1 | 2/2003 | Cereghini et al. |
| 6,526,389 B1 | 2/2003 | Murad et al. |
| 6,535,881 B1 | 3/2003 | Baclawski |
| 6,539,352 B1 | 3/2003 | Sharma et al. |
| 6,556,983 B1 | 4/2003 | Altschuler et al. |
| 6,564,197 B2 | 5/2003 | Sahami et al. |
| 6,584,220 B2 | 6/2003 | Lantrip et al. |
| 6,584,433 B1 | 6/2003 | Zhang et al. |
| 6,592,627 B1 | 7/2003 | Agrawal et al. |
| 6,594,658 B2 | 7/2003 | Woods |
| 6,615,205 B1 | 9/2003 | Cereghini et al. |
| 6,627,464 B2 | 9/2003 | Coumou |
| 6,636,849 B1 | 10/2003 | Tang et al. |
| 6,643,629 B2 | 11/2003 | Ramaswamy et al. |
| 6,674,905 B1 | 1/2004 | Matsugu et al. |
| 6,684,177 B2 | 1/2004 | Mishra et al. |
| 6,700,115 B2 | 3/2004 | Mickael |
| 6,701,026 B1 | 3/2004 | Zheng et al. |
| 6,711,585 B1 | 3/2004 | Copperman et al. |
| 6,732,119 B2 | 5/2004 | Ganapathy et al. |
| 6,735,336 B2 | 5/2004 | Avni et al. |
| 6,735,465 B2 | 5/2004 | Panescu |
| 6,750,859 B2 | 6/2004 | Sowizral et al. |
| 6,751,363 B1 | 6/2004 | Natsev et al. |
| 6,751,614 B1 | 6/2004 | Rao |
| 6,757,415 B1 | 6/2004 | Rogers et al. |
| 6,760,701 B2 | 7/2004 | Sharma et al. |
| 6,763,128 B1 | 7/2004 | Rogers et al. |
| 6,772,170 B2 | 8/2004 | Pennock et al. |
| 6,778,699 B1 | 8/2004 | Gallagher |
| 6,778,981 B2 | 8/2004 | Lee et al. |
| 6,785,409 B1 | 8/2004 | Suri |
| 6,785,419 B1 | 8/2004 | Jojic et al. |
| 6,797,526 B2 | 9/2004 | Tanaka et al. |
| 6,799,175 B2 | 9/2004 | Aggarwal |
| 6,801,645 B1 | 10/2004 | Collins et al. |
| 6,801,859 B1 | 10/2004 | Friend et al. |
| 6,804,670 B2 | 10/2004 | Kreulen et al. |
| 6,807,306 B1 | 10/2004 | Girgensohn et al. |
| 6,816,848 B1 | 11/2004 | Hildreth et al. |
| 6,819,793 B1 | 11/2004 | Reshetov et al. |
| 6,826,316 B2 | 11/2004 | Luo et al. |
| 6,832,162 B2 | 12/2004 | Floudas et al. |
| 6,834,266 B2 | 12/2004 | Kumar et al. |
| 6,834,278 B2 | 12/2004 | Yu et al. |
| 6,841,403 B2 | 1/2005 | Tanaka et al. |
| 6,845,377 B2 | 1/2005 | Yamane et al. |
| 6,854,096 B2 | 2/2005 | Eaton et al. |
| 6,895,267 B2 | 5/2005 | Panescu et al. |
| 6,904,420 B2 | 6/2005 | Shetty et al. |
| 6,906,719 B2 | 6/2005 | Chadha et al. |
| 6,907,380 B2 | 6/2005 | Mishra et al. |
| 6,912,547 B2 | 6/2005 | Chaudhuri et al. |
| 6,915,241 B2 | 7/2005 | Kohlmorgen et al. |
| 6,950,752 B1 | 9/2005 | Friend et al. |
| 6,954,756 B2 | 10/2005 | Arning et al. |
| 6,961,721 B2 | 11/2005 | Chaudhuri et al. |
| 6,968,342 B2 | 11/2005 | Wolman et al. |
| 6,970,796 B2 | 11/2005 | Tashev |
| 6,976,016 B2 | 12/2005 | Chang et al. |
| 6,980,984 B1 | 12/2005 | Huffman et al. |
| 6,993,186 B1 | 1/2006 | Glickman et al. |
| 6,999,886 B2 | 2/2006 | Hilliard |
| 7,010,520 B2 | 3/2006 | Agrawal et al. |
| 7,016,531 B1 | 3/2006 | Murching et al. |
| 7,031,844 B2 | 4/2006 | Bozinov et al. |
| 7,031,980 B2 | 4/2006 | Logan et al. |
| 7,035,431 B2 | 4/2006 | Blake et al. |
| 7,035,823 B2 | 4/2006 | Murad et al. |
| 7,039,446 B2 | 5/2006 | Ruchti et al. |
| 7,039,621 B2 | 5/2006 | Agrafiotis et al. |
| 7,043,463 B2 | 5/2006 | Bonabeau et al. |
| 7,047,252 B2 | 5/2006 | Buch et al. |
| 7,054,724 B2 | 5/2006 | Koshizen et al. |
| 7,058,638 B2 | 6/2006 | Singh |
| 7,058,650 B2 | 6/2006 | Yang et al. |
| 7,062,083 B2 | 6/2006 | Lim et al. |
| 7,065,521 B2 | 6/2006 | Li et al. |
| 7,065,587 B2 | 6/2006 | Huitema et al. |
| 7,068,723 B2 | 6/2006 | Foote et al. |
| 7,111,188 B2 | 9/2006 | Mukherjee |
| 7,113,958 B1 | 9/2006 | Lantrip et al. |
| 7,139,739 B2 | 11/2006 | Agrafiotis et al. |
| 7,142,602 B2 | 11/2006 | Porikli et al. |
| 7,158,970 B2 | 1/2007 | Chang et al. |
| 7,167,578 B2 | 1/2007 | Blake et al. |
| 7,174,048 B2 | 2/2007 | Glickman et al. |
| 7,177,470 B2 | 2/2007 | Jasinschi et al. |
| 7,188,055 B2 | 3/2007 | Agrafiotis et al. |
| 7,196,705 B2 | 3/2007 | Gallivan |
| 7,202,791 B2 | 4/2007 | Trajkovic |
| 7,206,778 B2 | 4/2007 | Bode et al. |
| 7,215,786 B2 | 5/2007 | Nakadai et al. |
| 7,216,129 B2 | 5/2007 | Aono et al. |
| 7,221,794 B1 | 5/2007 | Gloudemans, II et al. |
| 7,222,126 B2 | 5/2007 | Wolman |
| 7,225,397 B2 | 5/2007 | Fukuda et al. |
| 7,231,074 B2 | 6/2007 | Raunig |
| 7,246,012 B2 | 7/2007 | Kutsyy et al. |
| 7,246,128 B2 | 7/2007 | Jordahl |
| 7,251,648 B2 | 7/2007 | Chaudhuri et al. |

(56) References Cited

U.S. PATENT DOCUMENTS

| | | | |
|---|---|---|---|
| 7,263,220 B2 | 8/2007 | Crandall et al. |
| 7,272,262 B2 | 9/2007 | Glickman et al. |
| 7,275,018 B2 | 9/2007 | Abu-El-Zeet et al. |
| 7,287,019 B2 | 10/2007 | Kapoor et al. |
| 7,293,036 B2 | 11/2007 | Chaudhuri et al. |
| 7,296,011 B2 | 11/2007 | Chaudhuri et al. |
| 7,296,088 B1 | 11/2007 | Padmanabhan et al. |
| 7,325,201 B2 | 1/2008 | Ferrari et al. |
| 7,328,363 B2 | 2/2008 | Mukherjee |
| 7,337,158 B2 | 2/2008 | Fratkina et al. |
| 7,346,601 B2 | 3/2008 | Chaudhuri et al. |
| 7,369,680 B2 | 5/2008 | Trajkovic et al. |
| 7,369,889 B2 | 5/2008 | Astrom et al. |
| 7,369,961 B2 | 5/2008 | Castelli et al. |
| 7,376,752 B1 | 5/2008 | Chudnovsky et al. |
| 7,386,426 B1 | 6/2008 | Black et al. |
| 7,389,281 B2 | 6/2008 | Strobel Stewart et al. |
| 7,395,250 B1 | 7/2008 | Aggarwal et al. |
| 7,397,946 B2 | 7/2008 | Reshetov et al. |
| 7,401,087 B2 | 7/2008 | Copperman et al. |
| 7,406,200 B1 | 7/2008 | Syeda-Mahmood et al. |
| 7,418,136 B2 | 8/2008 | Goldfoot |
| 7,424,462 B2 | 9/2008 | Avni et al. |
| 7,426,301 B2 | 9/2008 | Porikli |
| 7,428,528 B1 | 9/2008 | Ferrari et al. |
| 7,428,541 B2 | 9/2008 | Houle |
| 7,437,308 B2 | 10/2008 | Kumar et al. |
| 7,450,122 B2 | 11/2008 | Petrovic et al. |
| 7,450,746 B2 | 11/2008 | Yang et al. |
| 7,458,050 B1 | 11/2008 | Arbel et al. |
| 7,464,074 B2 | 12/2008 | Sebbane |
| 7,468,730 B2 | 12/2008 | Petrovic et al. |
| 7,475,085 B2 | 1/2009 | Aggarwal et al. |
| 7,487,056 B2 | 2/2009 | Tashev |
| 7,492,943 B2 | 2/2009 | Li et al. |
| 7,499,916 B2 | 3/2009 | Liu et al. |
| 7,512,524 B2 | 3/2009 | Be'er et al. |
| 7,516,149 B2 | 4/2009 | Motwani et al. |
| 7,519,209 B2 | 4/2009 | Dawant et al. |
| 7,519,227 B1 | 4/2009 | Syeda-Mahmood et al. |
| 7,526,101 B2 | 4/2009 | Avidan |
| 7,529,732 B2 | 5/2009 | Liu et al. |
| 7,539,656 B2 | 5/2009 | Fratkina et al. |
| 7,545,978 B2 | 6/2009 | Amini et al. |
| 7,552,131 B2 | 6/2009 | Chron et al. |
| 7,552,474 B2 | 6/2009 | Gurda et al. |
| 7,555,441 B2 | 6/2009 | Crow et al. |
| 7,558,425 B1 | 7/2009 | Syeda-Mahmood et al. |
| 7,562,015 B2 | 7/2009 | Baker |
| 7,562,325 B1 | 7/2009 | Arbel et al. |
| 7,565,213 B2 | 7/2009 | Dittmar et al. |
| 7,565,251 B2 | 7/2009 | Stoughton et al. |
| 7,565,346 B2 | 7/2009 | Fan et al. |
| 7,565,432 B2 | 7/2009 | Huitema et al. |
| 7,567,961 B2 | 7/2009 | Yang-Stephens et al. |
| 7,570,213 B2 | 8/2009 | Debany et al. |
| 7,574,069 B2 | 8/2009 | Setlur et al. |
| 7,574,409 B2 | 8/2009 | Patinkin |
| 7,580,556 B2 | 8/2009 | Lee et al. |
| 7,580,682 B2 | 8/2009 | Lal et al. |
| 7,584,168 B2 | 9/2009 | Meyer |
| 7,590,264 B2 | 9/2009 | Mattes et al. |
| 7,599,799 B2 | 10/2009 | Friend et al. |
| 7,599,917 B2 | 10/2009 | Meyerzon et al. |
| 7,603,326 B2 | 10/2009 | Bonabeau et al. |
| 7,610,306 B2 | 10/2009 | Lin et al. |
| 7,613,572 B2 | 11/2009 | Ben-Gal et al. |
| 7,624,337 B2 | 11/2009 | Sull et al. |
| 7,639,714 B2 | 12/2009 | Stolfo et al. |
| 7,639,868 B1 | 12/2009 | Regli et al. |
| 7,643,597 B2 | 1/2010 | Liu et al. |
| 7,644,090 B2 | 1/2010 | Nakano et al. |
| 7,650,320 B2 | 1/2010 | Nakano |
| 7,657,100 B2 | 2/2010 | Gokturk et al. |
| 7,657,126 B2 | 2/2010 | Gokturk et al. |
| 7,657,379 B2 | 2/2010 | Stoughton et al. |
| 7,660,468 B2 | 2/2010 | Gokturk et al. |
| 7,679,617 B2 | 3/2010 | Kolmykov-Zotov et al. |
| 7,684,963 B2 | 3/2010 | Aggarwal |
| 7,685,090 B2 | 3/2010 | Chaudhuri et al. |
| 7,688,495 B2 | 3/2010 | Tonar et al. |
| 7,689,457 B2 | 3/2010 | Chan et al. |
| 7,693,683 B2 | 4/2010 | Ihara |
| 7,697,785 B2 | 4/2010 | Chiu et al. |
| 7,702,155 B2 | 4/2010 | Glickman et al. |
| 7,702,660 B2 | 4/2010 | Chan et al. |
| 7,707,210 B2 | 4/2010 | Stefik et al. |
| 7,711,846 B2 | 5/2010 | Padmanabhan et al. |
| 7,716,148 B2 | 5/2010 | Meng et al. |
| 7,736,905 B2 | 6/2010 | Roder et al. |
| 7,739,284 B2 | 6/2010 | Aggarwal et al. |
| 7,743,059 B2 | 6/2010 | Chan et al. |
| 7,746,534 B2 | 6/2010 | Tonar et al. |
| 7,747,054 B2 | 6/2010 | Zhou et al. |
| 7,747,390 B2 | 6/2010 | Miyake et al. |
| 7,747,547 B1 | 6/2010 | Buturovic et al. |
| 7,752,208 B2 | 7/2010 | Amitay et al. |
| 7,761,448 B2 | 7/2010 | Meyerzon et al. |
| 7,767,395 B2 | 8/2010 | Garrett et al. |
| 7,773,784 B2 | 8/2010 | Boult |
| 7,783,249 B2 | 8/2010 | Robinson |
| 7,801,685 B2 | 9/2010 | Ho |
| 7,801,893 B2 | 9/2010 | Gulli' et al. |
| 7,805,266 B1 | 9/2010 | Dasu et al. |
| 7,805,443 B2 | 9/2010 | Konig et al. |
| 7,805,496 B2 | 9/2010 | Aiber et al. |
| 7,813,580 B2 | 10/2010 | Lee et al. |
| 7,822,426 B1 | 10/2010 | Wuersch |
| 7,823,055 B2 | 10/2010 | Sull et al. |
| 7,826,635 B2 | 11/2010 | Barbara |
| 7,827,181 B2 | 11/2010 | Petriuc |
| 7,827,183 B2 | 11/2010 | Fraser et al. |
| 7,831,325 B1 | 11/2010 | Zhang et al. |
| 7,831,531 B1 | 11/2010 | Baluja et al. |
| 7,831,549 B2 | 11/2010 | Tilei et al. |
| 7,835,542 B2 | 11/2010 | Lin et al. |
| 7,842,874 B2 | 11/2010 | Jehan |
| 7,848,567 B2 | 12/2010 | Chiu et al. |
| 7,849,027 B2 | 12/2010 | Koran et al. |
| 7,856,434 B2 | 12/2010 | Gluzman Peregrine et al. |
| 7,865,456 B2 | 1/2011 | Aggarwal et al. |
| 7,868,786 B2 | 1/2011 | Toyama et al. |
| 7,873,616 B2 | 1/2011 | Schickel-Zuber et al. |
| 7,876,947 B2 | 1/2011 | Lee et al. |
| 7,879,620 B2 | 2/2011 | Roder et al. |
| 7,882,119 B2 | 2/2011 | Bergholz et al. |
| 7,882,126 B2 | 2/2011 | Vlachos et al. |
| 7,885,966 B2 | 2/2011 | Wolman |
| 7,889,679 B2 | 2/2011 | Canright et al. |
| 7,889,914 B2 | 2/2011 | Regli et al. |
| 7,890,294 B2 | 2/2011 | Castelli et al. |
| 7,890,510 B2 | 2/2011 | Aggarwal et al. |
| 7,890,512 B2 | 2/2011 | Mei et al. |
| 7,894,669 B2 | 2/2011 | Gloudemans, II et al. |
| 7,894,995 B2 | 2/2011 | Jojic et al. |
| 7,899,564 B2 | 3/2011 | Bech et al. |
| 7,904,303 B2 | 3/2011 | Chien et al. |
| 7,912,284 B2 | 3/2011 | Amini et al. |
| 7,912,290 B2 | 3/2011 | Glickman et al. |
| 7,912,726 B2 | 3/2011 | Alshawi et al. |
| 7,912,734 B2 | 3/2011 | Kil |
| 7,917,306 B2 | 3/2011 | Frumkin et al. |
| 7,917,517 B2 | 3/2011 | Aggarwal et al. |
| 7,926,026 B2 | 4/2011 | Klein et al. |
| 7,930,189 B2 | 4/2011 | Kuo |
| 7,933,740 B2 | 4/2011 | Castelli et al. |
| 7,933,915 B2 | 4/2011 | Singh et al. |
| 7,937,234 B2 | 5/2011 | St. Pierre et al. |
| 7,937,349 B2 | 5/2011 | Pucher |
| 7,949,186 B2 | 5/2011 | Grauman et al. |
| 7,953,679 B2 | 5/2011 | Chidlovskii et al. |
| 7,953,705 B2 | 5/2011 | Chron et al. |
| 7,954,090 B1 | 5/2011 | Qureshi et al. |
| 7,958,096 B2 | 6/2011 | Perrizo |

(56) References Cited

U.S. PATENT DOCUMENTS

| | | |
|---|---|---|
| 7,962,651 B2 | 6/2011 | Huitema et al. |
| 7,966,130 B2 | 6/2011 | Stoughton et al. |
| 7,966,225 B2 | 6/2011 | Chan et al. |
| 7,966,327 B2 | 6/2011 | Li et al. |
| 7,970,627 B2 | 6/2011 | Kuo et al. |
| 7,975,035 B2 | 7/2011 | Popescu et al. |
| 7,975,039 B2 | 7/2011 | Popescu et al. |
| 7,979,362 B2 | 7/2011 | Zhao et al. |
| 7,979,435 B2 | 7/2011 | Oisel et al. |
| 7,991,557 B2 | 8/2011 | Liew et al. |
| 7,996,369 B2 | 8/2011 | Li et al. |
| 8,000,527 B2 | 8/2011 | Grady et al. |
| 8,000,533 B2 | 8/2011 | Matsushita et al. |
| 8,005,294 B2 | 8/2011 | Kundu et al. |
| 8,010,466 B2 | 8/2011 | Patinkin |
| 8,010,589 B2 | 8/2011 | Peng et al. |
| 8,014,591 B2 | 9/2011 | Baker |
| 8,014,957 B2 | 9/2011 | Radich et al. |
| 8,015,124 B2 | 9/2011 | Milo et al. |
| 8,015,125 B2 | 9/2011 | Regli et al. |
| 8,015,183 B2 | 9/2011 | Frank |
| 8,019,766 B2 | 9/2011 | Chan et al. |
| 8,027,977 B2 | 9/2011 | Thambiratnam et al. |
| 8,032,476 B2 | 10/2011 | Nakano |
| 8,041,715 B2 | 10/2011 | Gnanamani et al. |
| 8,046,362 B2 | 10/2011 | Bayliss |
| 8,051,082 B2 | 11/2011 | Koran et al. |
| 8,051,139 B1 | 11/2011 | Musat |
| 8,055,677 B2 | 11/2011 | Wolman |
| 8,065,248 B1 | 11/2011 | Baluja et al. |
| 8,065,316 B1 | 11/2011 | Baker et al. |
| 8,073,652 B2 | 12/2011 | Grichnik et al. |
| 8,077,984 B2 | 12/2011 | Cancedda et al. |
| 8,082,246 B2 | 12/2011 | Meyerzon et al. |
| 8,090,729 B2 | 1/2012 | Gollapudi |
| 8,095,389 B2 | 1/2012 | Dalton et al. |
| 8,095,521 B2 | 1/2012 | Chan et al. |
| 8,095,830 B1 | 1/2012 | Cohen et al. |
| 8,097,469 B2 | 1/2012 | Roder et al. |
| 8,099,381 B2 | 1/2012 | Chi et al. |
| 8,108,392 B2 | 1/2012 | Marvit et al. |
| 8,108,405 B2 | 1/2012 | Marvit et al. |
| 8,108,931 B1 | 1/2012 | Witten et al. |
| 8,116,566 B2 | 2/2012 | Kirby et al. |
| 8,117,139 B2 | 2/2012 | Bonabeau et al. |
| 8,117,203 B2 | 2/2012 | Gazen et al. |
| 8,117,204 B2 | 2/2012 | Girgensohn et al. |
| 8,117,213 B1 | 2/2012 | Nakano et al. |
| 8,122,045 B2 | 2/2012 | Lingenfelder et al. |
| 8,122,502 B2 | 2/2012 | Gurda et al. |
| 8,135,679 B2 | 3/2012 | Bayliss |
| 8,135,680 B2 | 3/2012 | Bayliss |
| 8,135,681 B2 | 3/2012 | Bayliss |
| 8,135,719 B2 | 3/2012 | Bayliss |
| 8,139,838 B2 | 3/2012 | Sun et al. |
| 8,145,669 B2 | 3/2012 | Cormode et al. |
| 8,150,169 B2 | 4/2012 | Kovtun et al. |
| 8,164,507 B2 | 4/2012 | Howe et al. |
| 8,165,406 B2 | 4/2012 | Tan et al. |
| 8,165,407 B1 | 4/2012 | Khosla et al. |
| 8,169,481 B2 | 5/2012 | Ozdemir et al. |
| 8,169,681 B2 | 5/2012 | Tonar et al. |
| 8,170,306 B2 | 5/2012 | Yu et al. |
| 8,170,961 B2 | 5/2012 | Bangalore et al. |
| 8,175,412 B2 | 5/2012 | Basri et al. |
| 8,175,730 B2 | 5/2012 | Dittmar et al. |
| 8,175,896 B2 | 5/2012 | Dalton et al. |
| 8,180,147 B2 | 5/2012 | Baker |
| 8,180,627 B2 | 5/2012 | Bogl et al. |
| 8,180,766 B2 | 5/2012 | Yang et al. |
| 8,183,050 B2 | 5/2012 | Shi et al. |
| 8,184,913 B2 | 5/2012 | Baker et al. |
| 8,190,082 B2 | 5/2012 | Robinson |
| 8,190,663 B2 | 5/2012 | Schnitzer |
| 8,191,783 B2 | 6/2012 | Cheon |
| 8,195,345 B2 | 6/2012 | Omar et al. |
| 8,195,670 B2 | 6/2012 | Bayliss |
| 8,195,734 B1 | 6/2012 | Long et al. |
| 8,200,506 B2 | 6/2012 | Kil |
| 8,200,648 B2 | 6/2012 | Boiman et al. |
| 2001/0000356 A1 | 4/2001 | Woods |
| 2001/0014868 A1 | 8/2001 | Herz et al. |
| 2001/0048753 A1 | 12/2001 | Lee et al. |
| 2001/0055019 A1 | 12/2001 | Sowizral et al. |
| 2002/0000986 A1 | 1/2002 | Sowizral et al. |
| 2002/0002550 A1 | 1/2002 | Berman |
| 2002/0002555 A1 | 1/2002 | Wolman et al. |
| 2002/0023061 A1 | 2/2002 | Stewart et al. |
| 2002/0033835 A1 | 3/2002 | Sowizral et al. |
| 2002/0049740 A1 | 4/2002 | Arning et al. |
| 2002/0050990 A1 | 5/2002 | Sowizral et al. |
| 2002/0069218 A1 | 6/2002 | Sull et al. |
| 2002/0091655 A1 | 7/2002 | Agrafiotis et al. |
| 2002/0099675 A1 | 7/2002 | Agrafiotis et al. |
| 2002/0099721 A1 | 7/2002 | Ganapathy et al. |
| 2002/0111966 A1 | 8/2002 | Fukuda et al. |
| 2002/0115070 A1 | 8/2002 | Tamayo et al. |
| 2002/0122587 A1 | 9/2002 | Lim et al. |
| 2002/0128781 A1 | 9/2002 | Stoughton et al. |
| 2002/0129038 A1 | 9/2002 | Cunningham |
| 2002/0131641 A1 | 9/2002 | Luo et al. |
| 2002/0132479 A1 | 9/2002 | Coumou |
| 2002/0143989 A1 | 10/2002 | Huitema et al. |
| 2002/0146175 A1 | 10/2002 | Goldfoot |
| 2002/0147703 A1 | 10/2002 | Yu et al. |
| 2002/0181711 A1 | 12/2002 | Logan et al. |
| 2002/0181786 A1 | 12/2002 | Stark et al. |
| 2002/0183966 A1 | 12/2002 | Mishra et al. |
| 2002/0184080 A1 | 12/2002 | Murad et al. |
| 2002/0190198 A1 | 12/2002 | Mickael |
| 2002/0191034 A1 | 12/2002 | Sowizral et al. |
| 2003/0009333 A1 | 1/2003 | Sharma et al. |
| 2003/0009469 A1 | 1/2003 | Platt et al. |
| 2003/0014191 A1 | 1/2003 | Agrafiotis et al. |
| 2003/0016250 A1 | 1/2003 | Chang et al. |
| 2003/0028564 A1 | 2/2003 | Sanfilippo |
| 2003/0033138 A1 | 2/2003 | Bangalore et al. |
| 2003/0036093 A1 | 2/2003 | Floudas et al. |
| 2003/0044053 A1 | 3/2003 | Avni et al. |
| 2003/0044062 A1 | 3/2003 | Ganapathy et al. |
| 2003/0046018 A1 | 3/2003 | Kohlmorgen et al. |
| 2003/0046253 A1 | 3/2003 | Shetty et al. |
| 2003/0050908 A1 | 3/2003 | Kreulen et al. |
| 2003/0050923 A1 | 3/2003 | Chang et al. |
| 2003/0054573 A1 | 3/2003 | Tanaka et al. |
| 2003/0058339 A1 | 3/2003 | Trajkovic et al. |
| 2003/0059081 A1 | 3/2003 | Trajkovic |
| 2003/0061249 A1 | 3/2003 | Ramaswamy et al. |
| 2003/0065635 A1 | 4/2003 | Sahami et al. |
| 2003/0065661 A1 | 4/2003 | Chang et al. |
| 2003/0074251 A1 | 4/2003 | Kumar et al. |
| 2003/0078494 A1 | 4/2003 | Panescu et al. |
| 2003/0078509 A1 | 4/2003 | Panescu |
| 2003/0088563 A1 | 5/2003 | Yamane et al. |
| 2003/0093227 A1 | 5/2003 | Stoughton et al. |
| 2003/0097356 A1 | 5/2003 | Lee et al. |
| 2003/0097357 A1 | 5/2003 | Ferrari et al. |
| 2003/0100996 A1 | 5/2003 | Yang et al. |
| 2003/0101003 A1 | 5/2003 | Benight et al. |
| 2003/0107768 A1 | 6/2003 | Crounse |
| 2003/0120630 A1 | 6/2003 | Tunkelang |
| 2003/0129660 A1 | 7/2003 | Zien et al. |
| 2003/0138978 A1 | 7/2003 | Tanaka et al. |
| 2003/0139851 A1 | 7/2003 | Nakadai et al. |
| 2003/0145014 A1 | 7/2003 | Minch |
| 2003/0158842 A1 | 8/2003 | Levy et al. |
| 2003/0161396 A1 | 8/2003 | Foote et al. |
| 2003/0161500 A1 | 8/2003 | Blake et al. |
| 2003/0174179 A1 | 9/2003 | Suermondt et al. |
| 2003/0175720 A1 | 9/2003 | Bozinov et al. |
| 2003/0205124 A1 | 11/2003 | Foote et al. |
| 2003/0208488 A1 | 11/2003 | Perrizo |
| 2003/0229635 A1 | 12/2003 | Chaudhuri et al. |
| 2004/0002954 A1 | 1/2004 | Chaudhuri et al. |

(56) References Cited

U.S. PATENT DOCUMENTS

| | | |
|---|---|---|
| 2004/0002973 A1 | 1/2004 | Chaudhuri et al. |
| 2004/0003005 A1 | 1/2004 | Chaudhuri et al. |
| 2004/0013292 A1 | 1/2004 | Raunig |
| 2004/0019574 A1 | 1/2004 | Meng et al. |
| 2004/0024739 A1 | 2/2004 | Copperman et al. |
| 2004/0024758 A1 | 2/2004 | Iwasaki |
| 2004/0024773 A1 | 2/2004 | Stoffel et al. |
| 2004/0036716 A1 | 2/2004 | Jordahl |
| 2004/0048264 A1 | 3/2004 | Stoughton et al. |
| 2004/0049517 A1 | 3/2004 | Singh |
| 2004/0056778 A1 | 3/2004 | Hilliard |
| 2004/0068332 A1 | 4/2004 | Ben-Gal et al. |
| 2004/0071368 A1 | 4/2004 | Chadha et al. |
| 2004/0075656 A1 | 4/2004 | Kimia et al. |
| 2004/0091933 A1 | 5/2004 | Stoughton et al. |
| 2004/0101198 A1 | 5/2004 | Barbara |
| 2004/0103377 A1 | 5/2004 | Eaton et al. |
| 2004/0107205 A1 | 6/2004 | Burdick et al. |
| 2004/0122797 A1 | 6/2004 | Mishra et al. |
| 2004/0127777 A1 | 7/2004 | Ruchti et al. |
| 2004/0129199 A1 | 7/2004 | Hamrick et al. |
| 2004/0130546 A1 | 7/2004 | Porikli |
| 2004/0139067 A1 | 7/2004 | Houle |
| 2004/0162647 A1 | 8/2004 | Koshizen et al. |
| 2004/0162834 A1 | 8/2004 | Aono et al. |
| 2004/0170318 A1 | 9/2004 | Crandall et al. |
| 2004/0171063 A1 | 9/2004 | Fidelis et al. |
| 2004/0172225 A1 | 9/2004 | Hochberg et al. |
| 2004/0175700 A1 | 9/2004 | Geesaman |
| 2004/0177069 A1 | 9/2004 | Li et al. |
| 2004/0181527 A1 | 9/2004 | Burdick et al. |
| 2004/0213461 A1 | 10/2004 | Goldfoot |
| 2004/0230586 A1 | 11/2004 | Wolman |
| 2004/0233987 A1 | 11/2004 | Porikli et al. |
| 2004/0243362 A1 | 12/2004 | Liebman |
| 2004/0249789 A1 | 12/2004 | Kapoor et al. |
| 2004/0249939 A1 | 12/2004 | Amini et al. |
| 2004/0254901 A1 | 12/2004 | Bonabeau et al. |
| 2004/0260694 A1 | 12/2004 | Chaudhuri et al. |
| 2004/0267774 A1 | 12/2004 | Lin et al. |
| 2005/0010571 A1 | 1/2005 | Solotorevsky et al. |
| 2005/0015376 A1 | 1/2005 | Fraser et al. |
| 2005/0027829 A1 | 2/2005 | Mukherjee |
| 2005/0058336 A1 | 3/2005 | Russell et al. |
| 2005/0075995 A1 | 4/2005 | Stewart et al. |
| 2005/0085436 A1 | 4/2005 | Li et al. |
| 2005/0102272 A1 | 5/2005 | Kumar et al. |
| 2005/0102305 A1 | 5/2005 | Chaudhuri et al. |
| 2005/0114331 A1 | 5/2005 | Wang et al. |
| 2005/0120105 A1 | 6/2005 | Popescu et al. |
| 2005/0130215 A1 | 6/2005 | Stoughton et al. |
| 2005/0130230 A1 | 6/2005 | Davalos et al. |
| 2005/0132069 A1 | 6/2005 | Shannon et al. |
| 2005/0137806 A1 | 6/2005 | Kutsyy et al. |
| 2005/0138056 A1 | 6/2005 | Stefik et al. |
| 2005/0147303 A1 | 7/2005 | Zhou et al. |
| 2005/0149269 A1 | 7/2005 | Thomas et al. |
| 2005/0163373 A1 | 7/2005 | Lee et al. |
| 2005/0163384 A1 | 7/2005 | Avni et al. |
| 2005/0164273 A1 | 7/2005 | Stoughton et al. |
| 2005/0175244 A1 | 8/2005 | Glickman et al. |
| 2005/0176057 A1 | 8/2005 | Bremer et al. |
| 2005/0180638 A1 | 8/2005 | Glickman et al. |
| 2005/0182570 A1 | 8/2005 | Geourjon et al. |
| 2005/0185848 A1 | 8/2005 | Glickman et al. |
| 2005/0192768 A1 | 9/2005 | Tashev |
| 2005/0193216 A1 | 9/2005 | Gurda et al. |
| 2005/0198575 A1 | 9/2005 | Liu et al. |
| 2005/0225678 A1 | 10/2005 | Zisserman et al. |
| 2005/0251882 A1 | 11/2005 | D'Ordine et al. |
| 2005/0255458 A1 | 11/2005 | Polansky |
| 2005/0256413 A1 | 11/2005 | Astrom et al. |
| 2005/0262044 A1 | 11/2005 | Chaudhuri et al. |
| 2005/0265331 A1 | 12/2005 | Stolfo |
| 2005/0267991 A1 | 12/2005 | Huitema et al. |
| 2005/0267992 A1 | 12/2005 | Huitema et al. |
| 2005/0267993 A1 | 12/2005 | Huitema et al. |
| 2005/0273319 A1 | 12/2005 | Dittmar et al. |
| 2005/0278324 A1 | 12/2005 | Fan et al. |
| 2005/0281291 A1 | 12/2005 | Stolfo et al. |
| 2005/0283328 A1 | 12/2005 | Tashev |
| 2005/0285937 A1 | 12/2005 | Porikli |
| 2005/0286774 A1 | 12/2005 | Porikli |
| 2006/0013482 A1 | 1/2006 | Dawant et al. |
| 2006/0015341 A1 | 1/2006 | Baker |
| 2006/0015630 A1 | 1/2006 | Stolfo et al. |
| 2006/0020662 A1 | 1/2006 | Robinson |
| 2006/0026152 A1* | 2/2006 | Zeng ............. G06F 17/30864 707/1 |
| 2006/0031219 A1 | 2/2006 | Chernyak et al. |
| 2006/0034545 A1 | 2/2006 | Mattes et al. |
| 2006/0041414 A1 | 2/2006 | Ho |
| 2006/0052943 A1 | 3/2006 | Ramani et al. |
| 2006/0053129 A1 | 3/2006 | Motwani et al. |
| 2006/0053142 A1 | 3/2006 | Sebbane |
| 2006/0058592 A1 | 3/2006 | Bouma et al. |
| 2006/0064177 A1 | 3/2006 | Tian et al. |
| 2006/0074621 A1 | 4/2006 | Rachman |
| 2006/0074771 A1 | 4/2006 | Kim et al. |
| 2006/0074924 A1 | 4/2006 | Tilei et al. |
| 2006/0093188 A1 | 5/2006 | Blake et al. |
| 2006/0093208 A1 | 5/2006 | Li et al. |
| 2006/0095521 A1 | 5/2006 | Patinkin |
| 2006/0101060 A1 | 5/2006 | Li et al. |
| 2006/0101377 A1 | 5/2006 | Toyama et al. |
| 2006/0106816 A1 | 5/2006 | Oisel et al. |
| 2006/0112146 A1 | 5/2006 | Song et al. |
| 2006/0136589 A1 | 6/2006 | Konig et al. |
| 2006/0177837 A1 | 8/2006 | Borozan et al. |
| 2006/0190191 A1 | 8/2006 | Stoughton et al. |
| 2006/0190465 A1 | 8/2006 | Nakano |
| 2006/0195204 A1 | 8/2006 | Bonabeau et al. |
| 2006/0195269 A1 | 8/2006 | Yeatman et al. |
| 2006/0195415 A1 | 8/2006 | Meyer |
| 2006/0208185 A1 | 9/2006 | Be'er et al. |
| 2006/0212337 A1 | 9/2006 | Vayghan et al. |
| 2006/0224356 A1 | 10/2006 | Castelli et al. |
| 2006/0239338 A1 | 10/2006 | Kolanek et al. |
| 2006/0246495 A1 | 11/2006 | Garrett et al. |
| 2006/0248141 A1 | 11/2006 | Mukherjee |
| 2006/0253258 A1 | 11/2006 | Miyake |
| 2006/0281473 A1 | 12/2006 | Debany et al. |
| 2006/0282298 A1 | 12/2006 | Azvine et al. |
| 2006/0282425 A1 | 12/2006 | Aggarwal et al. |
| 2007/0003138 A1 | 1/2007 | Hobson et al. |
| 2007/0005556 A1 | 1/2007 | Ganti et al. |
| 2007/0006177 A1 | 1/2007 | Aiber et al. |
| 2007/0008905 A1 | 1/2007 | Berger et al. |
| 2007/0022279 A1 | 1/2007 | Wu et al. |
| 2007/0025637 A1 | 2/2007 | Setlur et al. |
| 2007/0033170 A1 | 2/2007 | Sull et al. |
| 2007/0033214 A1 | 2/2007 | Lewis et al. |
| 2007/0033221 A1 | 2/2007 | Copperman et al. |
| 2007/0033292 A1 | 2/2007 | Sull et al. |
| 2007/0033515 A1 | 2/2007 | Sull et al. |
| 2007/0033521 A1 | 2/2007 | Sull et al. |
| 2007/0033533 A1 | 2/2007 | Sull |
| 2007/0038612 A1 | 2/2007 | Sull et al. |
| 2007/0044010 A1 | 2/2007 | Sull et al. |
| 2007/0050708 A1 | 3/2007 | Gupta et al. |
| 2007/0054266 A1 | 3/2007 | Sato et al. |
| 2007/0064627 A1 | 3/2007 | Campos |
| 2007/0067212 A1 | 3/2007 | Bonabeau |
| 2007/0078846 A1 | 4/2007 | Gulli et al. |
| 2007/0092888 A1 | 4/2007 | Diamond et al. |
| 2007/0092905 A1 | 4/2007 | Gimzewski et al. |
| 2007/0093966 A1 | 4/2007 | Southern et al. |
| 2007/0106405 A1 | 5/2007 | Cook et al. |
| 2007/0111316 A1 | 5/2007 | Shi et al. |
| 2007/0112758 A1* | 5/2007 | Livaditis ......... G06F 17/30696 707/1 |
| 2007/0128573 A1 | 6/2007 | Kuo |
| 2007/0129011 A1 | 6/2007 | Lal et al. |
| 2007/0129991 A1 | 6/2007 | Kuo |

(56) References Cited

U.S. PATENT DOCUMENTS

| | | |
|---|---|---|
| 2007/0141527 A1 | 6/2007 | Kuo et al. |
| 2007/0150443 A1 | 6/2007 | Bergholz et al. |
| 2007/0154066 A1 | 7/2007 | Lin et al. |
| 2007/0154931 A1 | 7/2007 | Radich et al. |
| 2007/0156516 A1 | 7/2007 | Moissinac et al. |
| 2007/0172803 A1 | 7/2007 | Hannaford et al. |
| 2007/0174267 A1* | 7/2007 | Patterson et al. .......... 707/5 |
| 2007/0174335 A1 | 7/2007 | Konig et al. |
| 2007/0179784 A1 | 8/2007 | Thambiratnam et al. |
| 2007/0180980 A1 | 8/2007 | Kim |
| 2007/0185946 A1 | 8/2007 | Basri et al. |
| 2007/0192034 A1 | 8/2007 | Benight et al. |
| 2007/0192063 A1 | 8/2007 | Abu-El-Zeet et al. |
| 2007/0198553 A1 | 8/2007 | Wolman |
| 2007/0217676 A1 | 9/2007 | Grauman et al. |
| 2007/0231921 A1 | 10/2007 | Roder et al. |
| 2007/0233711 A1 | 10/2007 | Aggarwal et al. |
| 2007/0239694 A1 | 10/2007 | Singh et al. |
| 2007/0239741 A1 | 10/2007 | Jordahl |
| 2007/0239982 A1 | 10/2007 | Aggarwal et al. |
| 2007/0244768 A1 | 10/2007 | Nguyen et al. |
| 2007/0250522 A1 | 10/2007 | Perrizo |
| 2007/0255707 A1 | 11/2007 | Tresser et al. |
| 2007/0263900 A1 | 11/2007 | Medasani et al. |
| 2007/0269804 A1 | 11/2007 | Liew et al. |
| 2007/0275108 A1 | 11/2007 | Geesamen |
| 2007/0276723 A1 | 11/2007 | Samid |
| 2007/0285575 A1 | 12/2007 | Gloudemans, II et al. |
| 2007/0286489 A1 | 12/2007 | Amini et al. |
| 2007/0288465 A1 | 12/2007 | Aggarwal et al. |
| 2007/0291958 A1 | 12/2007 | Jehan |
| 2008/0005137 A1 | 1/2008 | Surendran et al. |
| 2008/0010045 A1 | 1/2008 | Black et al. |
| 2008/0010262 A1 | 1/2008 | Frank |
| 2008/0010272 A1 | 1/2008 | Schickel-Zuber et al. |
| 2008/0010273 A1 | 1/2008 | Frank |
| 2008/0010605 A1 | 1/2008 | Frank |
| 2008/0030836 A1 | 2/2008 | Tonar et al. |
| 2008/0033658 A1 | 2/2008 | Dalton et al. |
| 2008/0037536 A1 | 2/2008 | Padmanabhan et al. |
| 2008/0037872 A1 | 2/2008 | Lee et al. |
| 2008/0057590 A1 | 3/2008 | Urdea et al. |
| 2008/0069437 A1 | 3/2008 | Baker |
| 2008/0077570 A1 | 3/2008 | Tang et al. |
| 2008/0082426 A1 | 4/2008 | Gokturk et al. |
| 2008/0091423 A1 | 4/2008 | Roy et al. |
| 2008/0097820 A1 | 4/2008 | Koran et al. |
| 2008/0101705 A1 | 5/2008 | Mohamed et al. |
| 2008/0109288 A1 | 5/2008 | Borkovec et al. |
| 2008/0112684 A1 | 5/2008 | Matsushita et al. |
| 2008/0114564 A1 | 5/2008 | Ihara |
| 2008/0114710 A1 | 5/2008 | Pucher |
| 2008/0114756 A1 | 5/2008 | Konig et al. |
| 2008/0114800 A1 | 5/2008 | Gazen et al. |
| 2008/0123940 A1 | 5/2008 | Kundu et al. |
| 2008/0126464 A1 | 5/2008 | Mowzoon |
| 2008/0144943 A1 | 6/2008 | Gokturk et al. |
| 2008/0146334 A1 | 6/2008 | Kil |
| 2008/0147438 A1 | 6/2008 | Kil |
| 2008/0147440 A1 | 6/2008 | Kil |
| 2008/0147441 A1 | 6/2008 | Kil |
| 2008/0147591 A1 | 6/2008 | Koran et al. |
| 2008/0147655 A1 | 6/2008 | Sinha et al. |
| 2008/0152231 A1 | 6/2008 | Gokturk et al. |
| 2008/0155335 A1 | 6/2008 | Klein et al. |
| 2008/0162541 A1 | 7/2008 | Oresic et al. |
| 2008/0177538 A1 | 7/2008 | Roy et al. |
| 2008/0177640 A1 | 7/2008 | Gokturk et al. |
| 2008/0181479 A1 | 7/2008 | Yang et al. |
| 2008/0182282 A1 | 7/2008 | Markman et al. |
| 2008/0183546 A1 | 7/2008 | Vayghan et al. |
| 2008/0188964 A1 | 8/2008 | Bech et al. |
| 2008/0189306 A1 | 8/2008 | Hewett et al. |
| 2008/0191035 A1 | 8/2008 | Cheon |
| 2008/0198160 A1 | 8/2008 | Kolmykov-Zotov et al. |
| 2008/0198231 A1 | 8/2008 | Ozdemir et al. |
| 2008/0201397 A1 | 8/2008 | Peng et al. |
| 2008/0208828 A1 | 8/2008 | Boiman et al. |
| 2008/0208855 A1 | 8/2008 | Lingenfelder et al. |
| 2008/0212899 A1 | 9/2008 | Gokturk et al. |
| 2008/0215510 A1 | 9/2008 | Regli et al. |
| 2008/0221876 A1 | 9/2008 | Holdrich |
| 2008/0222075 A1 | 9/2008 | Chron et al. |
| 2008/0222225 A1 | 9/2008 | Chron et al. |
| 2008/0226151 A1 | 9/2008 | Zouridakis et al. |
| 2008/0232687 A1 | 9/2008 | Petersohn |
| 2008/0234977 A1 | 9/2008 | Aggarwal et al. |
| 2008/0243637 A1 | 10/2008 | Chan et al. |
| 2008/0243638 A1 | 10/2008 | Chan et al. |
| 2008/0243815 A1 | 10/2008 | Chan et al. |
| 2008/0243816 A1 | 10/2008 | Chan et al. |
| 2008/0243817 A1 | 10/2008 | Chan et al. |
| 2008/0243839 A1 | 10/2008 | Gurda et al. |
| 2008/0249414 A1 | 10/2008 | Yang et al. |
| 2008/0256093 A1 | 10/2008 | Amitay et al. |
| 2008/0260247 A1 | 10/2008 | Grady et al. |
| 2008/0261516 A1 | 10/2008 | Robinson |
| 2008/0261820 A1 | 10/2008 | Iyengar et al. |
| 2008/0263088 A1 | 10/2008 | Webster et al. |
| 2008/0267471 A1 | 10/2008 | Yu et al. |
| 2008/0275671 A1 | 11/2008 | Castelli et al. |
| 2008/0300797 A1 | 12/2008 | Tabibiazar et al. |
| 2008/0300875 A1 | 12/2008 | Yao et al. |
| 2008/0302657 A1 | 12/2008 | Luten et al. |
| 2008/0310005 A1 | 12/2008 | Tonar et al. |
| 2008/0319973 A1 | 12/2008 | Thambiratnam et al. |
| 2009/0006378 A1 | 1/2009 | Houle |
| 2009/0010495 A1 | 1/2009 | Schamp et al. |
| 2009/0012766 A1 | 1/2009 | Miyake et al. |
| 2009/0022374 A1 | 1/2009 | Boult |
| 2009/0022472 A1 | 1/2009 | Bronstein et al. |
| 2009/0024555 A1 | 1/2009 | Rieck et al. |
| 2009/0028441 A1 | 1/2009 | Milo et al. |
| 2009/0043714 A1 | 2/2009 | Zhao et al. |
| 2009/0048841 A1 | 2/2009 | Pollet et al. |
| 2009/0055147 A1 | 2/2009 | Miyake et al. |
| 2009/0055257 A1 | 2/2009 | Chien et al. |
| 2009/0060042 A1 | 3/2009 | Lertrattanapanich et al. |
| 2009/0063537 A1 | 3/2009 | Bonnefoy-Cudraz et al. |
| 2009/0070346 A1 | 3/2009 | Savona et al. |
| 2009/0077093 A1 | 3/2009 | Sarma et al. |
| 2009/0080777 A1 | 3/2009 | Amini et al. |
| 2009/0081645 A1 | 3/2009 | Kotani et al. |
| 2009/0083211 A1 | 3/2009 | Sinha et al. |
| 2009/0093717 A1 | 4/2009 | Carneiro et al. |
| 2009/0094020 A1 | 4/2009 | Marvit et al. |
| 2009/0094021 A1 | 4/2009 | Marvit et al. |
| 2009/0094207 A1 | 4/2009 | Marvit et al. |
| 2009/0094208 A1 | 4/2009 | Marvit et al. |
| 2009/0094209 A1 | 4/2009 | Marvit et al. |
| 2009/0094231 A1 | 4/2009 | Marvit et al. |
| 2009/0094232 A1 | 4/2009 | Marvit et al. |
| 2009/0094233 A1 | 4/2009 | Marvit et al. |
| 2009/0094265 A1 | 4/2009 | Vlachos et al. |
| 2009/0097728 A1 | 4/2009 | Lee et al. |
| 2009/0104605 A1 | 4/2009 | Siuzdak et al. |
| 2009/0124512 A1 | 5/2009 | Rowlen et al. |
| 2009/0125482 A1 | 5/2009 | Peregrine et al. |
| 2009/0125916 A1 | 5/2009 | Lu et al. |
| 2009/0132347 A1 | 5/2009 | Anderson et al. |
| 2009/0150340 A1 | 6/2009 | Lhuillier et al. |
| 2009/0154795 A1 | 6/2009 | Tan et al. |
| 2009/0164192 A1 | 6/2009 | Yu |
| 2009/0169065 A1 | 7/2009 | Wang et al. |
| 2009/0175544 A1 | 7/2009 | Syeda-Mahmood et al. |
| 2009/0175545 A1 | 7/2009 | Cancedda et al. |
| 2009/0190798 A1 | 7/2009 | Lee et al. |
| 2009/0199099 A1 | 8/2009 | Girgensohn et al. |
| 2009/0204333 A1 | 8/2009 | Friend et al. |
| 2009/0204574 A1 | 8/2009 | Vlachos et al. |
| 2009/0204609 A1 | 8/2009 | Labrou et al. |
| 2009/0220488 A1 | 9/2009 | Gardner |
| 2009/0222430 A1 | 9/2009 | Hobson et al. |
| 2009/0226081 A1 | 9/2009 | Zhou et al. |

(56) References Cited

U.S. PATENT DOCUMENTS

| | | |
|---|---|---|
| 2009/0234876 A1 | 9/2009 | Schigel et al. |
| 2009/0248399 A1 | 10/2009 | Au |
| 2009/0252046 A1 | 10/2009 | Canright et al. |
| 2009/0265024 A1 | 10/2009 | Dittmar et al. |
| 2009/0271246 A1 | 10/2009 | Alvarez et al. |
| 2009/0271359 A1 | 10/2009 | Bayliss |
| 2009/0271363 A1 | 10/2009 | Bayliss |
| 2009/0271397 A1 | 10/2009 | Bayliss |
| 2009/0271404 A1 | 10/2009 | Bayliss |
| 2009/0271405 A1 | 10/2009 | Bayliss |
| 2009/0271424 A1 | 10/2009 | Bayliss |
| 2009/0271694 A1 | 10/2009 | Bayliss |
| 2009/0276705 A1 | 11/2009 | Ozdemir et al. |
| 2009/0277322 A1 | 11/2009 | Cai et al. |
| 2009/0287682 A1* | 11/2009 | Fujioka et al. .................... 707/5 |
| 2009/0287689 A1 | 11/2009 | Bayliss |
| 2009/0290778 A1 | 11/2009 | Sun et al. |
| 2009/0292482 A1 | 11/2009 | Frumkin et al. |
| 2009/0292694 A1 | 11/2009 | Bayliss |
| 2009/0292695 A1 | 11/2009 | Bayliss |
| 2009/0292802 A1 | 11/2009 | Popescu et al. |
| 2009/0297048 A1 | 12/2009 | Slotine et al. |
| 2009/0299705 A1 | 12/2009 | Chi et al. |
| 2009/0299822 A1 | 12/2009 | Harari et al. |
| 2009/0299990 A1 | 12/2009 | Setlur et al. |
| 2009/0311786 A1 | 12/2009 | Fire et al. |
| 2009/0313294 A1 | 12/2009 | Mei et al. |
| 2009/0318815 A1 | 12/2009 | Barnes et al. |
| 2009/0319454 A1 | 12/2009 | Regli et al. |
| 2009/0319526 A1 | 12/2009 | Aggarwal et al. |
| 2009/0326383 A1 | 12/2009 | Barnes et al. |
| 2009/0327185 A1 | 12/2009 | Castelli et al. |
| 2010/0004898 A1 | 1/2010 | Grichnik et al. |
| 2010/0004923 A1 | 1/2010 | Bogl et al. |
| 2010/0005105 A1 | 1/2010 | Zhang et al. |
| 2010/0017487 A1 | 1/2010 | Patinkin |
| 2010/0033182 A1 | 2/2010 | Ozarslan et al. |
| 2010/0034422 A1 | 2/2010 | James et al. |
| 2010/0036647 A1 | 2/2010 | Reem et al. |
| 2010/0042563 A1 | 2/2010 | Livingston et al. |
| 2010/0049431 A1 | 2/2010 | Zetune |
| 2010/0050260 A1 | 2/2010 | Nakakoji et al. |
| 2010/0054278 A1 | 3/2010 | Stolfo et al. |
| 2010/0055678 A1 | 3/2010 | Jaatinen et al. |
| 2010/0057391 A1 | 3/2010 | St. Pierre et al. |
| 2010/0057399 A1 | 3/2010 | Castelli et al. |
| 2010/0057534 A1 | 3/2010 | Gershkoff |
| 2010/0067745 A1 | 3/2010 | Kovtun et al. |
| 2010/0076981 A1 | 3/2010 | Nakano |
| 2010/0080439 A1 | 4/2010 | Karam et al. |
| 2010/0081661 A1 | 4/2010 | Wilks et al. |
| 2010/0082367 A1 | 4/2010 | Hains et al. |
| 2010/0082614 A1 | 4/2010 | Yang et al. |
| 2010/0085358 A1 | 4/2010 | Wegbreit et al. |
| 2010/0100515 A1 | 4/2010 | Bangalore et al. |
| 2010/0106713 A1 | 4/2010 | Esuli et al. |
| 2010/0111370 A1 | 5/2010 | Black et al. |
| 2010/0111396 A1 | 5/2010 | Boucheron |
| 2010/0112234 A1 | 5/2010 | Spatz et al. |
| 2010/0114928 A1 | 5/2010 | Bonchi et al. |
| 2010/0114929 A1 | 5/2010 | Bonchi et al. |
| 2010/0117978 A1 | 5/2010 | Shirado |
| 2010/0121638 A1 | 5/2010 | Pinson et al. |
| 2010/0125594 A1 | 5/2010 | Li et al. |
| 2010/0135582 A1 | 6/2010 | Gokturk et al. |
| 2010/0135597 A1 | 6/2010 | Gokturk et al. |
| 2010/0136553 A1 | 6/2010 | Black et al. |
| 2010/0138894 A1 | 6/2010 | Kyojima |
| 2010/0149917 A1 | 6/2010 | Imhof et al. |
| 2010/0150453 A1 | 6/2010 | Ravid et al. |
| 2010/0157089 A1 | 6/2010 | Pakulski et al. |
| 2010/0157340 A1 | 6/2010 | Chen et al. |
| 2010/0161232 A1 | 6/2010 | Chen et al. |
| 2010/0161590 A1 | 6/2010 | Zheng et al. |
| 2010/0166339 A1 | 7/2010 | Gokturk et al. |
| 2010/0169025 A1 | 7/2010 | Arthur et al. |
| 2010/0174492 A1 | 7/2010 | Roder et al. |
| 2010/0174732 A1 | 7/2010 | Levy et al. |
| 2010/0174976 A1 | 7/2010 | Mansfield et al. |
| 2010/0174977 A1 | 7/2010 | Mansfield et al. |
| 2010/0174978 A1 | 7/2010 | Mansfield et al. |
| 2010/0174979 A1 | 7/2010 | Mansfield et al. |
| 2010/0174980 A1 | 7/2010 | Mansfield et al. |
| 2010/0174982 A1 | 7/2010 | Mansfield et al. |
| 2010/0174983 A1 | 7/2010 | Levy et al. |
| 2010/0174985 A1 | 7/2010 | Levy et al. |
| 2010/0183555 A1 | 7/2010 | Vidaud et al. |
| 2010/0189333 A1 | 7/2010 | Beck et al. |
| 2010/0191532 A1 | 7/2010 | Rodriguez Serrano et al. |
| 2010/0191722 A1 | 7/2010 | Boiman et al. |
| 2010/0198864 A1 | 8/2010 | Ravid et al. |
| 2010/0199186 A1 | 8/2010 | Bonabeau et al. |
| 2010/0204061 A1 | 8/2010 | Roder et al. |
| 2010/0205213 A1 | 8/2010 | Broder et al. |
| 2010/0215903 A1 | 8/2010 | Tonar et al. |
| 2010/0216660 A1 | 8/2010 | Nikolsky et al. |
| 2010/0217763 A1 | 8/2010 | Park et al. |
| 2010/0221722 A1 | 9/2010 | Perou et al. |
| 2010/0228625 A1 | 9/2010 | Priyadarshan et al. |
| 2010/0228731 A1 | 9/2010 | Gollapudi |
| 2010/0232718 A1 | 9/2010 | Glickman et al. |
| 2010/0239147 A1 | 9/2010 | Vitanovski et al. |
| 2010/0250477 A1 | 9/2010 | Yadav |
| 2010/0250527 A1 | 9/2010 | Gnanamani et al. |
| 2010/0254614 A1 | 10/2010 | Baker et al. |
| 2010/0257092 A1 | 10/2010 | Einhorn |
| 2010/0268476 A1 | 10/2010 | Geourjon et al. |
| 2010/0268512 A1 | 10/2010 | Howe et al. |
| 2010/0278425 A1 | 11/2010 | Takemoto et al. |
| 2010/0280987 A1 | 11/2010 | Loboda et al. |
| 2010/0284915 A1 | 11/2010 | Dai et al. |
| 2010/0296748 A1 | 11/2010 | Shechtman et al. |
| 2010/0299128 A1 | 11/2010 | Aiber et al. |
| 2010/0305868 A1 | 12/2010 | Roder et al. |
| 2010/0305930 A1 | 12/2010 | Ho |
| 2010/0313157 A1 | 12/2010 | Carlsson et al. |
| 2010/0318492 A1 | 12/2010 | Utsugi |
| 2010/0322525 A1 | 12/2010 | Kohli et al. |
| 2010/0332210 A1 | 12/2010 | Birdwell et al. |
| 2010/0332242 A1 | 12/2010 | Kamar et al. |
| 2010/0332425 A1 | 12/2010 | Tuzel et al. |
| 2010/0332474 A1 | 12/2010 | Birdwell et al. |
| 2010/0332475 A1 | 12/2010 | Birdwell et al. |
| 2011/0002028 A1 | 1/2011 | Luten et al. |
| 2011/0002194 A1 | 1/2011 | Imhof et al. |
| 2011/0004115 A1 | 1/2011 | Shahaf et al. |
| 2011/0004415 A1 | 1/2011 | Miyake et al. |
| 2011/0004578 A1 | 1/2011 | Momma et al. |
| 2011/0008805 A1 | 1/2011 | Urdea et al. |
| 2011/0013840 A1 | 1/2011 | Iwasaki et al. |
| 2011/0015869 A1 | 1/2011 | Watters et al. |
| 2011/0020779 A1 | 1/2011 | Hannaford et al. |
| 2011/0022354 A1 | 1/2011 | Kumar |
| 2011/0022599 A1 | 1/2011 | Chidlovskii et al. |
| 2011/0029657 A1 | 2/2011 | Gueta et al. |
| 2011/0040192 A1 | 2/2011 | Brenner et al. |
| 2011/0047172 A1 | 2/2011 | Chen et al. |
| 2011/0048731 A1 | 3/2011 | Imhof et al. |
| 2011/0052076 A1 | 3/2011 | Yashiro |
| 2011/0055192 A1 | 3/2011 | Tang et al. |
| 2011/0060716 A1 | 3/2011 | Forman et al. |
| 2011/0060717 A1 | 3/2011 | Forman et al. |
| 2011/0078143 A1 | 3/2011 | Aggarwal |
| 2011/0078144 A1 | 3/2011 | Helfman et al. |
| 2011/0080490 A1 | 4/2011 | Clarkson et al. |
| 2011/0081056 A1 | 4/2011 | Salafia |
| 2011/0081066 A1 | 4/2011 | Jolly et al. |
| 2011/0086349 A1 | 4/2011 | Anjomshoaa et al. |
| 2011/0091073 A1 | 4/2011 | Iwasaki et al. |
| 2011/0091074 A1 | 4/2011 | Nobori et al. |
| 2011/0091083 A1 | 4/2011 | Liu et al. |
| 2011/0093482 A1 | 4/2011 | Wolman |
| 2011/0093492 A1 | 4/2011 | Sull et al. |
| 2011/0097001 A1 | 4/2011 | Labbi et al. |

(56) References Cited

U.S. PATENT DOCUMENTS

| | | | |
|---|---|---|---|
| 2011/0103613 A1 | 5/2011 | Van Der Werf et al. |
| 2011/0105340 A1 | 5/2011 | Tian et al. |
| 2011/0105350 A1 | 5/2011 | Garrett et al. |
| 2011/0106801 A1 | 5/2011 | Srivastava et al. |
| 2011/0115787 A1 | 5/2011 | Kadlec |
| 2011/0116690 A1 | 5/2011 | Ross et al. |
| 2011/0119108 A1 | 5/2011 | Black et al. |
| 2011/0124525 A1 | 5/2011 | Harbour |
| 2011/0142287 A1 | 6/2011 | Wong et al. |
| 2011/0142318 A1 | 6/2011 | Chen et al. |
| 2011/0143650 A1 | 6/2011 | Robinson |
| 2011/0144480 A1 | 6/2011 | Lu et al. |
| 2011/0144914 A1 | 6/2011 | Harrington et al. |
| 2011/0161205 A1 | 6/2011 | Nguyen et al. |
| 2011/0166949 A1 | 7/2011 | Nguyen et al. |
| 2011/0172501 A1 | 7/2011 | Antonijevic et al. |
| 2011/0173173 A1 | 7/2011 | Hall |
| 2011/0173189 A1 | 7/2011 | Singh et al. |
| 2011/0175905 A1 | 7/2011 | Hao |
| 2011/0178965 A1 | 7/2011 | Pucher |
| 2011/0179019 A1 | 7/2011 | Amer-Yahia et al. |
| 2011/0185234 A1 | 7/2011 | Cohen et al. |
| 2011/0191076 A1 | 8/2011 | Maeda et al. |
| 2011/0191283 A1 | 8/2011 | Voigt et al. |
| 2011/0191353 A1 | 8/2011 | L'Heureux et al. |
| 2011/0202540 A1 | 8/2011 | Nakano |
| 2011/0205399 A1 | 8/2011 | Gao et al. |
| 2011/0206246 A1 | 8/2011 | Wolf et al. |
| 2011/0218990 A1 | 9/2011 | Jordahl |
| 2011/0221767 A1 | 9/2011 | Kostrzewski et al. |
| 2011/0225158 A1 | 9/2011 | Snyder et al. |
| 2011/0231350 A1 * | 9/2011 | Momma et al. ............ 706/12 |
| 2011/0231414 A1 | 9/2011 | Goodwin et al. |
| 2011/0246200 A1 | 10/2011 | Song et al. |
| 2011/0246409 A1 | 10/2011 | Mitra |
| 2011/0246483 A1 | 10/2011 | Darr et al. |
| 2011/0251081 A1 | 10/2011 | Stoughton et al. |
| 2011/0255747 A1 | 10/2011 | Iwasaki et al. |
| 2011/0255748 A1 | 10/2011 | Komoto et al. |
| 2011/0261049 A1 | 10/2011 | Cardno et al. |
| 2011/0264432 A1 | 10/2011 | Penner et al. |
| 2011/0269479 A1 | 11/2011 | Ledlie |
| 2011/0282828 A1 | 11/2011 | Precup et al. |
| 2011/0282877 A1 | 11/2011 | Gazen et al. |
| 2011/0288890 A1 | 11/2011 | Dalton et al. |
| 2011/0295773 A1 | 12/2011 | Fisher et al. |
| 2011/0299765 A1 | 12/2011 | Baker |
| 2011/0301860 A1 | 12/2011 | Chaires et al. |
| 2011/0304619 A1 | 12/2011 | Fu et al. |
| 2011/0306354 A1 | 12/2011 | Ledlie et al. |
| 2011/0320396 A1 | 12/2011 | Hunt et al. |
| 2012/0005238 A1 | 1/2012 | Jebara et al. |
| 2012/0011135 A1 | 1/2012 | Wolman |
| 2012/0014560 A1 | 1/2012 | Obrador et al. |
| 2012/0015841 A1 | 1/2012 | Shekdar et al. |
| 2012/0021710 A1 | 1/2012 | Tsukamoto et al. |
| 2012/0030165 A1 | 2/2012 | Guirguis et al. |
| 2012/0030185 A1 | 2/2012 | Gnanamani et al. |
| 2012/0036096 A1 | 2/2012 | Omar et al. |
| 2012/0039541 A1 | 2/2012 | Fukui et al. |
| 2012/0041955 A1 | 2/2012 | Regev et al. |
| 2012/0045119 A1 | 2/2012 | Schamp |
| 2012/0047098 A1 | 2/2012 | Reem |
| 2012/0054133 A1 | 3/2012 | Jallon |
| 2012/0070452 A1 | 3/2012 | Akira et al. |
| 2012/0072124 A1 | 3/2012 | Radich et al. |
| 2012/0076372 A1 | 3/2012 | Nishimura et al. |
| 2012/0078858 A1 | 3/2012 | Nagpal et al. |
| 2012/0078906 A1 | 3/2012 | Anand et al. |
| 2012/0078927 A1 | 3/2012 | Gollapudi |
| 2012/0084251 A1 | 4/2012 | Lingenfelder et al. |
| 2012/0084283 A1 * | 4/2012 | Chitiveli ........... G06F 17/30648 707/728 |
| 2012/0088981 A1 | 4/2012 | Liu et al. |
| 2012/0089341 A1 | 4/2012 | Roder et al. |
| 2012/0109778 A1 | 5/2012 | Chan et al. |
| 2012/0123279 A1 | 5/2012 | Brueser et al. |
| 2012/0125178 A1 | 5/2012 | Cai et al. |
| 2012/0131701 A1 | 5/2012 | Shekdar |
| 2012/0136860 A1 | 5/2012 | Regli et al. |
| 2012/0137182 A1 | 5/2012 | Zhang et al. |

\* cited by examiner

INSIGHT AND ALGORITHMIC CLUSTERING FOR AUTOMATED SYNTHESIS

FIELD OF THE INVENTION

The present invention relates to the field of domain or context-specific automated data classification or truth-seeking, and more particularly to the field of semi-supervised data clustering.

BACKGROUND OF THE INVENTION

Investment Insights

Understanding the true value of assets of any kind is a critical problem in purchase decisions. Often, the available markets are inefficient at finding the true value (appropriate risk adjusted return) of the assets. As such, it is difficult for an investor or potential investor to make, monitor and communicate decisions around comparison of the value of two assets, comparing the value of two different asset types, and comparing the value of an asset to the market of all such assets.

Most types of assets have a price (as determined by what you pay for it) and a value (what it is actually worth). If you paid the right price, you would realize the expected value. Value is reflective of the price in relation to the risk-adjusted return. In poorly valued items, the price is subject to arbitrage. As the market becomes more efficient, the price and value should converge. Duration is the time horizon between when an interest in an asset is acquired as a primary and when sale, transfer, or the like realizes the complete value, e.g., in a completely measurable asset such as treasury cash, e.g., by sale, transfer, or the like. As the duration is increased, a secondary market or exchange may be available to trade the asset, and speculative investors may take part seeking to profit off changes in risk or reward over time, and often not focusing on the true value.

While there is much emphasis on data correctness, using incomplete data can also lead to faulty analysis. Overall completeness consists of the various completeness factors being monitored, as well as the timeliness of the data. Coverage refers to the percent of the total universe covered by a dataset and the expanse (or breadth) of the coverage. Proper coverage metrics must address the issue of whether a particular data set is indeed a representative sample of the space, such that analysis run on the data set gives results that are consistent with the same analysis on the full universe. Correctness, completeness and coverage are a function of the statistical confidence interval that is required by the user on the results. User may trade-off confidence to increase other parameters.

When investing in assets, each with its own risk and reward profile, it is important for an investor to understand what risks (including pricing risk) are being incurred, what return on investment is to be expected, what term/duration of investment is considered, and how a hypothetical efficient market would value the asset. In terms of market valuation (especially in an inefficient market that does not correctly price assets), it is important to compare an asset to three potential different valuation anchors, its "peers", or assets which have similar risks vs. returns to evaluate which provides superior value (or explained and accounted for differences in risk and reward profiles), the overall market benchmark (i.e. the largest universe of peers that represent the appropriate market) and potentially a broader category of peers from other markets (or clusters). In some cases, the identification of the peer group may be difficult, and not readily amenable to accurate fully automated determination. Humans, however, may have insights that can resolve this issue.

Some users may have superior insights into understanding the price, risks and rewards, and thus a better assessment of the value or risk adjusted return than others. Investors seek benefit of those with superior insights as advisors. Those with superior insights can recognize patterns that others might not see, and classify data and draw abstractions and conclusions differently than others. However, prospectively determining which advisor(s) to rely on in terms of superior return on investment while incurring acceptable risk remains an unresolved problem.

Data Clustering

Data clustering is a process of grouping together data points having common characteristics. In automated processes, a cost function or distance function is defined, and data is classified is belonging to various clusters by making decisions about its relationship to the various defined clusters (or automatically defined clusters) in accordance with the cost function or distance function. Therefore, the clustering problem is an automated decision-making problem. The science of clustering is well established, and various different paradigms are available. After the cost or distance function is defined and formulated as clustering criteria, the clustering process becomes one of optimization according to an optimization process, which itself may be imperfect or provide different optimized results in dependence on the particular optimization employed. For large data sets, a complete evaluation of a single optimum state may be infeasible, and therefore the optimization process subject to error, bias, ambiguity, or other known artifacts.

In some cases, the distribution of data is continuous, and the cluster boundaries sensitive to subjective considerations or have particular sensitivity to the aspects and characteristics of the clustering technology employed. In contrast, in other cases, the inclusion of data within a particular cluster is relatively insensitive to the clustering methodology. Likewise, in some cases, the use of the clustering results focuses on the marginal data, that is, the quality of the clustering is a critical factor in the use of the system.

The ultimate goal of clustering is to provide users with meaningful insights from the original data, so that they can effectively solve the problems encountered. Clustering acts to effectively reduce the dimensionality of a data set by treating each cluster as a degree of freedom, with a distance from a centroid or other characteristic exemplar of the set. In a non-hybrid system, the distance is a scalar, while in systems that retain some flexibility at the cost of complexity, the distance itself may be a vector. Thus, a data set with 10,000 data points, potentially has 10,000 degrees of freedom, that is, each data point represents the centroid of its own cluster. However, if it is clustered into 100 groups of 100 data points, the degrees of freedom is reduced to 100, with the remaining differences expressed as a distance from the cluster definition. Cluster analysis groups data objects based on information in or about the data that describes the objects and their relationships. The goal is that the objects within a group be similar (or related) to one another and different from (or unrelated to) the objects in other groups. The greater the similarity (or homogeneity) within a group and the greater the difference between groups, the "better" or more distinct is the clustering.

In some cases, the dimensionality may be reduced to one, in which case all of the dimensional variety of the data set is reduced to a distance according to a distance function. This distance function may be useful, since it permits dimensionless comparison of the entire data set, and allows a user to modify the distance function to meet various constraints. Likewise, in certain types of clustering, the distance functions for each cluster may be defined independently, and then applied to the entire data set. In other types of clustering, the distance function is defined for the entire data set, and is not (or cannot readily be) tweaked for each cluster. Similarly, feasible clustering algorithms for large data sets preferably do not have interactive distance functions in which the distance function itself changes depending on the data. Many clustering processes are iterative, and as such produce a putative clustering of the data, and then seek to produce a better clustering, and when a better clustering is found, making that the putative clustering. However, in complex data sets, there are relationships between data points such that a cost or penalty (or reward) is incurred if data points are clustered in a certain way. Thus, while the clustering algorithm may split data points which have an affinity (or group together data points, which have a negative affinity, the optimization becomes more difficult.

Thus, for example, a semantic database may be represented as a set of documents with words or phrases. Words may be ambiguous, such as "apple", representing a fruit, a computer company, a record company, and a musical artist. In order to effectively use the database, the multiple meanings or contexts need to be resolved. In order to resolve the context, an automated process might be used to exploit available information for separating the meanings, i.e., clustering documents according to their context. This automated process can be difficult as the data set grows, and in some cases the available information is insufficient for accurate automated clustering. On the other hand, a human can often determine a context by making an inference, which, though subject to error or bias, may represent a most useful result regardless.

In supervised classification, the mapping from a set of input data vectors to a finite set of discrete class labels is modeled in terms of some mathematical function including a vector of adjustable parameters. The values of these adjustable parameters are determined (optimized) by an inductive learning algorithm (also termed inducer), whose aim is to minimize an empirical risk function on a finite data set of input. When the inducer reaches convergence or terminates, an induced classifier is generated. In unsupervised classification, called clustering or exploratory data analysis, no labeled data are available. The goal of clustering is to separate a finite unlabeled data set into a finite and discrete set of "natural," hidden data structures, rather than provide an accurate characterization of unobserved samples generated from the same probability distribution. In semi-supervised classification, a portion of the data are labeled, or sparse label feedback is used during the process.

Non-predictive clustering is a subjective process in nature, seeking to ensure that the similarity between objects within a cluster is larger than the similarity between objects belonging to different clusters. Cluster analysis divides data into groups (clusters) that are meaningful, useful, or both. If meaningful groups are the goal, then the clusters should capture the "natural" structure of the data. In some cases, however, cluster analysis is only a useful starting point for other purposes, such as data summarization. However, this often begs the question, especially in marginal cases; what is the natural structure of the data, and how do we know when the clustering deviates from "truth"?

Many data analysis techniques, such as regression or principal component analysis (PCA), have a time or space complexity of $O(m^2)$ or higher (where m is the number of objects), and thus, are not practical for large data sets. However, instead of applying the algorithm to the entire data set, it can be applied to a reduced data set consisting only of cluster prototypes. Depending on the type of analysis, the number of prototypes, and the accuracy with which the prototypes represent the data, the results can be comparable to those that would have been obtained if all the data could have been used. The entire data set may then be assigned to the clusters based on a distance function.

Clustering algorithms partition data into a certain number of clusters (groups, subsets, or categories). Important considerations include feature selection or extraction (choosing distinguishing or important features, and only such features); Clustering algorithm design or selection (accuracy and precision with respect to the intended use of the classification result; feasibility and computational cost; etc.); and to the extent different from the clustering criterion, optimization algorithm design or selection.

Finding nearest neighbors can require computing the pairwise distance between all points. However, clusters and their cluster prototypes might be found more efficiently. Assuming that the clustering distance metric reasonably includes close points, and excludes far points, then the neighbor analysis may be limited to members of nearby clusters, thus reducing the complexity of the computation.

There are generally three types of clustering structures, known as partitional clustering, hierarchical clustering, and individual clusters. The most commonly discussed distinction among different types of clusterings is whether the set of clusters is nested or unnested, or in more traditional terminology, hierarchical or partitional. A partitional clustering is simply a division of the set of data objects into non-overlapping subsets (clusters) such that each data object is in exactly one subset. If the clusters have sub-clusters, then we obtain a hierarchical clustering, which is a set of nested clusters that are organized as a tree. Each node (cluster) in the tree (except for the leaf nodes) is the union of its children (sub-clusters), and the root of the tree is the cluster containing all the objects. Often, but not always, the leaves of the tree are singleton clusters of individual data objects. A hierarchical clustering can be viewed as a sequence of partitional clusterings and a partitional clustering can be obtained by taking any member of that sequence; i.e., by cutting the hierarchical tree at a particular level.

There are many situations in which a point could reasonably be placed in more than one cluster, and these situations are better addressed by non-exclusive clustering. In the most general sense, an overlapping or non-exclusive clustering is used to reflect the fact that an object can simultaneously belong to more than one group (class). A non-exclusive clustering is also often used when, for example, an object is "between" two or more clusters and could reasonably be assigned to any of these clusters. In a fuzzy clustering, every object belongs to every cluster with a membership weight. In other words, clusters are treated as fuzzy sets. Similarly, probabilistic clustering techniques compute the probability with which each point belongs to each cluster.

In many cases, a fuzzy or probabilistic clustering is converted to an exclusive clustering by assigning each object to the cluster in which its membership weight or probability is highest. Thus, the inter-cluster and intra-cluster distance function is symmetric. However, it is also possible to apply a different function to uniquely assign objects to a particular cluster.

A well-separated cluster is a set of objects in which each object is closer (or more similar) to every other object in the cluster than to any object not in the cluster. Sometimes a threshold is used to specify that all the objects in a cluster must be sufficiently close (or similar) to one another. The distance between any two points in different groups is larger than the distance between any two points within a group. Well-separated clusters do not need to be spheric, but can have any shape.

If the data is represented as a graph, where the nodes are objects and the links represent connections among objects, then a cluster can be defined as a connected component; i.e., a group of objects that are significantly connected to one another, but that have less connected to objects outside the group. This implies that each object in a contiguity-based cluster is closer to some other object in the cluster than to any point in a different cluster.

A density-based cluster is a dense region of objects that is surrounded by a region of low density. A density-based definition of a cluster is often employed when the clusters are irregular or intertwined, and when noise and outliers are present. DBSCAN is a density-based clustering algorithm that produces a partitional clustering, in which the number of clusters is automatically determined by the algorithm. Points in low-density regions are classified as noise and omitted; thus, DBSCAN does not produce a complete clustering.

A prototype-based cluster is a set of objects in which each object is closer (more similar) to the prototype that defines the cluster than to the prototype of any other cluster. For data with continuous attributes, the prototype of a cluster is often a centroid, i.e., the average (mean) of all the points in the cluster. When a centroid is not meaningful, such as when the data has categorical attributes, the prototype is often a medoid, i.e., the most representative point of a cluster. For many types of data, the prototype can be regarded as the most central point. These clusters tend to be globular. K-means is a prototype-based, partitional clustering technique that attempts to find a user-specified number of clusters (K), which are represented by their centroids. Prototype-based clustering techniques create a one-level partitioning of the data objects. There are a number of such techniques, but two of the most prominent are K-means and K-medoid. K-means defines a prototype in terms of a centroid, which is usually the mean of a group of points, and is typically applied to objects in a continuous n-dimensional space. K-medoid defines a prototype in terms of a medoid, which is the most representative point for a group of points, and can be applied to a wide range of data since it requires only a proximity measure for a pair of objects. While a centroid almost never corresponds to an actual data point, a medoid, by its definition, must be an actual data point.

In the K-means clustering technique, we first choose K initial centroids, the number of clusters desired. Each point in the data set is then assigned to the closest centroid, and each collection of points assigned to a centroid is a cluster. The centroid of each cluster is then updated based on the points assigned to the cluster. We iteratively assign points and update until convergence (no point changes clusters), or equivalently, until the centroids remain the same. For some combinations of proximity functions and types of centroids, K-means always converges to a solution; i.e., K-means reaches a state in which no points are shifting from one cluster to another, and hence, the centroids don't change. Because convergence tends to b asymptotic, the end condition may be set as a maximum change between iterations. Because of the possibility that the optimization results in a local minimum instead of a global minimum, errors may be maintained unless and until corrected. Therefore, a human assignment or reassignment of data points into classes, either as a constraint on the optimization, or as an initial condition, is possible.

To assign a point to the closest centroid, a proximity measure is required. Euclidean (L2) distance is often used for data points in Euclidean space, while cosine similarity may be more appropriate for documents. However, there may be several types of proximity measures that are appropriate for a given type of data. For example, Manhattan (L1) distance can be used for Euclidean data, while the Jaccard measure is often employed for documents. Usually, the similarity measures used for K-means are relatively simple since the algorithm repeatedly calculates the similarity of each point to each centroid, and thus complex distance functions incur computational complexity. The clustering may be computed as a statistical function, e.g., mean square error of the distance of each data point according to the distance function from the centroid. Note that the K-means may only find a local minimum, since the algorithm does not test each point for each possible centroid, and the starting presumptions may influence the outcome. The typical distance functions for documents include the Manhattan (L1) distance, Bregman divergence, Mahalanobis distance, squared Euclidean distance and cosine similarity.

An optimal clustering will be obtained as long as two initial centroids fall anywhere in a pair of clusters, since the centroids will redistribute themselves, one to each cluster. As the number of clusters increases, it is increasingly likely that at least one pair of clusters will have only one initial centroid, and because the pairs of clusters are further apart than clusters within a pair, the K-means algorithm will not redistribute the centroids between pairs of clusters, leading to a suboptimal local minimum. One effective approach is to take a sample of points and cluster them using a hierarchical clustering technique. K clusters are extracted from the hierarchical clustering, and the centroids of those clusters are used as the initial centroids. This approach often works well, but is practical only if the sample is relatively small, e.g., a few hundred to a few thousand (hierarchical clustering is expensive), and K is relatively small compared to the sample size. Other selection schemes are also available.

The space requirements for K-means are modest because only the data points and centroids are stored. Specifically, the storage required is $O((m+K)^n)$, where m is the number of points and n is the number of attributes. The time requirements for K-means are also modest-basically linear in the number of data points. In particular, the time required is $O(I \times K \times m \times n)$, where I is the number of iterations required for convergence. As mentioned, I is often small and can usually be safely bounded, as most changes typically occur in the first few iterations. Therefore, K-means is linear in m, the number of points, and is efficient as well as simple provided that K, the number of clusters, is significantly less than m.

Outliers can unduly influence the clusters, especially when a squared error criterion is used. However, in some clustering applications, the outliers should not be eliminated or discounted, as their appropriate inclusion may lead to important insights. In some cases, such as financial analysis, apparent outliers, e.g., unusually profitable investments, can be the most interesting points.

Hierarchical clustering techniques are a second important category of clustering methods. There are two basic approaches for generating a hierarchical clustering: Agglomerative and divisive. Agglomerative clustering merges close clusters in an initially high dimensionality space, while divisive splits large clusters. Agglomerative clustering relies upon a cluster distance, as opposed to an object distance. For example the distance between centroids or medioids of the clusters, the closest points in two clusters, the further points in two clusters, or some average distance metric. Ward's method measures the proximity between two clusters in terms of the increase in the sum of the squares of the errors that results from merging the two clusters.

Agglomerative Hierarchical Clustering refers to clustering techniques that produce a hierarchical clustering by starting with each point as a singleton cluster and then repeatedly merging the two closest clusters until a single, all-encompassing cluster remains. Agglomerative hierarchical clustering cannot be viewed as globally optimizing an objective function. Instead, agglomerative hierarchical clustering techniques use various criteria to decide locally, at each step, which clusters should be merged (or split for divisive approaches). This approach yields clustering algorithms that avoid the difficulty of attempting to solve a hard combinatorial optimization problem. Furthermore, such approaches do not have problems with local minima or difficulties in choosing initial points. Of course, the time complexity of $O(m^2 \log m)$ and the space complexity of $O(m^2)$ are prohibitive in many cases. Agglomerative hierarchical clustering algorithms tend to make good local decisions about combining two clusters since they can use information about the pair-wise similarity of all points. However, once a decision is made to merge two clusters, it cannot be undone at a later time. This approach prevents a local optimization criterion from becoming a global optimization criterion.

In supervised classification, the evaluation of the resulting classification model is an integral part of the process of developing a classification model. Being able to distinguish whether there is non-random structure in the data is an important aspect of cluster validation.

BIBLIOGRAPHY

Each of the following references is expressly incorporated herein by reference in its entirety:

M. S. Aldenderfer and R. K. Blashfield. Cluster Analysis. Sage Publications, Los Angeles, 1985.

M. R. Anderberg. Cluster Analysis for Applications. Academic Press, New York, December 1973.

M. Ankerst, M. M. Breunig, H.-P. Kriegel, and J. Sander. OPTICS: Ordering Points To Identify the Clustering Structure. In Proc. of 1999 ACM-SIGMOD Intl. Conf. on Management of Data, pages 49-60, Philadelphia, Pa., June 1999. ACM Press.

P. Arabie, L. Hubert, and G. D. Soete. An overview of combinatorial data analysis. In P. Arabie, L. Hubert, and G. D. Soete, editors, Clustering and Classification, pages 188-217. World Scientific, Singapore, January 1996.

G. Ball and D. Hall. A Clustering Technique for Summarizing Multivariate Data. Behavior Science, 12:153-155, March 1967.

A. Banerjee, S. Merugu, I. S. Dhillon, and J. Ghosh. Clustering with Bregman Divergences. In Proc. of the 2004 SIAM Intl. Conf. on Data Mining, pages 234-245, Lake Buena Vista, Fla., April 2004.

P. Berkhin. Survey Of Clustering Data Mining Techniques. Technical report, Accrue Software, San Jose, Calif., 2002.

D. Boley. Principal Direction Divisive Partitioning. Data Mining and Knowledge Discovery, 2(4):325-344, 1998.

P. S. Bradley and U. M. Fayyad. Refining Initial Points for K-Means Clustering. In Proc. of the 15th Intl. Conf. on Machine Learning, pages 91-99, Madison, Wis., July 1998. Morgan Kaufmann Publishers Inc.

CLUTO 2.1.1: Software for Clustering High-Dimensional Datasets. www.cs.umn.edu/~karypis, November 2003.

I. S. Dhillon, Y. Guan, and J. Kogan. Iterative Clustering of High Dimensional Text Data Augmented by Local Search. In Proc. of the 2002 IEEE Intl. Conf. on Data Mining, pages 131-138. IEEE Computer Society, 2002.

I. S. Dhillon and D. S. Modha. Concept Decompositions for Large Sparse Text Data Using Clustering. Machine Learning, 42(1/2):143-175, 2001.

R. O. Duda, P. E. Hart, and D. G. Stork. Pattern Classification. John Wiley & Sons, Inc., New York, second edition, 2001.

M. Ester, H.-P. Kriegel, J. Sander, M. Wimmer, and X. Xu. Incremental Clustering for Mining in a Data Warehousing Environment. In Proc. of the 24th VLDB Conf., pages 323-333, New York City, August 1998. Morgan Kaufmann.

M. Ester, H.-P. Kriegel, J. Sander, and X. Xu. A Density-Based Algorithm for Discovering Clusters in Large Spatial Databases with Noise. In Proc. of the 2nd Intl. Conf. on Knowledge Discovery and Data Mining, pages 226-231, Portland, Oreg., August 1996. AAAI Press.

B. S. Everitt, S. Landau, and M. Leese. Cluster Analysis. Arnold Publishers, London, fourth edition, May 2001.

D. Fisher. Iterative Optimization and Simplification of Hierarchical Clusterings. Journal of Artificial Intelligence Research, 4:147-179, 1996.

M. Halkidi, Y. Batistakis, and M. Vazirgiannis. Cluster validity methods: part I. SIGMOD Record (ACM Special Interest Group on Management of Data), 31(2):40-45, June 2002.

M. Halkidi, Y. Batistakis, and M. Vazirgiannis. Clustering validity checking methods: part II. SIGMOD Record (ACM Special Interest Group on Management of Data), 31 (3):19-27, September 2002.

G. Hamerly and C. Elkan. Alternatives to the k-means algorithm that find better clusterings. In Proc. of the 11th Intl. Conf. on Information and Knowledge Management, pages 600-607, McLean, Va., 2002. ACM Press.

J. Han, M. Kamber, and A. Tung. Spatial Clustering Methods in Data Mining: A review. In H. J. Miller and J. Han, editors, Geographic Data Mining and Knowledge Discovery, pages 188-217. Taylor and Francis, London, December 2001.

J. Hartigan. Clustering Algorithms. Wiley, New York, 1975.

T. Hastie, R. Tibshirani, and J. H. Friedman. The Elements of Statistical Learning: Data Mining, Inference, Prediction. Springer, New York, 2001.

A. K. Jain and R. C. Dubes. Algorithms for Clustering Data. Prentice Hall Advanced Reference Series. Prentice Hall, March 1988. www.cse.msu.edu/~jain/Clustering Jain Dubes.pdf.

A. K. Jain, M. N. Murty, and P. J. Flynn. Data clustering: A review. ACM Computing Surveys, 31(3):264-323, September 1999.

N. Jardine and R. Sibson. Mathematical Taxonomy. Wiley, New York, 1971.

G. Karypis, E.-H. Han, and V. Kumar. Multilevel Refinement for Hierarchical Clustering. Technical Report TR 99-020, University of Minnesota, Minneapolis, Minn., 1999.

L. Kaufman and P. J. Rousseeuw. Finding Groups in Data: An Introduction to Cluster Analysis. Wiley Series in Probability and Statistics. John Wiley and Sons, New York, November 1990.

J. M. Kleinberg. An Impossibility Theorem for Clustering. In Proc. of the 16th Annual Conf. on Neural Information Processing Systems, Dec. 9-14, 2002.

B. Larsen and C. Aone. Fast and Effective Text Mining Using Linear-Time Document Clustering. In Proc. of the 5th Intl. Conf. on Knowledge Discovery and Data Mining, pages 16-22, San Diego, Calif., 1999. ACM Press.

J. MacQueen. Some methods for classification and analysis of multivariate observations. In Proc. of the 5th Berkeley Symp. on Mathematical Statistics and Probability, pages 281-297. University of California Press, 1967.

G. W. Milligan. Clustering Validation: Results and Implications for Applied Analyses. In P. Arabie, L. Hubert, and G. D. Soete, editors, Clustering and Classification, pages 345-375. World Scientific, Singapore, January 1996.

B. Mirkin. Mathematical Classification and Clustering, volume 11 of Nonconvex Optimization and Its Applications. Kluwer Academic Publishers, August 1996.

T. Mitchell. Machine Learning. McGraw-Hill, Boston, Mass., 1997.

F. Murtagh. Multidimensional Clustering Algorithms. Physica-Verlag, Heidelberg and Vienna, 1985.

D. Pelleg and A. W. Moore. X-means: Extending K-means with Efficient Estimation of the Number of Clusters. In Proc. of the 17th Intl. Conf. on Machine Learning, pages 727-734. Morgan Kaufmann, San Francisco, Calif., 2000.

C. Romesburg. Cluster Analysis for Researchers. Life Time Learning, Belmont, C A, 1984.

J. Sander, M. Ester, H.-P. Kriegel, and X. Xu. Density-Based Clustering in Spatial Databases: The Algorithm GDB-SCAN and its Applications. Data Mining and Knowledge Discovery, 2(2):169-194, 1998.

S. M. Savaresi and D. Boley. A comparative analysis on the bisecting K-means and the PDDP clustering algorithms. Intelligent Data Analysis, 8(4):345-362, 2004.

P. H. A. Sneath and R. R. Sokal. Numerical Taxonomy. Freeman, San Francisco, 1971.

H. Späth. Cluster Analysis Algorithms for Data Reduction and Classification of Objects, volume 4 of Computers and Their Application. Ellis Horwood Publishers, Chichester, 1980. ISBN 0-85312-141-9.

M. Steinbach, G. Karypis, and V. Kumar. A Comparison of Document Clustering Techniques. In Proc. of KDD Workshop on Text Mining, Proc. of the 6th Intl. Conf. on Knowledge Discovery and Data Mining, Boston, Mass., August 2000.

C. T. Zahn. Graph-Theoretical Methods for Detecting and Describing Gestalt Clusters. IEEE Transactions on Computers, C-20(1):68-86, January 1971.

B. Zhang, M. Hsu, and U. Dayal. K-Harmonic Means—A Data Clustering Algorithm. Technical Report HPL-1999-124, Hewlett Packard Laboratories, Oct. 29, 1999.

Y. Zhao and G. Karypis. Empirical and theoretical comparisons of selected criterion functions for document clustering. Machine Learning, 55(3):311-331, 2004.

Anderberg, M. R. (1973). *Cluster Analysis for Applications*. Academic Press, New York.

Anderson, E. (1957). A semi-graphical method for the analysis of complex problems. *Proc. Nat. Acad. Sci. USA* 43 923-927.

Anderson, T. W. (1958). *An Introduction to Multivariate Statistical Analysis*. Wiley, New York.

Anderson, T. W., and Bahadur, R. R. (1962). classification into two multivariate normal distributions with different covariance matrices. *Ann. Math. Statist.* 33 420-431.

Andrews, D. F. (1972). Plots of high-dimensional data. *Biometrics* 28 125-136.

Arabie, P. (1977). clustering representations of group overlap. J. *Math. Soc.* 5 112-128.

Arabie, P. and Carroll, J. D. (1980). MAPCLUS: A mathematical programming approach to fitting to ADCLUS model. *Psychometrika* 45 211-235.

Art, D., Gnanadesikan, R., and Kettenring, J. R. (1982). Data-based metrics for cluster analysis. *Utilitas Mathematica* 31A 75-99.

Asimov, D. (1985). The grand tour. *SLAM J. Sci. Statist. Corn-put.* 6 128-143.

Baker, F. B. (1974). Stability of two hierarchical grouping techniques, Case I: Sensitivity to data errors. J. *Amer. Statist. Assoc.* 69 440-445.

Becker, P. (1968). *Recognitions of Patterns*. Polyteknisk, Copenhagen.

Bell, P. A. and Korey, J. L. (1975). QUICLSTR: A FOR 'TRAN program for hierarchical cluster analysis with a large number of subjects. *Behavioral Research Methods and Instrumentation* 7 575.

Binder, D. A. (1978). Comment on 'Estimating mixtures of normal distributions and switching regressions'. j *Amer. Statist. Assoc.* 73 746-747.

Blashfield, R. K., Aldenderfer, M. S. and Morey, L. C. (1982). cluster analysis literature on validation. In *Classifying Social Data*. (H. Hudson, ed.) 167-176. Jossey-Bass, San Francisco.

Bock, H. H. (1985). On significance tests in cluster analysis. J. *Classification* 2 77-108.

Brieman, L., Friedman, J. H., Olshen, R. A., and Stone, C. J. (1984). *Classification and Regression Trees*. Wadsworth, Belmont, Calif.

Breiman, L. Meisel, W. S., and Purcell, E. (1977). Variable kernel estimates of multivariate densities and their calibration. *Technometrics* 19 135-144.

Broadbent, S. R. and Hammersley, J. M. (1957). Percolation Processes, I: Crystals and Mazes. *Proc. Cambridge Philos. Soc.* 53 629-641

Buja, A., Hurify, C. and Mcdonald, J. A. (1986). A data viewer for multivariate data. *Computer Science and Statistics: Proceedings of the* 18th Symposium on the Interface 171-174.

Cacoullos, T. (1966). Estimation of a multivariate density. *Ann. Math. Statist.* 18 179-189.

Chen, H., Gnanadesikan, R., and Kettenring, J. R. (1974). Statistical methods for grouping corporations. *Sankhya B* 36 1-28.

Chernoff, H. (1972). The selection of effective attributes for deciding between hypotheses using linear discriminant functions. In *Frontiers of Pattern Recognition*. (S. Watanabe, ed.) 55-60. Academic Press, New York.

Chernoff, H. (1973a). Some measures for discriminating between normal multivariate distributions with unequal covariance matrices. In *Multivariate Analysis Ill*. (P. R. Krishnaiah, ed.) 337-344. Academic Press, New York.

Chernoff, H. (1973b). The use of faces to represent points in k-dimensional space graphically. J *Amer. Statist. Assoc.* 68 361-368.

Clunies-Ross, C. W. and Riffenburgh, R. H. (1960). Geometry and linear discrimination. *Biometrika* 47 185-189.

Cormack, R. M. (1971). A review of classification (with discussion). J. *Roy. Statist. Soc.* A 134 321-367.

Cornfield, J. (1962). Joint dependence of rish of coronary heart disease on serum cholesterol and systolic blood pressure: a discriminant function analysis. *Federal Proceedings* 21 58-61.

Cover, T. M. (1968). Estimation by the nearest neighbor rule. *IEEE Transactions Information Theory IT-*14 50-55.

Cover, T. M. and Hart, P. E. (1967). Nearest neighbor pattern classification. *IEEE Transactions, Information Theory IT-*13 21-27.

Dallal, G. E. (1975) A user's guide to J. A. Hartigan's clustering algorithms. (unpublished manuscript) Yale University.

Day, N. E. (1969). Estimating the components of a mixture of normal distributions. *Biometrika* 56 463-474.

DAY, N. E., and KERRIDGE, D. F., (1967). A general maximum likelihood discriminant. *Biometrics* 23 313-323. 94

Defays, D. (1977). An efficient algorithm for a complete link method. *Computer Journal* 20 364-366.

Dick, N. P. and Bowden, D. C. (1973). Maximum likelihood estimation for mixtures of two normal distributions. *Biometrics* 29 781-790

Dixon, W. J. (ed.) (1981). *BMDP Statistical Software*. University of California Press, Berkeley.

Donoho, A. W., Donoho, D. L. and Gasko, M. (1985). MacSpin graphical data analysis software. D2 Software, Austin.

Duda, R. O. and Hart, P. E. (1973). *Pattern Classification and Scene Analysis*. Wiley, New York.

Edmonston, B. (1985). MICRO-CLUSTER: Cluster analysis software for microcomputers. *Journal of Classification* 2 127-130.

Efron, B. (1975). The efficiency of logistic regression compared to normal discriminant analysis. *j Amer. Statist. Assoc.* 70 892-898.

Efron, B. (1979). Bootstrap methods: Another look at the jack-knife. *Ann. Statist.* 7 1-26.

Efron, B. (1982). *The Jackknife, The Bootstrap, and Other Resampling Plans*, SIAM NSF-CBMS, Monograph #38.

Efron, B. (1983). Estimating the error rate of a prediction rule: Improvements on cross-validation. *J. Amer. Statist. Assoc.* 78 316-331.

Everitt, B. (1980). *Cluster Analysis*. 2nd ed. Halsted, N.Y.

Everitt, B. S. and Hand, D. J. (1981). *Finite Mixture Distributions*. Chapman and Hall, London.

Farver, T. B. and Dunn, O. J. (1979). Stepwise variable selection in classification problems. *Biom. J.* 21 145-153.

Fisher, R. A. (1936). The use of multiple measurements in taxonomic problems. *Ann. Eugenics* 7(part 2) 179-188.

Fisherkeller, M. A., Friedman, J. H., and Tukey, J. W. (1974). Prim-9: An interactive multidimensional data display and analysis system. SLAC-Pub. 1408, Stanford Linear Accelerator Center, Stanford, Calif.

Fitch, W. M. and Marcouash, E. (1967). Construction of phylogenetic trees. *Science* 155 279-284.

Fix, E. and Hodges, J. (1951). Discriminatory analysis, nonparametric discrimination: consistency properties. Technical Report. Randolph Field, Tex.: USAF School of Aviation Medicine.

Fowixes, E. B. (1987). Some diagnostics for binary logistic regression via smoothing. *Biometrika* to appear.

Fowlkes, E. B., Gnanadesikan, R. and Kettenring, J. R. (1987). Variable selection in clustering and other contexts. In *Design, Data, and Analysis, by Some Friends of Cuthbert Daniel* (C. L. Mallows, ed.). Wiley, New York, to appear.

Fowlkes, E. B. and Mallows, C. L. (1983). A method for comparing two hierarchical clusterings (with discussion). *J Amer. Statist. Assoc.* 78 553-583.

FRIEDMAN, H. P. and RUBIN, J. (1967). On some invariant criteria for grouping data. *Journal of American Statistical Association* 62 1159-1178.

Friedman, J. H. and Tukey, J. W. (1974). A projection pursuit algorithm for exploratory data analysis. *IEEE Trans. Comput.* C-23 881-889.

Gnanadesikan, R. (1977). *Methods for Statistical Data Analysis of Multivariate Observations*. Wiley, New York.

Gnanadesikan, R. and Kettenring, J. R. (1984). A pragmatic review of multivariate methods in applications. In *Statistics: An Appraisal*. (H. A. David and H. T. David, eds.).

Gnanadesikan, R., Kettenring, J. R., and Landwehr, J. M. (1977). Interpreting and assessing the results of cluster analyses. *Bull Int. Statis. Inst.* 47 451-463.

Gnanadesikan, R., Kettenring, J. R. and Landwehr, J. M. (1982). Projection plots for displaying clusters. In *Statistics and Probability: Essays in Honor of C. R. Rao*. (G. Kallianpur, P. R. Krishnaiah and J. K. Ghosh, eds.) 281-294. North-Holland, Amsterdam.

Goldman, L., Weinberg, M., Weisberg, M., Olshen, R., Cook, F., Sargent, R. K., Lamas, G. A., Dennis, C., Deckelbam, L., Fineberg, H., Stiratelu, R. and the Medical Housestaffs At Yale-New Haven Hospital and Brigham and Women's Hospital (1982). A computer-derived protocol to aid in the diagnosis of emergency room patients with acute chest pain. The *New England Journal of Medicine* 307 588-596.

Gong, G. (1982). Cross-validation, the jackknife, and the bootstrap: excess error estimation in forward logistic regression. Ph.D. dissertation. Stanford University Technical Report No. 80. Department of Statistics.

Gordon, L. and Olshen, R. A. (1978). Asymptotically efficient solutions to the classification problem. *Ann. Statist.* 6 515-533.

Gordon, L. and Olshen, R. A. (1980). Consistent non-parametric regression from recursive partitioning schemes. *J. Mult. Anal.* 10 611-627.

Gordon, L. and Olshen, R. A. (1984). Almost surely consistent nonparametric regression from recursive partitioning schemes. *J. Mult. Anal.* 15 147-163.

Gower, J. C. and Ross, G. J. S. (1969). Minimum spanning trees and single linkage cluster analysis. *Appl. Statist.* 18 54-65.

Gray, J. B. and Ling, R. F. (1984). K-clustering as a detection tool for influential subsets regression (with discussion). *Technometrics* 26 305-330.

Haff, L. R. (1986). On linear log-odds and estimation of discriminant coefficients. *Commun. Statist.—Theor. Meth.* 15 2131-2144.

Hall, D. J. and Khanna, D. (1977). The ISODATA method of computation for relative perception of similarities and differences in complex and real data. In *Statistical Methods for Digital Computers* (Vol. 3). (K Enslein, A. Ralston, and H. W. Wilf, eds.) New York: John Wiley.

Hand, D. J. (1981). *Discrimination and Classification*. Wiley, New York.

Hartigan, J. A. (1967). Representation of similarity matrices by trees. *J. Amer. Statist. Assoc.* 62 1140-1158.

Hartigan, J. A. (1975). *Clustering Algorithms*. Wiley, New York.

Hartigan, J. A. (1977). Distribution problems in clustering. In *Classification and Clustering* (J. Van Ryzin, ed.) 45-71. Academic Press, New York.

Hartigan, J. A. (1978). Asymptotic distributions for clustering criteria. *Ann. Statist.* 6 117-131.

Hartigan, J. A. (1981). Consistency of single linkage for high density clusters. *J. Amer. Statist Assoc.* 76 388-394.

Hartigan, J. A. and Hartigan, P. M. (1985). The dip test of multimodality. *Ann. of Statist.* 13 70-84.

Hermans, J., Habbema, J., and Schaefer, R. (1982). The ALLOC8O package for discriminant analysis, *Stat. Software Newsletter,* 8 15-20.

Hodson, F. R., Sneath, P. H. A. and Doran, J. E. (1966). Some experiments in the numerical analysis of archaeological data. *Biometrika* 53 311-324.

Hosmer, D. W. (1973). A comparison of iterative maximum likelihood estimates of the parameters of a mixture of two normal distributions under three different typos of sample. *Biometrics* 29 761-770.

Huber, P. J. (1985). Projection pursuit (with discussion). *Ann. Statist.* 6 701-726. International Mathematical and Statistical Library (1977). Reference manual library 1, ed. 6. Vol. 1. Houston.

James, W. and Stein, C. (1961). Estimation with quadratic loss. *Proc. Fourth Berkeley Symp. Math. Statist. Prob.* 1 311-319.

Jambu, M. and Lebeaux, M. O. (1983). *Cluster Analysis and Data Analysis.* North-Holland Publishing Company, Amsterdam.

Jardine, C. J., Jardine, N. and Sibson, R. (1967). The structure and construction of taxonomic hierarchies. *Math. Biosci.* 1 173-179.

Jennrich, R. I. (1962). *Linear Discrimination in the Case of Unequal Covariance Matrices.* Unpublished manuscript.

Jennrich, R. and Moore, R. H. (1975). Maximum likelihood estimation by means of nonlinear least squares. *Proceedings of the Statistical Computing Section*, American Statistical Association, 57-65.

Johnson, S. C. (1967). Hierarchical clustering schemes. *Psychometrika* 32241-254.

Kettenring, J. R., Rogers, W. H., Smith, M. E., and Warner, J. L. (1976). Cluster analysis applied to the validation of course objectives. *J. Educ. Statist.* 1 39-57.

Kleiner, B. and Hartigan, J. A. (1981). Representing points in many dimensions by trees and castles (with discussion). *j Amer. Statist. Assoc.* 76260-276.

Lachenbruch P. A. (1975) *Discriminant Analysis.* Hafner Press, New York.

Lachenbruch, P. A. (1982). Robustness of discriminant flirictions. *SUGI-SAS Group Proceedings* 7626-632.

Landwehr J. M., Pregibon, D., and Shoemaker, K C. (1984). Graphical methods for assessing logistic regression models (with discussion). *J Amer. Statist. Assoc.* 7961-83.

Lennington, R. K. and Rossbach, M. E. (1978). CLASSY: An adaptive maximum likelihood clustering algorithm. Paper presented at 1978 meeting of the Classification Society.

Levisohn, J. R. and Funk, S. G. (1974). CLUSTER: A hierarchical clustering program for large data sets (n>100). Research Memo #40, Thurstone Psychometric Laboratory, University of North Carolina.

Ling, R. F. (1973). A probability theory of cluster analysis. *J. Amer. Statist. Assoc.* 68159-169.

Macqueen, J. (1967). Some methods for classification and analysis of multivariate observations. *Proc. Fifth Berkeley Symp. Math. Statist. Prob.* 1281-297.

Marks, S. and Dunn, O. J. (1974). Discriminant functions when covariance matrices are unequal. *J. Amer. Statist. Assoc.* 69 555-559.

Mccullagh, P. and Nelder, J. A. (1983). *Generalized Linear Models.* Chapman and Hall, London.

Mckay, R. J. (1978). A graphical aid to selection of variables in two-group discriminant analysis. *Appl. Statist.* 27259-263.

Mckay, R. J. and Campbell, N. A. (1982a). Variable selection techniques in discriminant analysis. 1. Description. *Br. J. Math. Stat. Psychol.* 351-29.

Mckay, R. J. and Campbell, N. A. (1982b). Variable selection techniques in discriminant analysis. II. Allocation. *Br. J. Math. Stat. Psychol.* 353041.

Michener, C. D. and Sokal R. R. (1957). A quantitative approach to a problem in classification. *Evolution ii* 130-162.

Mojena, R. (1977). Hierarchical grouping methods and stopping rules—An evaluation. *Computer Journal* 20359-363.

Mojena, R. and Wishart, D. (1980). Stopping rules for Ward's clustering method. *Proceedings of COMPSTAT.* Physica Verlag 426-432.

Morgan, J. N. and Sonquist, J. A. (1963). Problems in the analysis of survey data, and a proposal. *J. Amer. Statist. Assoc.* 58415-435.

Nelder, J. A. and Wedderburn, R. W. M. (1972). Generalized linear models. *J Roy. Statist. Soc. A* 135 370-384.

Morgan, J. N. and Messenger, R. C. (1973). THMD: a sequential search program for the analysis of nominal scale dependent variables. Institute for Social Research, U of Michigan, Ann Arbor.

Olshen, R. A., Gilpin, E., Henning, H. Lewinter, M., Collins, D., and Ross., J., Jr. (1985). Twelve month prognosis following myocardial infarction: classification trees, logistic regression, and stepwise linear discrimination. *Proceedings of the Berkeley Conference in Honor of Jerzy Neyman and Jack Kiefer.* (L. LeCam and R. Olshen, eds.) 1 245-267. Wadsworth Advanced Books and Software, Monterey, Calif. and the Institute of Mathematical Statistics, Hayward, Calif.

Pollard, D. (1982). A central limit theorem for k-means clustering. *Ann. Prob.* 10919-926.

Pregibon, D. (1981). Logistic regression diagnostics. *Ann. Statist.* 9 705-724.

Rabiner, L. R., Levinson, S. E., Rosenberg, A. E. and Wilpon, J. G. (1979). Speaker independent recognition of isolated words using clustering techniques. IEEE Trans. Accoust. Speech Signal Process. 27336-349.

Rao, C. R. (1948). The utilization of multiple measurements in problems of biological classification. *J. Roy. Statist. Soc. Ser. B* 10159-203.

Rao, C. R. (1952). *Advanced Statistical Methods in Biometric Research.* Wiley, New York.

Rao, C. R. (1960). Multivariate analysis: an indispensable statistical aid in applied research. *Sankhya* 22317-338.

Rao, C. R. (1962). Use of discriminant and allied functions in multivariate analysis. *Sankhya A*24 149-154.

Rao, C. R. (1965). *Linear Statistical Inference and Its Applications.* Wiley, New York.

Riffenburgh, R. H. and Clunies-Ross, C. W. (1960). Linear discriminant analysis. *Pacific Science* 14 251-256.

Rohlf, F. J. (1977). Computational efficacy of agglomerative clustering algorithms. Technical Report RC-6831. IBM Watson Research Center Rohlf, F. J. (1982). Single-link clustering algorithms. In *Handbook of Statistics: Vol.* 2, (P. R. Krishnaiah and L. N. Kanal, eds.) 267-284. North-Holland Publishing Company, Amsterdam.

Rotman, S. R., Fisher, A. D., and Staelin, D. H. (1981). Analysis of multiple-angle microwave observations of snow and ice using cluster analysis techniques. *J. Glaciology* 27 89-97.

Ryan, T., Joiner, B., and Ryan, B. (1982). *Minitab Reference Manual.* Duxbury Press, Boston.

SAS Institute, Inc. (1985). SAS User's Guide: Statistics, Version S Edition. Sas Institute, Inc., Cary, N.C.

Seber, G. A. F. (1984). *Multivariate Observations.* Wiley, New York.

Shepard, R. N. and Arabie, P. (1979). Additive clustering: representation of similarities as combinations of discrete overlapping properties. *Psychological Review* 8687-123.

Shibata, R. (1981). An optimal selection of regression variables. *Biometrika* 6845-54.

Sibson, R. (1973). SLINK: An optimally efficient algorithm for single-link cluster methods. *Computer Journal* 1630-34.

Siegel, J. H., Goldwyn, R. M., and Friedman, H. P. (1971). Pattern and process in the evolution of human septic shock. *Surgery* 70232-245.

Silverman, B. W. (1986). *Density Estimation for Statistics and Data Analysis.* Chapman and Hall, London.

Smythe, R. T. and Wierman, J. C. (1978). First passage percolation on the square lattice. *Lecture Notes in Mathematics* 671. Springer-Verlag, Berlin.

Sneath, P. H. A. and Sokal, R. R. (1973). *Numerical Taxonomy*. Freeman, San Francisco.

Sokal, R. R. (1974). Classification: purposes, principles, progress, prospects. *Science* 185 1115-1123.

SPSS, INC. (1986). SPSSX (a computer program). McGraw-Hill, New York.

Stein, C. (1956). Inadmissibility of the usual estimator for the mean of a multivariate normal distribution. *Third Berkeley Symp. Math. Statist. Prob.* 1 197-206.

Stone, C. J. (1977). Consistent nonparametric regression (with discussion). *Ann. Statist.* 5595-645.

Stone, M. (1977). Cross-validation: a review. *Math. Operationforsch. Statist. Ser. Statist.* 9 127-139.

Tarter, M. and Kronmal, R. (1970). On multivariate density estimates based on orthogonal expansions. *Ann. Math. Statist.* 4 718-722.

Toussaint, G. T. (1974). Bibliography on estimation of misclassification. *IEEE Transactions on Information Theory* IT-20 472A79.

Thuett, J., Cornfield, J. and Kannel, W. (1967). A multivariate analysis of the risk of coronary heart disease in Framingham. *J of Chronic Diseases* 20511-524.

Thyon, R. C. (1939). *Cluster Analysis*. edwards Brothers, Ann Arbor, Mich.

Vapnik, V. N. and Chervonenkis, A. YA. (1971). On the uniform convergence of relative frequencies of events to their probabilities. *Theor. Prob. Appl.* 16264-280.

Vapnik, V. N. and Chervonenkis, A. YA. (1974). *Theory of Pattern Recognition* (in Russian). Nauka, Moscow.

VELDMAN, D. J. (1967). *FORTRAN Programming for the Behavioral Sciences*. Holt, Rinehart and Winston, N.Y.

Vrijenhoek, R. C., Douglas, M. E., and Meffe, G. K.-(1985). Conservation genetics of endangered fish populations in Arizona. *Science* 229 100-402.

Wald, A. (1944). On a statistical problem arising in the classification of an individual into one of two groups. *Ann. Math. Statist.* 15145-162.

Walker, S. B. and Duncan, D. B. (1967). Estimation of the probability of an event as a function of several independent variables. *Biometrika* 54 167-179.

Wishart, D. (1969). Mode Analysis: A generalization of nearest neighbor which reduces chaining effects in *Numerical Taxonomy*, (A. J. Cole, ed.), Academic Press, London.

Wolfe, J. H. (1970). Pattern clustering by multivariate mixture analysis. *Multivariate Behavioral Research* S 329-350.

Wolfe, J. H. (1971). A Monte-Carlo study of the sampling distribution of the likelihood ratio for mixtures of multinormal distributions. *Research Memorandum* 72-2, Naval Personnel and Research Training Laboratory, San Diego.

H Sundaram, Y R Lin . . . -Signal Processing . . . , 2012-ieeexplore.ieee.org; Understanding Community Dynamics in Online Social Networks: A multidisciplinary R Xu, J Xu . . . -2012-ieeexplore.ieee.org; A Comparison Study of Validity Indices on Swarm-Intelligence-Based Clustering C Tu, S Jiao . . . -2012-Taylor & Francis; Comparison of clustering algorithms on generalized propensity score in observational studies: a simulation study Y Li . . . -Physics Procedia, 2012-Elsevier; A Clustering Method Based on K-Means Algorithm C C Chang . . . -Pattern Recognition, 2012-Elsevier; Semi-supervised clustering with discriminative random fields B Wang . . . -Procedia Engineering, 2012-Elsevier; Deceptive Financial Reporting Detection: A Hierarchical Clustering Approach Based on Linguistic Features Z Volkovich, D Toledano-Kitai . . . -Journal of Global . . . , 2012-Springer; Self-learning K-means clustering: a global optimization approach S Gulten . . . -2012-papers.ssrn.com; Two-Stage Portfolio Optimization with Higher-Order Conditional Measures of Risk P Sharma, S Salapaka . . . -Automatic Control, IEEE . . . , 2012-ieeexplore.ieee.org; Entropy-based framework for dynamic coverage and clustering problems X LOU, J L I . . . -Journal of Computational Information Systems, 2012-jofcis.com; Improved Fuzzy C-means Clustering Algorithm Based on Cluster Density Z Volkovich, G W Weber, R Avros . . . -International Journal of . . . , 2012-Inderscience; On an adjacency cluster merit approach C Beck, S Salapaka, P Sharma . . . -Distributed Decision Making and . . . , 2012-Springer; Dynamic Coverage and Clustering: A Maximum Entropy Approach K Lee . . . -Software Engineering Research, Management and . . . , 2012-Springer; A Market-Driven Product Line Scoping M Vlachos . . . -Information Visualization, 2012-ivi.sagepub.com; Recommendation and visualization of similar movies using minimum spanning dendrograms D C Guimarães Pedronette . . . -Information Sciences, 2012-Elsevier; Exploiting pairwise recommendation and clustering strategies for image re-ranking J Wang, S Wu . . . -International journal of computational . . . , 2012-dro.deakin.edu.au; Clustering with instance and attribute level side information C Schifanella, M L Sapino . . . -Journal of Intelligent Information . . . , 2012-Springer; On context-aware co-clustering with metadata support S Y Bhat . . . -Proceedings of the 2nd International Conference . . . , 2012-dl.acm.org; A density-based approach for mining overlapping communities from social network interactions B N Devi, Y R Devi, B P Rani . . . -Procedia Engineering, 2012-Elsevier; Design and Implementation of Web Usage Mining Intelligent System in the Field of e-commerce G Navarro-Arribas . . . -Information Fusion, 2012-Elsevier; Information fusion in data privacy: A survey A B Dragut-Methodology and Computing in Applied Probability, 2012-Springer; Stock Data Clustering and Multi-scale Trend Detection H Cheng, Y Zhou, X Huang . . . -Data Mining and Knowledge . . . , 2012-Springer; Clustering large attributed information networks: an efficient incremental computing approach K Treerattanapitak . . . -Journal of Computer Science and . . . , 2012-Springer; Exponential Fuzzy C-Means for Collaborative Filtering Y H Chen-Journal of Computational Biology, 2012-online.liebertpub.com; The k Partition-Distance Problem R Loohach . . . -mairec.org; AN INSIGHT OVERVIEW OF ISSUES AND CHALLENGES ASSOCIATED WITH CLUSTERING ALGORITHMS A Gulhane, P L Paikrao . . . -International Journal of Soft Computing-ijsce.org; A Review of Image Data Clustering Techniques B Auffarth-csc.kth.se; A Genetic Algorithm for Clustering with Biased Mutation Operator A Jayasimhan . . . -research.ijais.org; Anomaly Detection using a Clustering Technique T S Madhulatha-Arxiv preprint arXiv:1205.1117, 2012-arxiv.org; An Overview on Clustering Methods D Boley . . . -matrix-users.cs.cf.ac.uk; A General Unsupervised Clustering Tool for Unstructured Data B. Santhosh kumar, V. Vijayaganth, Data Clustering Using K-Means Algorithm For High Dimensional Data, International Journal of Advanced Research In Technology (ijart.org); 2(1)22-32, February 2012

G Peters . . . -Wiley Interdisciplinary Reviews: Data Mining and . . . -Wiley Online Library; Dynamic clustering with soft computing B H Babu, N S Chandra . . . -interscience.in; Clustering Algorithms For High Dimensional Data—A Survey Of Issues And Existing Approaches B A Tidke, R G Mehta . . . -ijesat.com; A Novel Approach For High Dimensional Data Clustering T Naresh, G R Naidu . . . -ijera.com; Learning Subject Areas by Using Unsupervised Observation of Most Informative Terms in Text Databases J F Ehmke-Integration of Information and Optimization Models for . . . , 2012-Springer; Knowledge Discovery and Data Mining V Ilango, R Subramanian . . . -European . . . , 2012-europeanjournalofscientificresearch; A Five Step Procedure for Outlier Analysis in Data Mining Z Wang, X Sun . . . -red.pe.org.pl; Efficient Kernel Discriminative Geometry Preserving Projection for Document Classification S A Ríos, R A Silva . . . - . . . of the 4th International Workshop on . . . , 2012-dl.acm.org; A dissimilarity measure for automate moderation in online social networks A Roshchina, J Cardiff . . . -lrec-conf.org; Evaluating the Similarity Estimator Component of the TWIN Personality-based Recommender System P Richhariya . . . -International Journal of Computer . . . , 2012-research.ijcaonline.org; A Survey on Financial Fraud Detection Methodologies R Salman-2012-digarchive.library.vcu.edu; Contributions To K-Means Clustering And Regression Via Classification Algorithms F Stahl . . . -Wiley Interdisciplinary Reviews: Data . . . , 2012-Wiley Online Library; An overview of the use of neural networks for data mining tasks T Schlüter . . . -Proceedings of the 27th Annual ACM . . . , 2012-dl.acm.org; Hidden markov model-based time series prediction using motifs for detecting inter-time-serial correlations G Tilak, T Szell, R Chicheportiche . . . -Arxiv preprint arXiv: . . . , 2012-arxiv.org; Study of statistical correlations in intraday and daily financial return time series R Ghaemi, M N Sulaiman, H Ibrahim . . . -Memetic Computing, 2012-Springer; A novel fuzzy C-means algorithm to generate diverse and desirable cluster solutions used by genetic-based clustering ensemble algorithms P Zuccolotto-AStA Advances in Statistical Analysis, 2012-Springer; Principal component analysis with interval imputed missing values S Martínez, A Valls . . . -Knowledge-Based Systems, 2012-Elsevier; Semantically-grounded construction of centroids for datasets with textual attributes C N Vasconcelos, V Jardim, A Sá. . . -iris.sel.eesc.usp.br; Photo Tagging by Collection-Aware People Recognition R Cai, L Zhang . . . -US Patent 2012/0125178 (2012); Scalable Music Recommendation By Search K C L Liu-cc.gatech.edu; Vista: Looking Into the Clusters in Very Large Multidimensional Datasets Y Bu, B Howe, M Balazinska . . . -The VLDB Journal-The . . . , 2012-dl.acm.org; The HaLoop approach to large-scale iterative data analysis U C A Sironi-unige.ch; Bond Trading, Market Anomalies And Neural Networks: An Analysis With Kohonen Nets M Kruliš , T Skopal, J Lokoč . . . -Distributed and Parallel . . . , 2012-Springer; Combining CPU and GPU architectures for fast similarity search J Derrac, I Triguero, S García . . . -IEEE transactions on . . . , 2012-ieeexplore.ieee.org; Integrating Instance Selection, Instance Weighting, and Feature Weighting for Nearest Neighbor Classifiers by Coevolutionary Algorithms.

R Baraglia, P Dazzi, M Mordacchini . . . -Journal of Computer and . . . , 2012-Elsevier; A Peer-to-Peer recommender system for self-emerging user communities based on Gossip overlays J Gao, W Hu, Z Zhang . . . - . . . in Knowledge Discovery and Data Mining, 2012-Springer; Unsupervised Ensemble Learning for Mining Top-n Outliers H T Zheng . . . -Expert Systems with Applications, 2012-Elsevier; Towards Group Behavioral Reason Mining L F Robinson-cis.jhu.edu; Detecting Time-dependent Structure in Network Data via a new Class of Latent Process Models H S Le, Z Bar-Joseph, C Langmead, R Rosenfeld . . . -cs.cmu.edu; Probabilistic models for collecting, analyzing and modeling expression data D Yang-2012-wpi.edu; Mining and Managing Neighbor-Based Patterns in Data Streams C Fournier . . . -Arxiv preprint arXiv:1204.2847, 2012-arxiv.org; Segmentation similarity and agreement C H Wan, L H Lee, R Rajkumar . . . -Expert Systems with Applications, 2012-Elsevier; A hybrid text classification approach with low dependency on parameter by integrating K-nearest neighbor and support vector machine H C Wu, R W P Luk, K F Wong . . . -Information Processing & . . . , 2012-Elsevier; A split-list approach for relevance feedback in information retrieval V J Hodge, T Jackson . . . -www-users.cs.york.ac.uk; Intelligent Decision Support using Pattern Matching H Le Capitaine-Fuzzy Systems, IEEE Transactions on, 2012-ieeexplore.ieee.org; A relevance-based learning model of fuzzy similarity measures K Rybina-rn.inf.tu-dresden.de; Sentiment analysis of contexts around query terms in documents T F de Máster-2012-ir.ii.uam.es; Novelty and Diversity Enhancement and Evaluation in Recommender Systems B Mianowska . . . -Multimedia Tools and Applications, 2012-Springer; Tuning user profiles based on analyzing dynamic preference in document retrieval systems M Drosou . . . -2012-cs.uoi.gr; Dynamic Diversification of Continuous Data G Ganu, Y Kakodkar . . . -Information Systems, 2012-Elsevier; Improving the quality of predictions using textual information in online user reviews E Carrizosa . . . -Computers & Operations Research, 2012-Elsevier; Supervised classification and mathematical optimization X Zhou-2012-gradworks.umi.com; Learning functions on unknown manifolds K Kitto . . . -per.marine.csiro.au; Attitudes, Ideologies And Self-Organisation: Information Load Minimisation In Multi-Agent Decision Making R Pivovarov . . . -Journal of Biomedical Informatics, 2012-Elsevier; A hybrid knowledge-based and data-driven approach to identifying semantically similar concepts K M Fouad, A R Khalifa, N M Nagdy . . . -2012-ijcsi.org; Web-based Semantic and Personalized Information Retrieval Semantic and Personalized Information Retrieval Semantic and Personalized Information . . .

A P Streib-2012-aco.gatech.edu; Markov Chains At The Interface Of Combinatorics, Computing, And Statistical Physics I T Christou, G Gekas . . . -International Journal of Machine Learning and . . . -Springer; A classifier ensemble approach to the TV-viewer profile adaptation problem J Joenväärä, R Kosowski . . . -2012-papers.ssrn.com; Revisiting 'Stylized Facts' About Hedge Funds-Insights from a Novel Aggregation of the Main Hedge Fund Databases I Abraham, S Chechik, D Kempe . . . -Arxiv preprint arXiv: . . . , 2012-arxiv.org; Low-distortion Inference of Latent Similarities from a Multiplex Social Network E Lloret, A Balahur, J M Gómez, A Montoyo . . . -Journal of Intelligent . . . , 2012-Springer; Towards a unified framework for opinion retrieval, mining and summarization Y Su . . . -International Journal of Computer Vision, 2012-Springer; Improving Image Classification Using Semantic Attributes D Vandic, J W van Dam . . . -Decision Support Systems, 2012-Elsevier; Faceted product search powered by the Semantic Web A Watve-2012-cse.msu.edu; Data Transformation For Improved Query Performance EC Dragut, W Meng . . . -Synthesis Lectures on Data . . . , 2012-morganclaypool.com; Deep Web Query Interface Understanding and Integration M Keshavarzi, M A Dehghan . . . -Fuzzy Information and . . . , 2012-Springer; Applications of classification based on similarities and dissimilarities Y Zhang-2012-cs.cmu.edu; Learning with Limited Supervision by Input and Output Coding J Rousu-cs.helsinki.fi; Efficient Range Partitioning in Classification Learning M Berg-lib.tkk.fi; Human Abilities to Perceive, Understand, and Manage Multi-Dimensional Information with Visualizations E Vasileios . . . -2012-ics.forth.gr; A real-time semantics-aware activity recognition system L Boratto-2012-veprints.unica.it; Group recommendation with automatic detection and classification of groups A Van Giessen-2012-repository.tudelft.nl; Dimension Reduction Methods for Classification Gitanjali Swamy, R, Brayton, ISBN:0-591-32212-9, University of California, Berkeley, 1996 Incremental methods for formal verification and logic synthesis".

G. M. Swamy, S. Edwards, R. Brayton, In the Proceedings of the IEEE International Conference on VLSI Design, Hyderabad, January 1998. "Efficient Verification and Synthesis using Design Commonalities".

G. M. Swamy, P. McGeer, R. Brayton, In the Proceedings of the International Workshop on Logic Synthesis, Tahoe Calif., May 1993 "A Fully Implicit Quine-McClusky Procedure using BDDs".

Christophe Jouis; Ismail Biskri; Jean-Gabriel Ganascia; Magali Roux, "Next Generation Search Engines", IGI GlobalPub, Mar. 31, 2012 (ISBN-10: 1-4666-0330-5).

Each of the following is expressly incorporated herein by reference in its entirety, for example, for its disclosure of clustering technology, applications of that technology, and implementations: 20120137182; 20120136860; 20120131701; 20120125178; 20120123279; 20120109778; 20120089341; 20120088981; 20120084251; 20120078927; 20120078906; 20120078858; 20120076372; 20120072124; 20120070452; 20120054133; 20120047098; 20120045119; 20120041955; 20120039541; 20120036096; 20120030185; 20120030165; 20120021710; 20120015841; 20120014560; 20120011135; 20120005238; 20110320396; 20110306354; 20110304619; 20110301860; 20110299765; 20110295773; 20110288890; 20110282877; 20110282828; 20110269479; 20110264432; 20110261049; 20110255748; 20110255747; 20110251081; 20110246483; 20110246409; 20110246200; 20110231414; 20110225158; 20110221767; 20110218990; 20110206246; 20110205399; 20110202540; 20110191353; 20110191283; 20110191076; 20110185234; 20110179019; 20110178965; 20110175905; 20110173189; 20110173173; 20110172501; 20110166949; 20110161205; 20110144914; 20110144480; 20110143650; 20110142318; 20110142287; 20110124525; 20110119108; 20110116690; 20110115787; 20110106801; 20110105350; 20110105340; 20110103613; 20110097001; 20110093492; 20110093482; 20110091083; 20110091074; 20110091073; 20110086349; 20110081066; 20110081056; 20110080490; 20110078144; 20110078143; 20110060717; 20110060716; 20110055192; 20110052076; 20110048731; 20110047172; 20110040192; 20110029657; 20110022599; 20110022354; 20110020779; 20110015869; 20110013840; 20110008805; 20110004578; 20110004415; 20110004115; 20110002194; 20110000028; 20100332475; 20100332474; 20100332425; 20100332242; 20100332210; 20100322525; 20100318492; 20100313157; 20100305930; 20100305868; 20100299128; 20100296748; 20100284915; 20100280987; 20100278425; 20100268512; 20100268476; 20100257092; 20100254614; 20100250527; 20100250477; 20100239147; 20100232718; 20100228731; 20100228625; 20100221722; 20100217763; 20100216660; 20100215903; 20100205213; 20100204061; 20100199186; 20100198864; 20100191722; 20100191532; 20100189333; 20100183555; 20100174985; 20100174983; 20100174982; 20100174980; 20100174979; 20100174978; 20100174977; 20100174976; 20100174732; 20100174492; 20100169025; 20100166339; 20100161590; 20100161232; 20100157340; 20100157089; 20100150453; 20100149917; 20100138894; 20100136553; 20100135597; 20100135582; 20100125594; 20100121638; 20100117978; 20100114929; 20100114928; 20100112234; 20100111396; 20100111370; 20100106713; 20100100515; 20100085358; 20100082614; 20100082367; 20100081661; 20100080439; 20100076981; 20100067745; 20100057534; 20100057399; 20100057391; 20100055678; 20100054278; 20100050260; 20100049431; 20100042563; 20100036647; 20100034422; 20100033182; 20100017487; 20100005105; 20100004923; 20100004898; 20090327185; 20090326383; 20090319526; 20090319454; 20090318815; 20090313294; 20090311786; 20090299990; 20090299822; 20090299705; 20090297048; 20090292802; 20090292695; 20090292694; 20090292482; 20090290778; 20090287689; 20090277322; 20090276705; 20090271694; 20090271424; 20090271405; 20090271404; 20090271397; 20090271363; 20090271359; 20090271246; 20090265024; 20090252046; 20090248399; 20090234876; 20090226081; 20090222430; 20090220488; 20090204609; 20090204574; 20090204333; 20090199099; 20090190798; 20090175545; 20090175544; 20090169065; 20090164192; 20090154795; 20090150340; 20090132347; 20090125916; 20090125482; 20090124512; 20090104605; 20090097728; 20090094265; 20090094233; 20090094232; 20090094231; 20090094209; 20090094208; 20090094207; 20090094021; 20090094020; 20090093717; 20090083211; 20090081645; 20090080777; 20090077093; 20090070346; 20090063537; 20090060042; 20090055257; 20090055147; 20090048841; 20090043714; 20090028441; 20090024555; 20090022472; 20090022374; 20090012766; 20090010495; 20090006378; 20080319973; 20080310005; 20080302657;

20080300875; 20080300797; 20080275671; 20080267471; 20080263088; 20080261820; 20080261516; 20080260247; 20080256093; 20080249414; 20080243839; 20080243817; 20080243816; 20080243815; 20080243638; 20080243637; 20080234977; 20080232687; 20080226151; 20080222225; 20080222075; 20080221876; 20080215510; 20080212899; 20080208855; 20080208828; 20080201397; 20080198231; 20080198160; 20080191035; 20080189306; 20080188964; 20080183546; 20080182282; 20080181479; 20080177640; 20080177538; 20080162541; 20080155335; 20080152231; 20080147655; 20080147591; 20080147441; 20080147440; 20080147438; 20080146334; 20080144943; 20080126464; 20080123940; 20080114800; 20080114756; 20080114710; 20080114564; 20080112684; 20080109288; 20080101705; 20080097820; 20080091423; 20080082426; 20080077570; 20080069437; 20080057590; 20080037872; 20080037536; 20080033658; 20080030836; 20080010605; 20080010273; 20080010272; 20080010262; 20080010045; 20080005137; 20070291958; 20070288465; 20070286489; 20070285575; 20070276723; 20070275108; 20070269804; 20070263900; 20070255707; 20070250522; 20070244768; 20070239982; 20070239741; 20070239694; 20070233711; 20070231921; 20070217676; 20070198553; 20070192063; 20070192034; 20070185946; 20070180980; 20070179784; 20070174335; 20070172803; 20070156516; 20070154931; 20070154066; 20070150443; 20070141527; 20070129991; 20070129011; 20070128573; 20070111316; 20070106405; 20070093966; 20070092905; 20070092888; 20070078846; 20070067212; 20070064627; 20070054266; 20070050708; 20070044010; 20070038612; 20070033533; 20070033521; 20070033515; 20070033292; 20070033221; 20070033214; 20070033170; 20070025637; 20070022279; 20070008905; 20070006177; 20070005556; 20070003138; 20060282425; 20060282298; 20060281473; 20060253258; 20060248141; 20060246495; 20060239338; 20060224356; 20060212337; 20060208185; 20060195415; 20060195269; 20060195204; 20060190465; 20060190191; 20060177837; 20060136589; 20060112146; 20060106816; 20060101377; 20060101060; 20060095521; 20060093208; 20060093188; 20060074924; 20060074771; 20060074621; 20060064177; 20060058592; 20060053142; 20060053129; 20060052943; 20060041414; 20060034545; 20060031219; 20060020662; 20060015630; 20060015341; 20060013482; 20050286774; 20050285937; 20050283328; 20050281291; 20050278324; 20050273319; 20050267993; 20050267992; 20050267991; 20050265331; 20050262044; 20050256413; 20050255458; 20050251882; 20050225678; 20050198575; 20050193216; 20050192768; 20050185848; 20050182570; 20050180638; 20050176057; 20050175244; 20050164273; 20050163384; 20050163373; 20050149269; 20050147303; 20050138056; 20050137806; 20050132069; 20050130230; 20050130215; 20050120105; 20050114331; 20050102305; 20050102272; 20050085436; 20050075995; 20050058336; 20050027829; 20050015376; 20050010571; 20040267774; 20040260694; 20040254901; 20040249939; 20040249789; 20040243362; 20040233987; 20040230586; 20040213461; 20040181527; 20040177069; 20040175700; 20040172225; 20040171063; 20040170318; 20040162834; 20040162647; 20040139067; 20040130546; 20040129199; 20040127777; 20040122797; 20040107205; 20040103377; 20040101198; 20040091933; 20040075656; 20040071368; 20040068332; 20040056778; 20040049517; 20040048264; 20040036716; 20040024773; 20040024758; 20040024739; 20040019574; 20040013292; 20040003005; 20040002973; 20040002954; 20030229635; 20030208488; 20030205124; 20030175720; 20030174179; 20030161500; 20030161396; 20030158842; 20030145014; 20030139851; 20030138978; 20030129660; 20030120630; 20030107768; 20030101003; 20030100996; 20030097357; 20030097356; 20030093227; 20030088563; 20030078509; 20030078494; 20030074251; 20030065661; 20030065635; 20030061249; 20030059081; 20030058339; 20030054573; 20030050923; 20030050908; 20030046253; 20030046018; 20030044062; 20030044053; 20030036093; 20030033138; 20030028564; 20030016250; 20030014191; 20030009469; 20030009333; 20020191034; 20020190198; 20020184080; 20020183966; 20020181786; 20020181711; 20020147703; 20020146175; 20020143989; 20020132479; 20020131641; 20020129038; 20020128781; 20020122587; 20020115070; 20020111966; 20020099721; 20020099675; 20020091655; 20020069218; 20020050990; 20020049740; 20020033835; 20020023061; 20020002555; 20020002550; 20020000986; 20010055019; 20010048753; 20010014868; 20010000356; U.S. Pat. Nos. 8,200,648; 8,200,506; 8,195,734; 8,195,670; 8,195,345; 8,191,783; 8,190,663; 8,190,082; 8,184,913; 8,183,050; 8,180,766; 8,180,627; 8,180,147; 8,175,896; 8,175,730; 8,175,412; 8,170,961; 8,170,306; 8,169,681; 8,169,481; 8,165,407; 8,165,406; 8,164,507; 8,150,169; 8,145,669; 8,139,838; 8,135,719; 8,135,681; 8,135,680; 8,135,679; 8,122,502; 8,122,045; 8,117,213; 8,117,204; 8,117,203; 8,117,139; 8,116,566; 8,108,931; 8,108,405; 8,108,392; 8,099,381; 8,097,469; 8,095,830; 8,095,521; 8,095,389; 8,090,729; 8,082,246; 8,077,984; 8,073,652; 8,065,316; 8,065,248; 8,055,677; 8,051,139; 8,051,082; 8,046,362; 8,041,715; 8,032,476; 8,027,977; 8,019,766; 8,015,183; 8,015,125; 8,015,124; 8,014,957; 8,014,591; 8,010,589; 8,010,466; 8,005,294; 8,000,533; 8,000,527; 7,996,369; 7,991,557; 7,979,435; 7,979,362; 7,975,039; 7,975,035; 7,970,627; 7,966,327; 7,966,225; 7,966,130; 7,962,651; 7,958,096; 7,954,090; 7,953,705; 7,953,679; 7,949,186; 7,937,349; 7,937,234; 7,933,915; 7,933,740; 7,930,189; 7,926,026; 7,917,517; 7,917,306; 7,912,734; 7,912,726; 7,912,290; 7,912,284; 7,904,303; 7,899,564; 7,894,995; 7,894,669; 7,890,512; 7,890,510; 7,890,294; 7,889,914; 7,889,679; 7,885,966; 7,882,126; 7,882,119; 7,879,620; 7,876,947; 7,873,616; 7,868,786; 7,865,456; 7,856,434; 7,849,027; 7,848,567; 7,842,874; 7,835,542; 7,831,549; 7,831,531; 7,831,325; 7,827,183; 7,827,181; 7,826,635; 7,823,055; 7,822,426; 7,813,580; 7,805,496; 7,805,443; 7,805,266; 7,801,893; 7,801,685; 7,783,249; 7,773,784; 7,767,395; 7,761,448; 7,752,208; 7,747,547; 7,747,390; 7,747,054; 7,746,534; 7,743,059; 7,739,284; 7,736,905; 7,716,148; 7,711,846; 7,707,210; 7,702,155; 7,697,785; 7,693,683; 7,689,457; 7,688,495; 7,685,090; 7,684,963; 7,679,617; 7,660,468; 7,657,379; 7,657,126; 7,657,100; 7,650,320; 7,644,090; 7,643,597; 7,639,868; 7,639,714; 7,624,337; 7,613,572; 7,610,306; 7,603,326; 7,599,917; 7,599,799; 7,590,264; 7,584,168; 7,580,682; 7,580,556; 7,574,409; 7,574,069; 7,570,213; 7,567,961; 7,565,432; 7,565,346; 7,565,251; 7,565,213; 7,562,325; 7,562,015; 7,558,425; 7,555,441; 7,552,474; 7,552,131; 7,545,978; 7,539,656; 7,529,732; 7,526,101; 7,519,227; 7,519,209; 7,516,149; 7,512,524; 7,499,916; 7,492,943; 7,487,056; 7,475,085; 7,468,730; 7,464,074; 7,458,050; 7,450,746; 7,450,122; 7,437,308; 7,428,541; 7,428,528; 7,426,301; 7,424,462; 7,418,136; 7,406,200; 7,401,087; 7,397,946; 7,395,250; 7,389,281; 7,386,426; 7,376,752; 7,369,961; 7,369,889; 7,369,680; 7,346,601; 7,337,158; 7,328,363; 7,325,201; 7,296,088; 7,296,011; 7,293,036; 7,287,019; 7,275,018; 7,272,262; 7,263,220; 7,251,648; 7,246,128; 7,246,012; 7,231,074; 7,225,397; 7,222,126; 7,221,794; 7,216,129; 7,215,786; 7,206,778; 7,202,791; 7,196,705; 7,188,055; 7,177,470; 7,174,048; 7,167,578; 7,158,970; 7,142,602; 7,139,739; 7,111,188; 7,068,723; 7,065,587; 7,065,521; 7,062,083; 7,058,650; 7,058,638; 7,054,724; 7,047,252;

7,043,463; 7,039,621; 7,039,446; 7,035,823; 7,035,431; 7,031,980; 7,031,844; 7,016,531; 7,010,520; 6,999,886; 6,993,186; 6,980,984; 6,976,016; 6,970,796; 6,968,342; 6,961,721; 6,954,756; 6,950,752; 6,915,241; 6,912,547; 6,907,380; 6,906,719; 6,904,420; 6,895,267; 6,854,096; 6,845,377; 6,841,403; 6,834,278; 6,834,266; 6,832,162; 6,826,316; 6,819,793; 6,816,848; 6,807,306; 6,804,670; 6,801,859; 6,801,645; 6,799,175; 6,797,526; 6,785,419; 6,785,409; 6,778,981; 6,778,699; 6,763,128; 6,760,701; 6,757,415; 6,751,614; 6,751,363; 6,750,859; 6,735,465; 6,735,336; 6,732,119; 6,711,585; 6,701,026; 6,700,115; 6,684,177; 6,674,905; 6,643,629; 6,636,849; 6,627,464; 6,615,205; 6,594,658; 6,592,627; 6,584,433; 6,564,197; 6,556,983; 6,539,352; 6,535,881; 6,526,389; 6,519,591; 6,505,191; 6,496,834; 6,487,554; 6,473,522; 6,470,094; 6,468,476; 6,466,695; 6,463,433; 6,453,246; 6,445,391; 6,437,796; 6,424,973; 6,424,971; 6,421,612; 6,415,046; 6,411,953; 6,400,831; 6,389,169; 6,373,485; 6,351,712; 6,331,859; 6,300,965; 6,295,514; 6,295,504; 6,295,367; 6,282,538; 6,263,334; 6,263,088; 6,249,241; 6,203,987; 6,192,364; 6,185,314; 6,140,643; 6,122,628; 6,121,969; 6,112,186; 6,100,825; 6,092,049; 6,085,151; 6,049,777; 6,041,311; 5,949,367; 5,940,833; 5,940,529; 5,926,820; 5,920,852; 5,889,523; 5,872,850; 5,813,002; 5,809,490; 5,795,727; 5,764,283; 5,748,780; 5,731,989; 5,724,571; 5,717,915; 5,710,916; 5,699,507; 5,668,897; 5,627,040; 5,625,704; 5,574,837; 5,566,078; 5,506,801; 5,497,486; 5,463,702; 5,448,684; 5,442,792; 5,327,521; 5,285,291; 5,253,307; 5,020,411; 4,965,580; 4,855,923; 4,773,093; 4,257,703; and 4,081,607.

SUMMARY OF THE INVENTION

The Reference-User

The present technology provides a system and method which exploits human interactions with an automated database system to derive insights about the data structures that are difficult, infeasible, or impossible to extract in a fully automated fashion, and to use these insights to accurately assess a risk adjusted value or cluster boundaries.

According to an aspect of the technology, the system monitors or polls a set of users, actively using the system or interacting with the outputs and providing inputs. The inputs may be normal usage, i.e., the user is acting in a goal directed manner, and providing inputs expressly related to the important issues, or explicit feedback, in which the user acts to correct or punish mistakes made by the automated system, and/or reward or reinforce appropriate actions.

Through automated historical and action-outcome analysis, a subset of users, called "reference-users" are identified who demonstrate superior insight into the issue or sub-issue important to the system or its users. After the reference-users are identified, their actions or inputs are then used to modify or influence the data processing, such as to provide values or cluster the data. The adaptive algorithm is also able to demote reference-users to regular users. Additionally, because reference-user status may give rise to an ability to influence markets, some degree of random promotion and demotion is employed, to lessen the incentive to exploit an actual or presumed reference-user status. Indeed, the system may employ a genetic algorithm to continuously select appropriate reference-users, possibly through injection of "spikes" or spurious information, seeking to identify users that are able to identify the spurious data, as an indication of users who intuitively understand the data model and its normal and expected range. Thus, the system is continuously or sporadically doing 3 things—learning from reference-users and learning who is a reference-user, requesting more granulation/tagging and using that learning to cluster/partition the dataset for the ordinary users for the most contextually relevant insight.

Often, the reference-user's insights will be used to prospectively update the analytics, such as the distance function, clustering initial conditions or constraints, or optimization. However, in some cases, the adaptivity to the reference-user will only occur after verification. That is, a reference-user will provide an input which cannot contemporaneously be verified by the automated system. That input is stored, and the correspondence of the reference-user's insight to later reality then permits a model to be derived from that reference-user which is then used prospectively. This imposes a delay in the updating of the system, but also does not reveal the reference-user's decisions immediately for use by others. Thus, in a financial system, a reference-user might wish to withhold his insights from competitors while they are competitively valuable. However, after the immediate value has passed, the algorithm can be updated to benefit all. In an investment system, often a reference-user with superior insight would prefer that others follow, since this increases liquidity in the market, giving greater freedom to the reference-user.

A key issue is that a fully automated database analysis may be defined as an NP problem and in a massive database, the problem becomes essentially infeasible. However, humans tend to be effective pattern recognition engines, and reference-users may be selected that are better than average, and capable of estimating an optimal solution to a complex problem "intuitively", that is, without a formal and exact computation, even if computationally infeasible. As stated above, some humans are better than others at certain problems, and once these better ones are identified, their insights may be exploited to advantage.

In clustering the database, a number of options are available to define the different groups of data. One option is to define persons who have a relationship to the data. That is, instead of seeking to define the context as an objective difference between data, the subjective relationships of users to data may define the clusters. This scenario redefines the problem from determining a cluster definition as a "topic" to determining a cluster definition as an affinity to a person. Note that these clusters will be quite different in their content and relationships, and thus have different application.

Optimal clustering is only one aspect of the use of a reference-user. More generally, the reference-user is a user that demonstrates uncommon insight with respect to an issue. For example, insight may help find clusters of data that tend to gravitate toward or away from each other and form clusters of similarity or boundaries. Clustering is at the heart of human pattern recognition, and involves information abstraction, classification and discrimination.

Thus, according to the present technology, we consider a system having a network of "users", which may be ordinary human users that simply require the computer to synthesize some insight from a large dataset, as well as "reference-users" who help the computer refine and set context in the dataset. While the designation of user and reference-user partitions the space of users. The process of selecting who is a user and who is a reference-user is automated and the designations may not be persistent, i.e., the computer is continually re-evaluating who is a user and who is a reference-user based on how they interact with the system.

From a database user's perspective, a query should be simple, e.g., "natural language", and not require a specific knowledge of the data structures within the database or a complete knowledge of the data structures being searched. In other words, the user should not have to know the structure of database before the query result is obtained. The result should preferably include relevant responses sorted or organized according to relationship with the query. In other cases, the sorting or ranking may be according to different criteria. Much as the clustering problem employs a distance function, the reporting problem also employs a ranking or information presentation prioritization function. Indeed, the outputs may be clustered either according to the clustering of the source database, or the responses to a query may be clustered upon demand.

In some cases, a user wishes only results with high relevance, while in other cases, a user may wish to see a ranked list which extends to low relevance/low yield results. A list, however, is not the only way to organize results, and, in terms of visual outputs, these may be provided as maps (see U.S. Pat. No. 7,113,958 (Three-dimensional display of document set); U.S. Pat. No. 6,584,220 (Three-dimensional display of document set); U.S. Pat. No. 6,484,168 (System for information discovery); U.S. Pat. No. 6,772,170 (System and method for interpreting document contents), each of which is expressly incorporated herein by reference), three or higher dimensional representations, or other organizations and presentations of the data. Thus, the distinction between the query or input processing, to access selected information from a database, and the presentation or output processing, to present the data to a user, is important. In some cases, these two functions are interactive, and for example, a context may be used preferentially during presentation rather than selection.

According to one embodiment of the system and method according to the present technology, a reference-user is employed periodically to normalize a data distribution, based on the reference-user's insights. This normalization acts as a correction to an automated algorithm, and the normalization information received from the reference-user tunes the algorithm, which, for example, represents distance function or partition (clustering) function. In effect the reference-users train the system when they unconsciously partition elements from the cluster based on their instincts.

The system does not have to be continuously trained by the reference-user or act to continuously reselect reference-users. The training is important only when the divergence between what the system reports as insight on a self-similar cluster and what the dominant set of users consider to be an insight, becomes unacceptably large. When this divergence becomes unacceptably large for the remaining users in the network, then the reference-user training is invoked and the system learns from the reference-user. If the divergence corrects, the systems stops retraining and continues as before. However, if the divergence does not, then the system reselects the reference-user and then retrains. Once again if the divergence corrects, the system continues as before. However, if it does not, the system then flags the needs for more data by requesting additional meta-tagging of the content.

Thus, the system is continuously doing 3 things (a) learning from reference-users; (b) learning who is a reference-user; and (c) requesting more granulation and using that learning to cluster/partition the dataset for the ordinary users for the most contextually relevant insight.

Context-Based Reference-Users

Clustering of massive databases poses a number of problems. For example, the computational complexity of some algorithms is sufficiently high that clustering cannot be updated in real time. Further, an inherent challenge in automated clustering comes from realizing that a machine may have no context, or that solution of the clustering problem could be significantly facilitated by determination and exploitation of context information. Thus, superior clustering in various cases requires the establishment of context by some means to facilitate filtering of the clusters by the computer algorithm. Another aspect of this problem is that the bases for the clustering may be determined ad hoc, or the relevant distinctions available with information provided at the time of consideration.

Context can be assumed if the insight required, and dataset to be algorithmically operated on, is small and specialized enough. Unfortunately, in very high dimensionality databases, such as Google's semantic database of the web and related data feeds, the resulting number of clusters may be extraordinarily high, and as a result the clustered database may be of little use without further distinctions being drawn. For example, the Google search engine requires a query, and even then returns result based on multiple undistinguished contexts, leading to a potentially large proportion of irrelevant responses. Likewise, simplifying presumptions made to reduce complexity may eliminate the very distinctions that are required for a particular circumstance.

While computers have computational power for performing standard algorithmic calculations, humans have the ability to immediately judge context. Humans do this contextual mapping by looking for similarity in networks, similarity in knowledge sets and similarity in skills Thus, an automated way of identifying how to elicit that human "secret sauce" around context, will significantly speed up the computers ability to partition the space into proper contextually relevant clusters.

Implicit in natural language searching and "relevance" to a query is the concept of "context". A Boolean text search does not benefit from knowledge of language structures and latent ambiguities, and thus will typically deliver results that are contextually irrelevant but meet the Boolean query criteria. On the other hand, natural language search technologies and other unstructured search systems can benefit from context, though often determining this context requires an inference. Alternately, a user can define a context, for example by limiting himself or herself to a special purpose database or other limitation. A user can also seek to explicitly indicate the context, assuming that the user is aware of the different contexts to be distinguished. However, it is often necessary to query the database before determining the clustering of responsive records, and then obtaining feedback from a user to define the context and therefore focus on respective clusters. However, in some cases the "context" that might be derived from an automated clustering of records defies semantic description, thus requiring a "clustering by example" feedback/training of the system, or other type of non-semantic guidance of the system, and which might incur a much larger effort than most users would voluntarily endure, and perhaps incur more effort and/or higher costs than simply accepting both relevant and irrelevant information in response to the query and distinguishing these manually.

The present technology proposes a solution to this problem by designating "reference-users", that is, either the reference-user has previously indicated or proven a superior ability to operate in a certain context, or otherwise represent the context by consistency and reliability. The user context may be determined in various ways, but in the case of persistent contexts, a user profile may be developed, and a reference-user selected with whom the user has some affinity, i.e., overlapping or correlated characteristics. There are multiple ways to designate the reference-user—the system designates the reference-user based on filtering a set of users to which reference-user best represents the responses and preferences of the set. This designation of reference-user comes from affinity, which could be network-affinity (users that are closely connected in the network in that context), knowledge-affinity (users that have superior expertise in that context), or skill-affinity (users possessing specialized skills in that context).

It is noted that the reference-user is discussed as an actual single human user, but may be a hybrid of multiple users, machine assisted humans, or even paired guides.

The problem of defining the context of a user is then translated to the problem of finding a suitable reference-user or set of reference-users. In fact, the set of reference-users for a given user may have a high consistency, and as known in the field of social networking. That is, assuming that the word "friend" is properly defined, the universe of contexts for a user may be initially estimated by the contexts of interest to his or her identified friends. Such an estimation technology is best exploited in situations where error is tolerable, and where leakage of user-specific contexts is acceptable.

In some cases, the reference-user sought is one with superior insights (rather than exemplary insights), that is, the reference-user is "better" than a normal user, and as such leads the other users. This is appropriate where an economic quality function is available, and the maximization of that function does not require significant compromise. This type of system has a well-defined and generally invariant definition of "best", especially when an economic cost-benefit function can be defined and readily adopted.

In other cases, the reference-user should be the epitome of the class, and thus not quantitatively deviant from the group as a whole. In such a case, the user with the "best" insight might be considered statistically deviant from the mean, and therefore not a good choice for designation as reference-user.

For example, in a scientific literature database, an "expert" in a field may be designated as a reference-user, and the context associated with that expert representing the field of expertise. A database so organized would cluster the documents in the database around different spheres of expertise; the narrower the expertise of the designated expert reference-user, the higher the quality of distinctions which may be drawn from other knowledge domains.

In contrast, a general purpose database such as Google may be used by fifth graders. The clustering of information based on expertise may lead to low ranking of documents appropriate for that type of user, and high ranking of documents which are either incomprehensible to the user, or lacking relevance. Thus, the goal in a general purpose system is to identify reference-users who are similarly situated to the actual user, and therefore whose usage correlates with the intended or supposed use by the user.

Indeed, these two different types of reference-users may both be used in parallel, though because they are not self-consistent as each represent "context", these should be treated as independent or semi-independent factors.

The "expert" reference-user, for example, may be of use to the fifth grader; the reference-user profile can be used to distinguish various contexts at high levels, which can then be used to rank documents at the appropriate level for the user. The epitome reference-user may be useful to the technical user; some relevant documents may be outside the experience or sphere of the expert reference-user, and a more common reference-user may provide useful insights for ranking or segregating those documents. By pairing the expert and the epitome, a comparison of the results may also be of use, especially in ranking the results in terms of degree of specialization.

It may be useful to explicitly receive user profile information, or inferentially derive such information, in order to identify context. In addition to analyzing content associated with user actions, the speed, duration, and latency of user actions may be analyzed, as well as the range of contexts, and usage of content.

As a final note on the form of interaction of the reference user with the data, in the typical case, we assume that the reference user can choose how they filter, cluster and view the data set. Thus, in their "view", a reference user may choose to subtract points they wish to view, or add points they wish to "view". This process does not change the dataset itself, but merely changes the way the reference user chooses to view the dataset. It changes the filter and is merely reflective of their context.

Objects

It is therefore an object to provide a decision support system, comprising a user input port configured to receive user inputs comprising at least one user criterion and at least one user input tuning parameter representing user tradeoff preferences for producing an output from a system which selectively produces an output of tagged data in dependence on the at least one user criterion, the at least one user input tuning parameter, and a distance function; a reference-user input configured to receive at least one reference-user input parameter representing the at least one reference-user's analysis of the tagged data and the corresponding user inputs, to adapt the distance function in accordance with the reference-user inputs as a feedback signal, wherein the reference-user acts to optimize the distance function based on the user inputs and the output, and on at least one reference-user inference; and an information repository configured to store the tagged data.

It is a further object to provide a decision support system, comprising a user input port configured to receive user inputs comprising at least one user criterion and at least one user input tuning parameter representing user tradeoff preferences for producing an output from a system which selectively produces an output of tagged data in dependence on the at least one user criterion, the at least one user input tuning parameter, and a distance function; a reference-user agent configured to receive at least one reference-user input parameter representing the at least one reference-user's analysis of the tagged data and the corresponding user inputs, to adapt the distance function in accordance with the user inputs as a feedback signal, wherein the reference-user agent acts to optimize the distance function based on the user inputs and the output, and on at least one reference-user inference derived from at least one human user selected from a plurality of possible users based on an accuracy of selection according to an objective criterion; and an information repository configured to store the tagged data.

It is a still further object to provide a decision support method, comprising receiving user inputs comprising at least one user criterion, and at least one user input tuning parameter representing user tradeoff preferences for producing an output; selectively producing an output of tagged data from a clustered database in dependence on the at least one user criterion, the at least one user input tuning parameter, and a distance function; receiving at least one reference-user input parameter representing the at least one reference-user's analysis of the tagged data and the corresponding user inputs, to adapt the distance function in accordance with the reference-user inputs as a feedback signal; and clustering the database in dependence on at least the distance function, wherein the reference-user acts to optimize the distance function based on the user inputs and the output, and on at least one reference-user inference.

The clustering may be automatically performed by a processor. The database may receive new data. The distance function may be applied to cluster the database including the new data before the at least one reference-user input parameter is received. The tagged data may comprise a valuation or rating. The distance function may be adaptive to new data. The reference-user inference may represent at least one of a valuation and a validation. The user input tuning parameter may comprise a dimensionless quantitative variable that impacts a plurality of hidden dimensions. The hidden dimensions may comprise at least one of completeness, timeliness, correctness, coverage, and confidence. The user input tuning parameter may balance completeness and correctness of the tagged data in the output.

Another object provides an information access method, comprising receiving a semantic user input comprising an indication of interest in information; determining a context of the user distinctly from the semantic user input comprising an indication of interest in information; producing an output of at least tagged data from a clustered database in dependence on at least the user input, the determined context, and a distance function; monitoring a user interaction with the output; and modifying the distance function in dependence on at least the monitored user interaction.

The method may further comprise selecting at least one commercial advertisement extrinsic to the tagged data from the clustered database for presentation to the user, in dependence on at least: at least one of the semantic user input and the output of tagged data, and the determined context. The selecting may be further dependent on the distance function. The monitoring may comprises monitoring a user interaction with the at least one commercial advertisement, wherein the commercial advertisement is selected in dependence on the distance function, and the distance function is modified based on the user interaction with a selected advertisement. The method may further comprise reclustering the database in dependence on the modified distance function. The method may further comprise classifying a plurality of users, and distinguishing between difference classes of users with respect to the selection and modifying of respective ones of a plurality of distance functions. The method may further comprise determining at least one reference-user from a set of users, based on at least one fitness criterion, and selectively modifying the distance function dependent on a reference-user input in preference to a non-reference-user input. A user input is associated with a respective reference-user in dependence on the context.

Another object provides an information processing method, comprising: clustering a database comprising a plurality of information records according to semantic information contained therein, wherein information may be classified in a plurality of different clusters in dependence on a context, such that a common semantic query to the database yields different outputs over a range of contexts; producing an output identifying information records from the database in dependence on at least a user semantic input, and a distance function; receiving user feedback; and modifying at least one distance function in dependence on the user feedback.

The method may further comprise determining a contextual ambiguity from the user semantic input, soliciting contextual ambiguity resolution information from the user, and producing a followup output identifying information records from the database in dependence on at least a user semantic input, the contextual ambiguity resolution information, and at least one distance function selected from a plurality of available distance functions in dependence on the contextual ambiguity resolution information. The method may further comprise selecting at least one commercial advertisement extrinsic to the information records in the database for presentation to the user, in dependence on at least: the user semantic input, and the contextual ambiguity resolution information. The selecting may be further dependent on at least one distance function. The method may further comprise selecting at least one commercial advertisement extrinsic to the information records in the database for presentation to the user, in dependence on at least: the user semantic input, and the distance function. The monitoring may comprise monitoring a user interaction with at least one commercial advertisement presented to the user as part of the output, wherein the commercial advertisement is selected in dependence on at least one distance function, and the at least one distance function is modified based on the user interaction with at least one selected advertisement. The method may further comprise reclustering the database in dependence on the at least one modified distance function. The method may further comprise classifying a plurality of users, and distinguishing between difference classes of users with respect to the selection and modifying of respective ones of a plurality of distance functions. The method may further comprise assigning a reference-user status to at least one user within a set of users, based on at least one fitness criterion, and selectively weighting a user contribution to a modification of a respective distance function dependent on the reference-user status of the respective user. The reference-user status may be assigned with respect to a context, and a user input is associated with a respective distance function in dependence on the context.

DETAILED DESCRIPTION OF THE PREFERRED EMBODIMENTS

Search Engine

Figure 1:
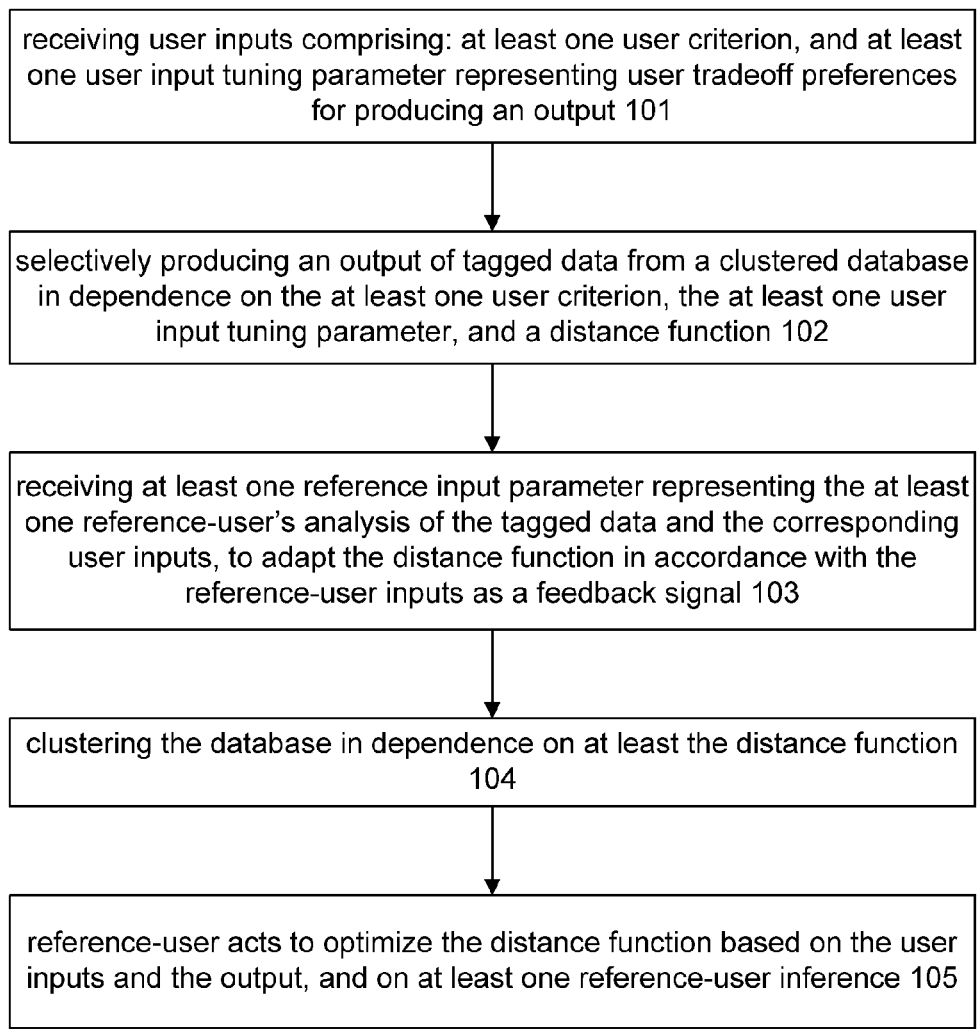
FIG. 1 is a flowchart according to a first embodiment of the technology.

The reference-user is exploited in various ways. In a very uncommon scenario, the reference-user directly and in real time guides a search result. That is, the reference-user acts as expert assistance for the user, a sort of reference librarian. The abilities of the reference-user are directly exploited, but this is expensive, non-scalable, and may have difficulty addressing contexts that transcend a single reference-user, such as a hybrid context.

Another way to exploit a reference-user is to obtain a rich profile of the reference-user based on close monitoring of the reference-user or explicit training by the reference-user of an automated system. In essence, the reference-user's essence is transferred to an artificial agent, which then emulates the reference-user. This technique is both scalable and relatively low cost, but may fail in new circumstances. That is, such systems may do a fair job at interpolation, but may have great difficulty extrapolating. Likewise, generalizations from the reference-user profile may be unhelpful, especially if the generalization transcends the reference-user scope.

A further way to exploit the reference-user is to proactively procure a decision from the reference-user, based on his or her inferences. These decisions may be focused on defining cluster boundaries, which may be tuned, for example, at the distance function, clustering criteria, or optimization level, or imposed as an external constraint by direct classification (or reclassification) of one or more objects. Thus, as part of a voluntary process, reference-users or potential reference-users may be requested to provide feedback, or usage monitored for inferential feedback, to determine classifications (clustering) and a distance function representing quantitatively how much a given item corresponds to the putative classification. The clustering properties thus derived need not be used in a "social" context; that is, a user may be able to identify the context as a cluster, without direct or indirect reference to the reference-user responsible or partially responsible for the clustering. Therefore, a kind of collaborative filter may be implemented, to identify the appropriate reference-user or affinity group, and thereafter exploit the identified reference-user or affinity group in various ways, as may be known, or described herein. In some cases, the distance function may have separate components for a value of proper classification and a cost of misclassification. For example, in a commercial database, the retrieval cost is expensive, so there may be a bias against inclusion of objects where the relevance is doubtful, as compared to objects with equal distance, but more assured relevance.

This may be especially important where the reference-users have multiple roles, or where all roles are not relevant to a context. Thus, in a social relationship system, the reference-user as a whole defines the context (which may significantly overlap for different reference-users), while in a clustered system, all that matters is the definition of cluster boundaries and/or distance function, and the problem of selecting a cluster is different than selecting a high affinity reference-user. However, not all context determination problems are difficult, and therefore other statistical or artificial intelligence technologies may be employed.

In some cases, a pre-result may be provided to a user, which requests user input to select a particular context or contexts. This technique is disfavored in a Google-type search engine, since typically, the user seeks high quality results in the first response, and consistency of search results upon repetition. On the other hand, if a user submits a query, the initial response may be context-free (or multi-context). However, the user may then be given various options for explicit or implicit feedback, such that the ranking of results changes with each new page presented by the search engine. This feedback is a natural way to receive input for defining reference-users and for obtaining inferences from reference-users or potential reference-users. In addition, there is typically insufficient time between submission of an initial search and when the initial response is expected, in order to perform a computationally complex ad hoc clustering or other document analysis. However, the delay between the initial response (first download) from a query and subsequent responses (downloads/page refreshes) may be sufficient to perform complex analytics on the subset of responsive documents. Thus, according to one aspect, a database interface is provided that implements an adaptive user interface based on feedback received. In some cases, the feedback and context definition may be persistent, but in others, the context will be used only for the immediately subsequent interactions.

It is noted that feedback from a reference-user in a Google type search engine may be derived by monitoring click-throughs from the search results. A reference-user would presumably be able to filter useful results from those of limited value. The subset of results selected by the reference-user represents a cluster, which can then be used as an exemplar for updating the clustering algorithm for future searches within the cluster domain for which the reference-user is associated.

Thus, the first response from a database may be without defined context, or even specifically designed to elicit a definition of the context from the user. The second response may benefit from analytics as well as explicit or implicit feedback from the user to define the context and/or cluster identification. In a typical massive database, results and partial results are cached, and analytics may be performed on these cached results to determine clusters of information according to various criteria. Given a user input seeking a database response, the database may initially reveal results representing different clusters that correspond to the query. The user may than select one cluster which includes responses relevant to the context. The cluster selection is then returned to the database system, which can then deliver results appropriate for that context. Note that the clusters initially presented need not directly correspond to the identified context. For example, in a complex semantic query, the cached clusters may represent distinctions made on a subset of the query, or using a fuzzy search algorithm. Once the actual cluster including relevant responses is identified, the query may be re-executed using the formal user request, and the selected relevant responses. Typically, a massive database which provides real time responses does not have sufficient time to perform iterative database processes, while the "conversational" system can exploit user latency to perform complex analytics and recursive processes.

Interactions of Reference-Users

In designating reference-users, it is sometimes useful to also designate anti-reference-users; that is, representatives of a class or context that is undesired, or those who demonstrate poor insights. Taking Google again as an example, much of the Internet includes sex and/or adult themes, frivolous or trivial sites, and the like. However, these various elements are not universally ignored, and therefore in the same way that experts on arcane academic topics can be identified, so can "experts" on Internet spam. By identifying these "experts", a negative affinity may be defined to help avoid undesired clusters or classes of information for a user. Thus, the reference-user does not necessarily trivialize the problem to a single cluster with a universal distance function from a common centroid for all objects. Rather, by providing multiple reference-users, the user's context can be matched with the best reference-user (or hybrid/synthetic reference-user) which results in an optimum of comprehensiveness and relevance for the given context. More generally, the user need not select a single cluster/classification/reference-user as the context, but rather a combination (e.g., linear combination) of various clusters/classifications/reference-users may be employed. As appropriate, negative weights, and required logical combinations (and, or, not, etc.) may be applied. In this way, the reference-user is not necessarily an exclusive group with extraordinary capabilities, though in many cases, those types of reference-users are particularly valued.

This technology therefore has application as a filter against inappropriate content, which may be able to implement fine distinctions between acceptable and unacceptable content. In particular, an automated filter which is not guided by human decisions may have difficulty distinguishing "pornography" from "erotica", while (according to Justice Potter Stewart), a reasonable human can make this distinction intuitively. Thus, at risk of requiring the reference-users to actually behold the pornography in order to classify it, the distinctions may be finely drawn based on the human inference; note that the reference-user is typically monitored during normal activities, and not required to perform any particular activity. This example also raises the social network issue; since pornography is subject to community standards, the reference-user selected for this clustering/classification must be representative of the same community as is relevant to the user, and therefore the same data may be subject to a plurality of clusterings and distance functions. Similar distinctions may be drawn in various contexts—Darwinian evolutionists vs. creationists; conservatives vs. liberals; etc. The context may thus be independent of the database, and for example relevant to an ideology of the user.

Assessments of Users

The present technology also provides education and assessments. That is, a normal user may be educated according to the insights of a reference-user, and the ability of a user to classify similarly to an exemplary reference-user may be assessed. These technologies may of course be integrated with other educational and assessment technologies.

Reference-Users in Asset Analysis

In the system and method according to the present technology, as applied to investment data, a reference-user architecture is useful for determining peer groups among different funds, managers, segments. In this case, the goal is to select a reference-user who has demonstrated exemplary past performance at the task, and thus who likely has better "insight" into the investment quality. The reference-user(s) in this case are selected adaptively based on performance, and thus if a prior reference-user loses reliability, he is demoted. In general, the reference-user is not publicly designated, and has no knowledge that he or she serves as a reference-user, thus avoiding a subjective bias. In some cases, a voting scheme may be employed, to provide a consensus among reference-users. However, assuming that a reference-user does in fact have superior capabilities, the voting or statistical averaging may significantly diminish the advantage of having a reference-user with superior insight; such users may be capable of reacting outside of the statistical norms to great benefit, and therefore this advantage should not be squandered by requiring that the reference-user conform to statistical norms or models. Likewise, care should be employed when excluding outliers, since these may represent valuable opportunity. Whether to permit statistical deviation from the norm, or proceed by consensus, is a design decision in the system.

According to another aspect of the technology, a large data set may be processed to define a reduced data set based on reliability and coverage of the data space. The goal is not to place every available data point of the data set within the data space, but rather to define a filtered data set with maximum reliable coverage. Thus, portions of the data space densely populated with high reliability data generally have a higher threshold for inclusion of new data, while portions with lower reliability or lower density more readily accept new data. In this way, reliable statistical inferences can be efficiently drawn, using feasible analysis. Metrics and algorithms are provided for representing the relative veracity and usefulness of individual instances of information and the providing sources. The veracity of information is measured by the difference, if any, between which it disagrees with an overall "best estimate" calculated based on the preexisting data set. The usefulness of information is measured by the amount by which the instance of information decreases the amount of uncertainty. A reference-user may interact with this dataset to criteria regarding the density, veracity and usefulness criteria, influence data inclusion, and/or to cluster the data within the set. In general, correctness is determined by engineering techniques such as total quality management (TQM) and Truth Seeking (triangulation) principles in continuous monitoring. Data accuracy needs to be measured not only at individual data point level, but also when calculating derivative data points. This technology may be used in an asset database system to permit investment analysis, portfolio analysis, and peer analysis, for example.

Based on this reduced data set, peer groups of multivariate data are automatically determined using criteria relevant for human consideration, that is the data is projected into a low dimensional cognitive space. The reduced data set may be supplemented with an overlay of additional data (that is, similar data which is not in the reduced data set), which can then be subjected to the peer group analysis as well. The system is also appropriate for ad hoc queries, though common queries are pre-cached and thus results are available with low latency. The peer clustering algorithms, and the reduced data set may each be modified adaptively, providing dynamically updated analysis tools. The system preferably supports queries relating to the data and relationships of the data, as well as providing customizable dashboards representing common metrics of interest to the alternative investment community.

In order to automatically synthesize investment rating/grading of objects that represent investments, a distance function or transformation function is generated off the data set. As the data set changes, the distance function evolves such that all points with the same net risk or risk reward profile, map to the same cluster or point in the transformed space. The distance function is adaptive and "user evolvable". This consists of a) a reference-user who trains the distance function b) a general group of users that continuously provide data and feedback on its results. The automated risk report for a particular asset is generated by finding all assets that have a similar net risk, i.e., are the same distance radius distance from the investment risk point. This cluster of points may then be rank ordered according to the return metric. The rating is then the "alpha", or excess return over the average representation of the cluster of similar points.

According to one aspect, a mapping algorithm maps the multivariate discrete, continuous hybrid space representing the various factors that distinguish various risk reward profiles into a univariate normalized space such that it is now possible to apply asset allocation principles.

Intelligent Advertising

The value of an alternative asset (poorly valued because of an inefficient market) is the actually realized value at duration of the final exit for a party, as opposed to price, which is the transaction value attributed at the trade or transaction today. When we use this in the context of digital assets such as domain names, Google rankings, ad placement etc. all of which classify as alternatives because they are traded in an inefficient market, then the price is the price paid by the advertiser. If the search engine makes its advertising placement decision based on the highest advertising price only, over the long term this results in poorer placement of items and attrition of eyeballs, in effect reducing the value of the asset. Thus, understanding the difference between price and value, even directionally is critical. Accordingly, another aspect of the technology is to optimize advertisement placement into a natural result (that is, not influenced by the advertising) by referring to the clustering of the data as well as the context, such that the advertising is appropriate, inoffensive, and likely to increase the overall value of the enterprise, based on both the short term revenues from advertising, and the long term reputation and future cash flows that may be influenced. For example, an inappropriately placed ad will generate advertising revenue, but may disincentivize the advertiser to place ads in the future. An appropriately placed ad, which is contextually appropriate and topically appropriate, is more likely to result in a consumer-advertiser transaction, and thus lead to higher future advertising revenues, even if the present value of the ad is not the highest possible option.

A reference-user in this context may be a user who transacts with an advertiser. By matching users with a reference-user, within the appropriate context, it is more likely that the users will also transact with that advertiser, as compared to users in a different context. The ads may therefore be clustered as artificial insertions into the data universe, and clustered accordingly. When a user's corresponding reference-user(s) and cluster(s) of interest are identified, the advertisements within those clusters may then be considered for delivery to the user.

Location-Context Search

According to an embodiment of the technology, location may be used as a context to define a reference-user, and the reference-user profile is then exploited to produce a system response. Thus, rather than iteratively or implicitly determining a relevant context for a user, a location cue, such as GPS location, Internet service provider (ISP) location, IP mapping, inverse domain name lookup, ZIP code, user demographic profile, or the like. The location may this be the present location or a reference location.

The location context is actually determined by the respective users themselves both for the current and the reference location. A particular user has a particular set of location contexts, e.g. given an ambiguous location such as "School Street", a first user may have the reference location context as "School Street in Providence R.I., USA" where the first user's relative lives versus a second user who may have the reference location context as "School Street in Belmont, Mass., USA" where the second user's child goes to school. Both reference locations are contextually relevant to the particular users, but different between different users.

Based on the context, e.g., location, a data entry or response may be selectively processed. Thus, a New Yorker may use language in a different way than a Londoner. In order to interpret the language, profiles of reference-users with similar location references, i.e., selected based on the context, are analyzed for query response correspondence. For example, the reference-user profiles may be used to perform word translations or equivalencies, rank search results, select types of results, and the like. As an example, the first user's reference location is also more relevant to other users/reference user in the first user's cluster.

Once the meaning of the input is determined with some reliability, the next step is determining a useful output. Note that the context for interpretation of the input may differ from the context for producing a meaningful output; that is, the relevant reference-users need not be the same. For example, the New Yorker in London might seek, through a speech recognition system on a smartphone, a club for entertainment. Upon recognizing both location cues, i.e., the origin of the user (which may be accessible from a telephone number or ID, user profile, cookie, speech accent, etc.) and the current location of the user, a set of reference-users may be selected. These may include other New Yorkers in London who visit clubs. However, the set of reference-users is not so limited. The reference-users may be selected more broadly based on preferences, affinities, chronologies, and the like, and may include both visitors to London and natives. Using location tracking and e-commerce technology, information about what day a respective reference-user went to the club, how long her or she spent, what they ordered, how much they tipped, etc., may all be available information. This type of information may be correlated with the user's past history, inside and out of London. Of course, to the extent that explicit ratings of clubs are available, these may also be exploited, but these explicit ratings tend to display bias and are not statistically normalized or validated. Note that the reliability of explicit ratings may improve dramatically when broken down by context, e.g., the reference-user(s) responsible for the rating. In general, using a large body of available information for prospective reference-users, a cluster analysis is performed which may rank or weight different users with respect to their probative value toward resolving the query. Depending on the system implementation, some aspects of the cluster analysis may be performed in advance, and thus only final stages computer on demand. Thus, the context for generating the system response may be determined, and that context used to determine the cluster in which the user "resides", which then defines the reference-user(s) to be referenced in formulating the response. Alternately, an affinity with a reference user or user(s) is determined, e.g., with a collaborative filter, and that set of reference-users used to determine the context cluster. In either case, the response is then generated based on the context cluster, which is statistically linked to the reference-users associated with that cluster. The favorite clubs for the reference-users are then presented as a response to the query, and may be ranked according to weightings derived from the analysis.

It is noted that systems of the type described are typically subsidized by advertising. Therefore, once the meaning of the query is determined, e.g., the user is looking for a club, a set of ads for clubs, club goers, or the user abstract from his goal directed activity, may be presented. In general, a club would not wish to solicit a patron who would not have fun; the tab and tip will be low, and future referrals absent. Likewise, a targeted ad of this type may be relatively expensive, and thus there would be incentive for advertisers to present ads that will likely yield return on investment. The system itself has as a goal to deliver relevant advertising, since user mistrust in the output will lead to loss of usage and advertising revenues. Given the generally aligned incentives, therefore, the advertisers themselves may be provide useful and rich context information. That is, in contrast to normal users, who will often not spend time training a third party system, advertisers may be willing to spend considerable time defining their preferred customers, and providing useful information for those customers. In cases where there is an incentive to "cheat", that is, game the system to achieve an unnatural result, feedback from actual users and a system-imposed punishment may be effective. Thus, if a user is "pushed" to go to a club they do not enjoy, the user may end up being a bad customer (low tab and tip), and may help redefine the cluster so that user for which he or she becomes a reference-user have reduced likelihood of becoming patrons. Since the system may be quite interactive and ubiquitous, feedback may be in nearly real-time. Of course, permitting advertisers to feed the system with information is merely optional, and therefore to the extent that some users seek to taint the system, the cluster analysis and context sensitivity may exclude other users from adverse impact.

Advertisers can target the most contextually relevant reference and current location to push particular content to a respective user.

Recommendation Engine

In another embodiment, a user seeks a recommendation from a recommendation engine. The recommendation engine contains identifications and profiles of users who have posted recommendations/ratings, as well as profiles for users and usage feedback for the system. A user seeking to use the engine is presented (at some time) with a set of questions or the system otherwise obtains data inputs defining the characteristics of the user. In this case, the user characteristics generally define the context which is used to interpret or modify the basic goal of the user, and therefore the reference-user(s) for the user, though the user may also define or modify the context at the time of use. Thus, for example, a user seeks to buy a point-and-shoot camera as a gift for a friend. In this case, there are at least four different contexts to be considered: the gift, the gift giver, the gift receiver, and the gifting occasion. The likelihood of finding a single reference-user appropriate for each of these contexts is low, so a synthetic reference-user may be created, i.e., information from multiple users and gifts processed and exploited. The issues for consideration are; what kinds of cameras have people similarly situated to the gift giver (the user, in this case) had good experiences giving? For the recipient, what kinds of cameras do similar recipients like to receive? Based on the occasion, some givers and recipients may be filtered. Price may or may not be considered an independent context, or a modifier to the other contexts. The various considerations are used in a cluster analysis, in which recommendations relevant to the contexts may be presented, with a ranking according to the distance function from the "cluster definition". As discussed above, once the clustering is determined, advertisements may be selected as appropriate for the cluster, to provide a subsidy for operation of the system, and also to provide relevant information for the user about available products.

Once again, the context is specific to the particular user and thus the right kind of camera for a first user to give a friend is not the same as the right kind of camera for a second user to give to a different friend; indeed, even if the friend is the same, the "right" kind of camera may differ between the two users. For example if the first user is wealthier or other context differences.

Embodiments

Figure 2:
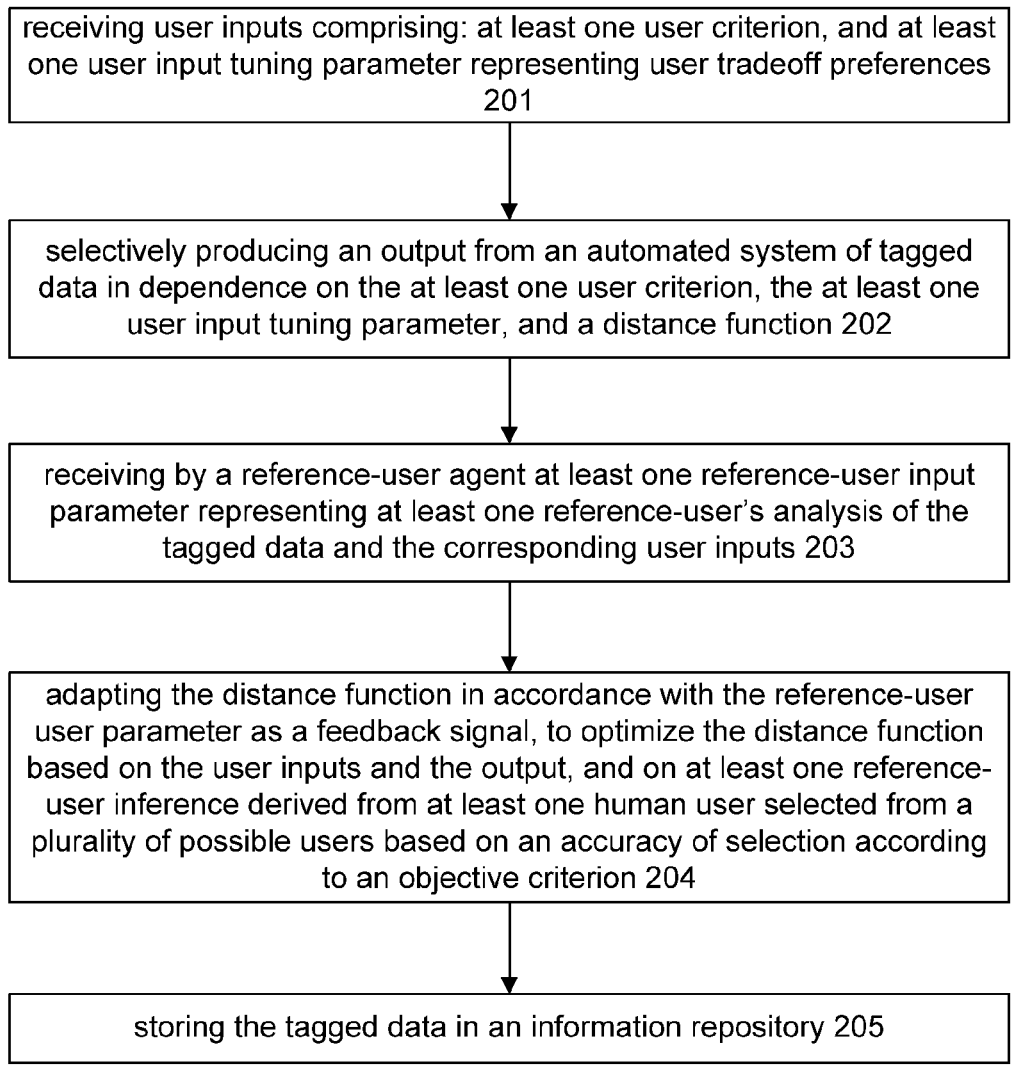
FIG. 2 is a flowchart according to a second embodiment of the technology.

One embodiment provides a decision support system, corresponding to the method shown in FIG. 2. A user input port receives user inputs, which define a user criterion or criteria, and also at least one user input tuning parameter. This parameter represents user tradeoff preferences for producing an output from a system 201. The output is may be in the form of tagged data, selected in dependence on the at least one user criterion, the at least one user input tuning parameter, and a distance function 202. A reference-user input is also provided which receives one or more reference-user input parameters representing a respective reference-user's analysis of the tagged data and the corresponding user inputs 203. The reference-user input is used to adapt the distance function in accordance, using the reference-user inputs as a feedback signal. The reference-user thus acts to optimize the distance function based on the user inputs and the output, and on at least one reference-user inference. This inference may be derived from at least one human user selected from a plurality of users based on an accuracy of selection according to an objective criterion 204. An information repository 205, such as a structured query language database, or so-called "NoSQL" database, configured to store the tagged data.

Another embodiment provides a decision support system, also generally corresponding to the method shown in FIG. 2, having a user input port configured to receive user inputs including at least one user criterion and at least one user input tuning parameter representing user tradeoff preferences 201. The user inputs are used to produce an output of tagged data in dependence on the at least one user criterion, the at least one user input tuning parameter, and a distance function 202. A reference-user agent is provided, which is configured to receive at least one reference-user input parameter representing the at least one reference-user's analysis of the tagged data and the corresponding user inputs 203. The reference-user agent selectively adapts the distance function in accordance with the user inputs as a feedback signal. That is, the user inputs are not necessarily directly used to provide feedback, but rather are filtered through the reference-user agent. The reference-user agent acts to optimize the distance function based on the user inputs and the output, and on at least one reference-user inference derived from at least one human user selected from a plurality of possible users based on an accuracy of selection according to an objective criterion 204. An information repository is provided, configured to store the tagged data 205.

A further embodiment provides a decision support method represented in FIG. 1, comprising receiving user inputs comprising at least one user criterion, and at least one user input tuning parameter representing user tradeoff preferences for producing an output 101; selectively producing an output of tagged data from a clustered database with dependence on at least one user criterion, the at least one user input tuning parameter, and a distance function 102; receiving at least one reference-user input parameter representing the at least one reference-user's analysis of the tagged data and the corresponding user inputs, to adapt the distance function in accordance with the reference-user inputs as a feedback signal 103; and clustering the database in dependence on at least the distance function 104, wherein the reference-user acts to optimize the distance function based on the user inputs and the output, and on at least one reference-user inference 105. The clustering may be automatically performed by a processor. The database may receive new data. The distance function may be applied to cluster the database including the new data before the at least one reference-user input parameter is received. The tagged data may comprise a valuation or rating. The distance function may be adaptive to new data. The reference-user inference may represent at least one of a valuation and a validation. The user input tuning parameter may comprise a dimensionless quantitative variable that impacts a plurality of hidden dimensions. The hidden dimensions may comprise at least one of completeness, timeliness, correctness, coverage, and confidence. The user input tuning parameter may balance completeness and correctness of the tagged data in the output.

Figure 3:
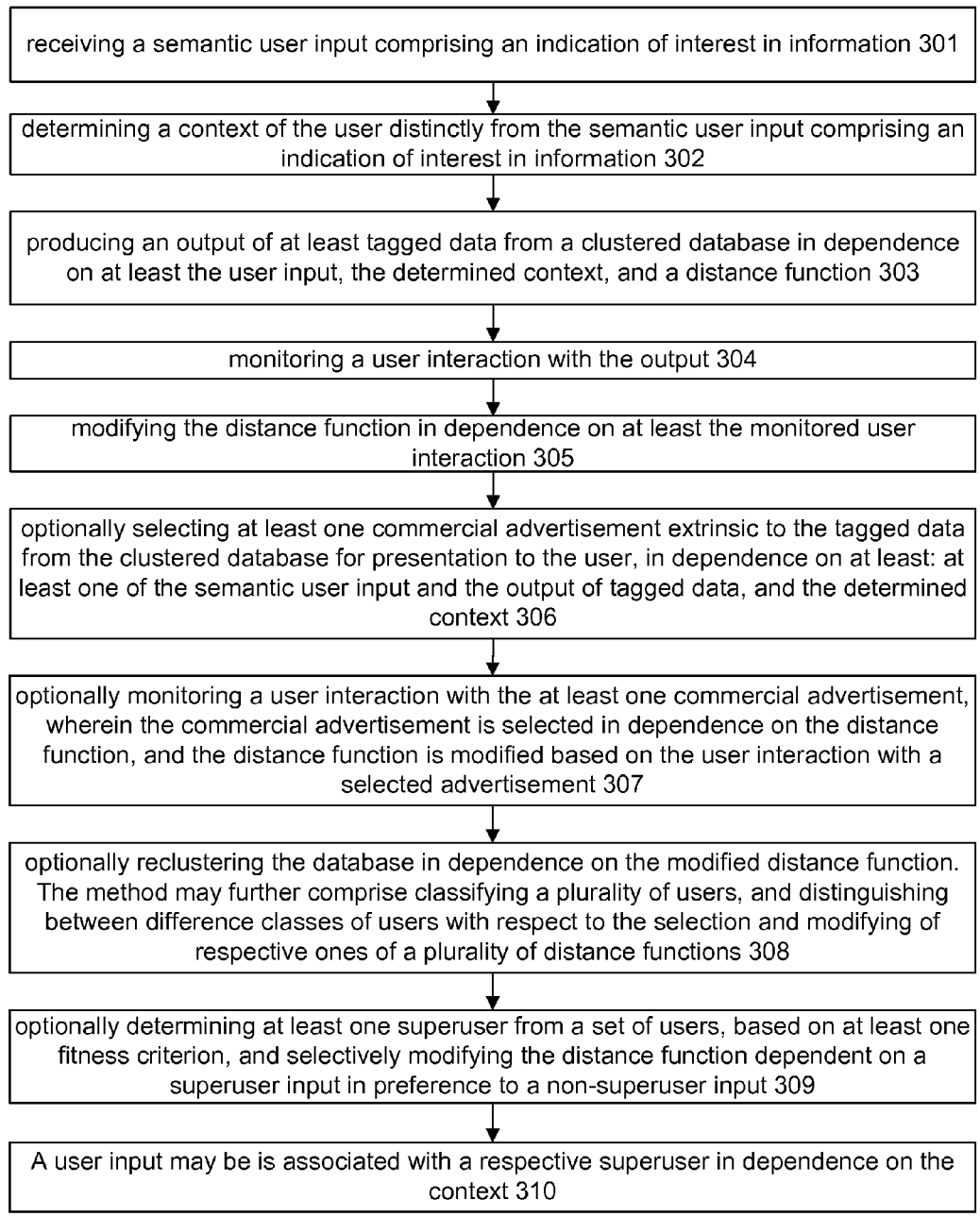
FIG. 3 is a flowchart according to a third embodiment of the technology.
Figure 4:
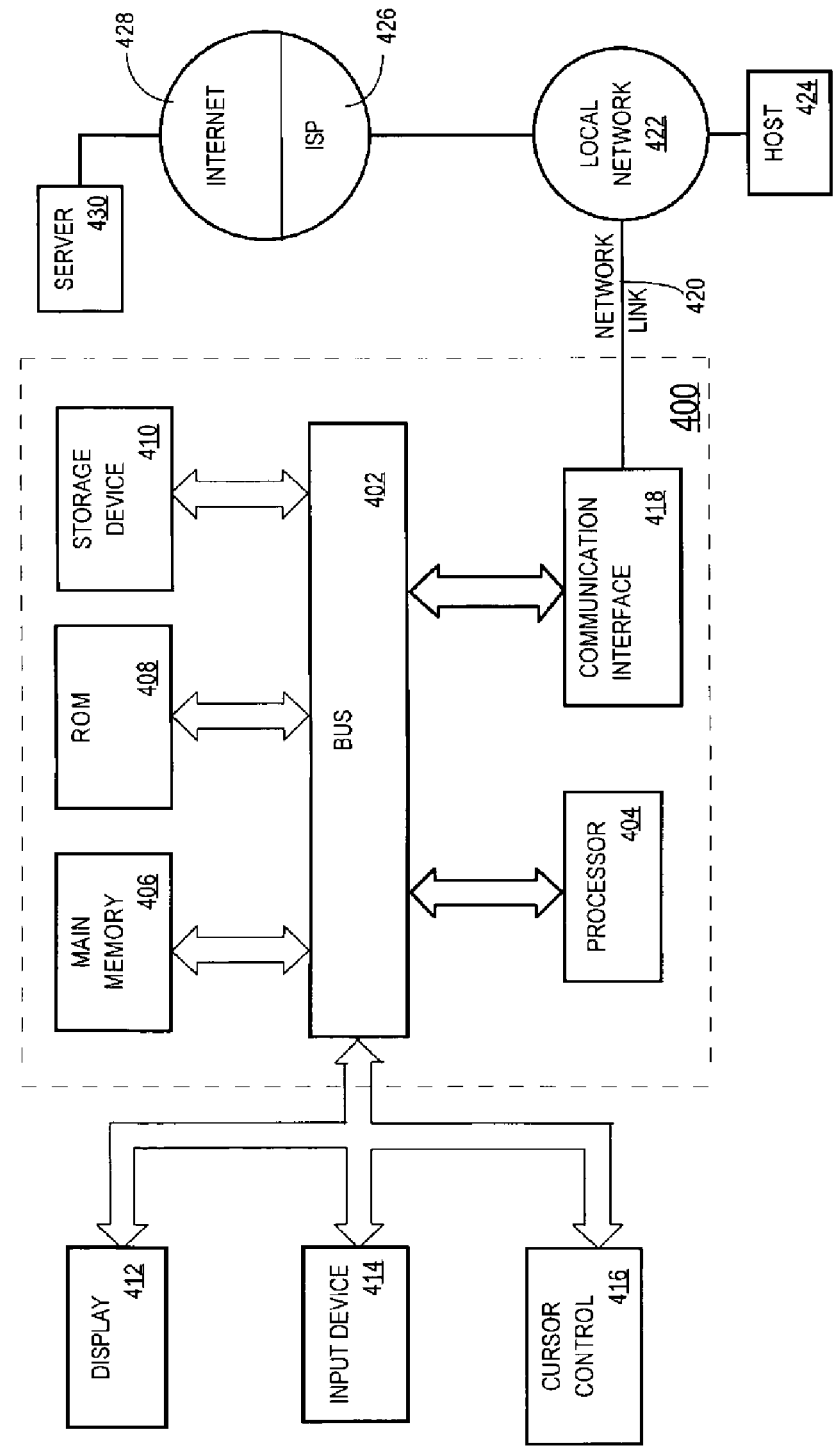
FIG. 4 is a block diagram of a traditional computing system architecture.

Another embodiment provides an information access method, as shown in FIG. 3, comprising receiving a semantic user input comprising an indication of interest in information 301; determining a context of the user distinctly from the semantic user input comprising an indication of interest in information 302; producing an output of at least tagged data from a clustered database in dependence on at least the user input, the determined context, and a distance function 303; monitoring a user interaction with the output 304; and modifying the distance function in dependence on at least the monitored user interaction 305. The method may further comprise selecting at least one commercial advertisement extrinsic to the tagged data from the clustered database for presentation to the user, in dependence on at least: at least one of the semantic user input and the output of tagged data, and the determined context 306. The selecting may be further dependent on the distance function. The monitoring may comprises monitoring a user interaction with the at least one commercial advertisement, wherein the commercial advertisement is selected in dependence on the distance function, and the distance function is modified based on the user interaction with a selected advertisement 307. The method may further comprise reclustering the database in dependence on the modified distance function. The method may further comprise classifying a plurality of users, and distinguishing between difference classes of users with respect to the selection and modifying of respective ones of a plurality of distance functions 308. The method may further comprise determining at least one reference-user from a set of users, based on at least one fitness criterion, and selectively modifying the distance function dependent on a reference-user input in preference to a non-reference-user input 309. A user input is associated with a respective reference-user in dependence on the context 310.

Figure 5:
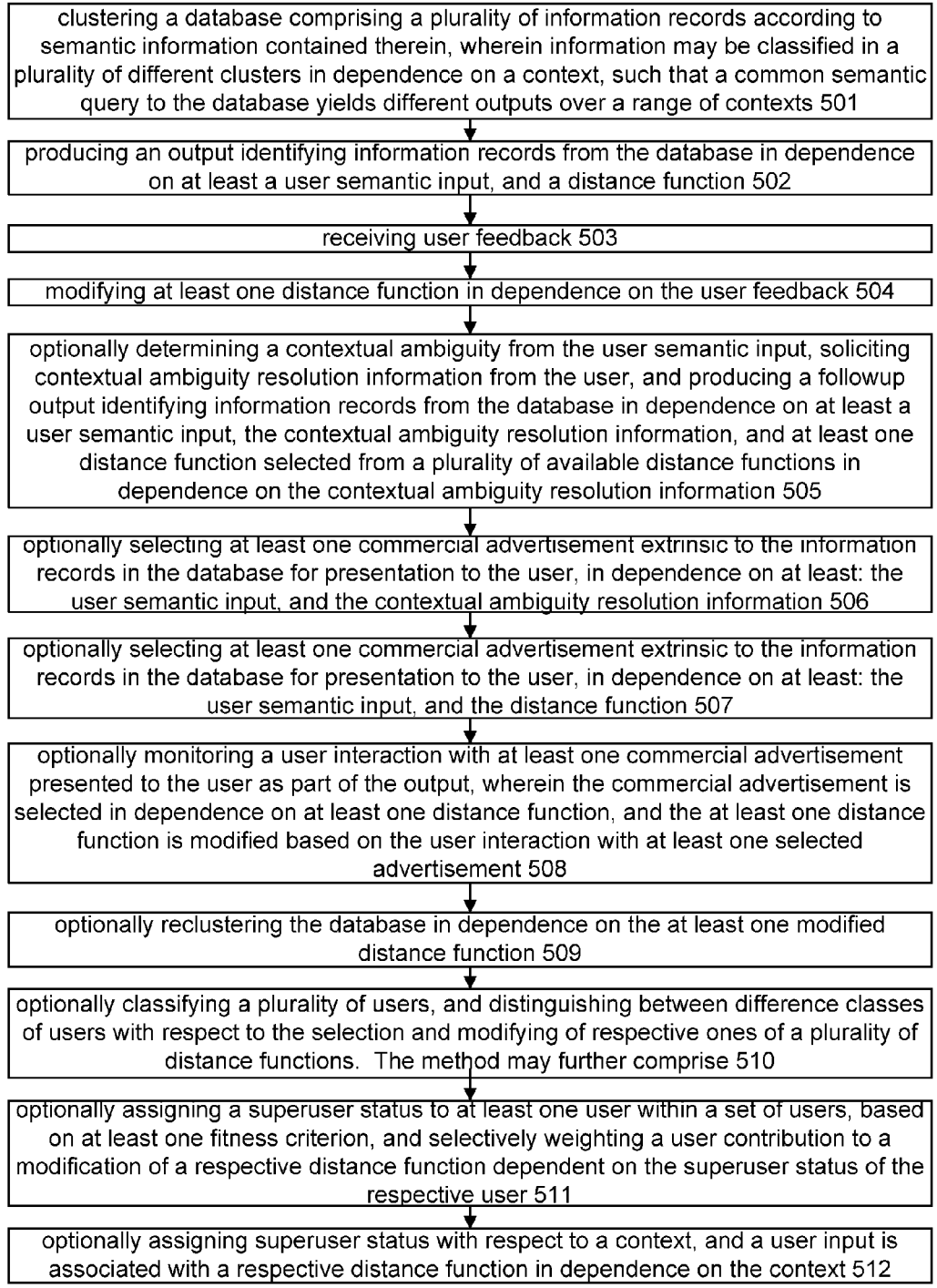
FIG. 5 is a flowchart according to a fourth embodiment of the technology.

Another embodiment provides an information processing method, as shown in FIG. 5, comprising: clustering a database comprising a plurality of information records according to semantic information contained therein, wherein information may be classified in a plurality of different clusters in dependence on a context, such that a common semantic query to the database yields different outputs over a range of contexts 501; producing an output identifying information records from the database in dependence on at least a user semantic input, and a distance function 502; receiving user feedback 503; and modifying at least one distance function in dependence on the user feedback 504. The method may further comprise determining a contextual ambiguity from the user semantic input, soliciting contextual ambiguity resolution information from the user, and producing a followup output identifying information records from the database in dependence on at least a user semantic input, the contextual ambiguity resolution information, and at least one distance function selected from a plurality of available distance functions in dependence on the contextual ambiguity resolution information 505. The method may further comprise selecting at least one commercial advertisement extrinsic to the information records in the database for presentation to the user, in dependence on at least: the user semantic input, and the contextual ambiguity resolution information 506. The selecting may be further dependent on at least one distance function. The method may further comprise selecting at least one commercial advertisement extrinsic to the information records in the database for presentation to the user, in dependence on at least: the user semantic input, and the distance function 507. The monitoring may comprise monitoring a user interaction with at least one commercial advertisement presented to the user as part of the output, wherein the commercial advertisement is selected in dependence on at least one distance function, and the at least one distance function is modified based on the user interaction with at least one selected advertisement 508. The method may further comprise reclustering the database in dependence on the at least one modified distance function 509. The method may further comprise classifying a plurality of users, and distinguishing between difference classes of users with respect to the selection and modifying of respective ones of a plurality of distance functions 510. The method may further comprise assigning a reference-user status to at least one user within a set of users, based on at least one fitness criterion, and selectively weighting a user contribution to a modification of a respective distance function dependent on the reference-user status of the respective user 511. The reference-user status may be assigned with respect to a context, and a user input is associated with a respective distance function in dependence on the context 512.

Hardware Overview

Figure (see U.S. Pat. No. 7,702,660, issued to Chan, expressly incorporated herein by reference), shows a block diagram that illustrates a computer system 400 upon which an embodiment of the invention may be implemented. Computer system 400 includes a bus 402 or other communication mechanism for communicating information, and a processor 404 coupled with bus 402 for processing information. Computer system 400 also include a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Computer system 400 further may also include a read only memory (ROM) 408 or other static storage device coupled to bus 402 for storing static information and instructions for processor 404. A storage device 410, such as a magnetic disk or optical disk, is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

The invention is related to the use of computer system 400 for implementing the techniques described herein. According to one embodiment of the invention, those techniques are performed by computer system 400 in response to processor 404 executing one or more sequences of one or more instructions contained in main memory 406. Such instructions may be read into main memory 406 from another machine-readable medium, such as storage device 410. Execution of the sequences of instructions contained in main memory 406 causes processor 404 to perform the process steps described herein. In alternative embodiments, hard-wired circuitry may be used in place of or in combination with software instructions to implement the invention. Thus, embodiments of the invention are not limited to any specific combination of hardware circuitry and software.

The term "machine-readable medium" as used herein refers to any medium that participates in providing data that causes a machine to operation in a specific fashion. In an embodiment implemented using computer system 400, various machine-readable media are involved, for example, in providing instructions to processor 404 for execution. Such a medium may take many forms, including but not limited to, non-volatile media, volatile media, and transmission media. Non-volatile media includes, for example, optical or magnetic disks, such as storage device 410. Volatile media includes dynamic memory, such as main memory 406. Transmission media includes coaxial cables, copper wire and fiber optics, including the wires that comprise bus 402. Transmission media can also take the form of acoustic or light waves, such as those generated during radio-wave and infra-red data communications. All such media must be tangible to enable the instructions carried by the media to be detected by a physical mechanism that reads the instructions into a machine. Non-transitory information is stored as instructions or control information.

Common forms of machine-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of machine-readable media may be involved in carrying one or more sequences of one or more instructions to processor 404 for execution. For example, the instructions may initially be carried on a magnetic disk of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are exemplary forms of carrier waves transporting the information.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

In this description, several preferred embodiments were discussed. Persons skilled in the art will, undoubtedly, have other ideas as to how the systems and methods described herein may be used. It is understood that this broad invention is not limited to the embodiments discussed herein. Rather, the invention is limited only by the following claims.

The invention may be used as a method, system or apparatus, as programming codes for performing the stated functions and their equivalents on programmable machines, and the like. The aspects of the invention are intended to be separable, and may be implemented in combination, subcombination, and with various permutations of embodiments. Therefore, the various disclosure herein, including that which is represented by acknowledged prior art, may be combined, subcombined and permuted in accordance with the teachings hereof, without departing from the spirit and scope of the invention.

The invention claimed is:

1. A decision support system, comprising:
   a user input port configured to receive user inputs from a first user comprising at least one user selection criterion and at least one user input tuning parameter representing user tradeoff preferences for defining an output of tagged data within a tagged data set from a database;
   a reference-user input configured to receive at least one reference-user input parameter from an identified at least one reference-user different from the first user, representing at least the at least one reference-user's classification inference based on analysis of the tagged data and the corresponding at least one user selection criterion, wherein the user and the at least one reference-user each being human;
   at least one hardware processor configured to:
      cluster the tagged data set from the database according to a distance function representing a quantitative correspondence of a tagged datum to a putative classification;
      selectively produce an output of the tagged data from the database in dependence on at least the at least one user criterion, the at least one reference-user input tuning parameter, and the distance function;
      identify the at least one reference-user from a plurality of possible reference-users based on at least prior quality of classification of data which clusters together with the tagged data by each respective possible reference-user;
      adapt the distance function in accordance with the reference-user input tuning parameter from the identified at least one reference-user as a feedback signal, wherein the reference-user acts to optimize the distance function based on the user inputs and the output, and on the at least one reference-user's classification inference;
      receive new data into the database; and
      re-cluster the database comprising the new data before another at least one reference-user input tuning parameter is received, in dependence on at least the adapted distance function; and
   an information repository configured to replace the distance function with the optimized distance function.

2. A decision support method utilizing at least one computing device, the method comprising:
   receiving user inputs from a user, comprising:
      at least one user criterion, and
      at least one user input tuning parameter representing user tradeoff preferences for producing an output;
   selectively producing the output of tagged data from a database clustered according to classifications, the output being generated by at least one automated processor in dependence on the at least one user criterion, the at least one user input tuning parameter, and a distance function representing a quantitative correspondence of a tagged datum to a putative classification;
   selecting at least one reference-user from a plurality of possible reference-users based on at least prior quality of classification of data which clusters together with the tagged data by each respective possible reference-user, the user and the plurality of possible reference-users each being human and distinct from each other;

receiving at least one reference-user input parameter, from the selected at least one reference-user distinct from the user, representing the selected at least one reference-user's classification inference based on analysis of the tagged data and the corresponding user inputs, to adapt the distance function in accordance with the reference-user inputs as a feedback signal;

receiving new data into the database; and re-clustering the database comprising the new data before another at least one reference-user input parameter is received, in dependence on at least the adapted distance function with the at least one automated processor, wherein the reference-user acts to optimize the distance function based on the user inputs and the output, and on the at least one reference-user's classification inference.

3. The method according to claim 2, wherein the at least one reference-user's classification inference causes the re-clustering to distribute members of a cluster of the database into a plurality of different clusters.

4. The method according to claim 2, wherein the tagged data comprises a valuation or rating.

5. The method according to claim 4, wherein at least the distance function is further adapted based on the received new data after at least one reference-user input parameter is received.

6. The method according to claim 2, wherein the reference-user's classification inference represents at least one of a valuation and a validation.

7. The method according to claim 2, wherein the user input tuning parameter comprises a quantitative variable that impacts a plurality of dimensions hidden by the clustering of the database.

8. The method according to claim 7, wherein the hidden dimensions comprise at least one of completeness, timeliness, correctness, coverage, and confidence.

9. The method according to claim 2, wherein the user input tuning parameter balances completeness and correctness of the tagged data in the output.

10. A decision support system, comprising:

a user input port configured to receive user inputs from a user comprising at least one user criterion and at least one user input tuning parameter representing user tradeoff preferences for producing an output from a system which selectively produces an output of tagged data from a tagged data set within a multidimensional data space comprising a database, in dependence on the at least one user criterion, the at least one user input tuning parameter, and a distance function representing a quantitative measurement of a distance relationship of respective locations within the multidimensional data space;

at least one hardware processor configured to select at least one reference-user from a plurality of possible reference-users based on at least an accuracy of at least one prior reference-user input parameter according to an objective criterion, the user and the plurality of possible reference-users each being human and distinct from each other;

an automated reference-user agent comprising at least one hardware processor, configured:

to receive at least one reference-user input parameter representing the selected at least one reference-user's inference based on an analysis of the tagged data and the corresponding user inputs comprising the at least one user criterion and the at least one user input tuning parameter representing the user tradeoff preferences; and to optimize the distance function in accordance with the at least:

the reference-user input parameter as a feedback signal;

the user inputs comprising the at least one user criterion and the at least one user input tuning parameter representing the user tradeoff preferences; and the output of tagged data;

to cluster the database according to the optimized distance function;

to receive new data into the database; and to re-cluster the database comprising the new data before another at least one reference-user input parameter is received, in dependence on at least the optimized distance function; and an information repository configured to store the output of tagged data.

11. A decision support method utilizing at least a computing device, the method comprising:

receiving user inputs from a user, comprising:

at least one user criterion, and at least one user input tuning parameter representing user tradeoff preferences;

selectively producing an output from an automated system of tagged data in dependence on the at least one user criterion, the at least one user input tuning parameter, and a distance function, the distance function representing a quantitative metric of a correspondence of a tagged datum to a putative classification;

automatically selecting at least one human user from a plurality of possible users based on at least an accuracy according to an objective criterion of prior classification of at least one tagged datum, the selected at least one human user being at least one reference-user and distinct from the user;

receiving by an automated reference-user agent at least one reference-user input parameter representing the at least one reference-user's inference derived from at least analysis of the tagged data and the corresponding user inputs;

adapting the distance function in accordance with the at least one reference-user input parameter as a feedback signal, to optimize the distance function based on at least the user inputs and the output, and the at least one reference-user input parameter, wherein the reference-user acts to optimize the distance function based on the user inputs and the output, and on the at least one reference-user's inference;

clustering the tagged data according to the adapted distance function;

receiving new data into the database after the clustering; and re-clustering the database comprising the new data before another at least one reference-user input parameter is received, in dependence on at least the adapted distance function; and storing the clustered tagged data in an information repository.

12. An information access method utilizing at least one computing device, the method comprising:

receiving a semantic user input comprising an explicit semantic indication of interest in information from a human user;

determining a context of the user distinctly from the semantic user input comprising an implicit indication of interest in information;

automatically clustering a database in dependence on a range of context-dependent distance functions, wherein a plurality of distance functions are provided for the same database, each respective context-dependent distance function representing a quantitative correspondence of a respective tagged datum to a putative cluster classification subject to a respective context corresponding to a respective cluster;

producing an output of at least a portion of the tagged data from a database, in dependence on at least the semantic user input, the determined context, and a context-appropriate distance function;

monitoring a user interaction with the output by the user;

classifying a plurality of users including the user;

modifying the plurality of distance functions in dependence on at least the monitored user interaction; and distinguishing between different classes of users with respect to the selection and modifying of respective ones of the plurality of distance functions;

reclassifying the at least portion of the tagged data into different clusters based on the plurality of modified distance functions and the different classes of users.

13. The method according to claim 12, further comprising selecting at least one commercial advertisement extrinsic to the tagged data from the clustered database for presentation to the user, in dependence on at least: at least one of the semantic user input and the output of tagged data, and the determined context.

14. The method according to claim 13, wherein the selecting the at least one commercial advertisement is further dependent on the modified distance function.

15. The method according to claim 14, wherein the monitoring comprises monitoring the user interaction with the at least one commercial advertisement, wherein the commercial advertisement is selected in dependence on the modified distance function, and the distance function is modified based on the user interaction with a selected advertisement.

16. The method according to claim 12, further comprising re-clustering the database in dependence on the plurality of modified distance functions.

17. The method according to claim 12, further comprising determining at least one reference-user from a set of users distinct from the user, based on at least one objective fitness criterion, and selectively modifying the distance function dependent on a reference-user input in preference to a non-reference-user input.

18. The method according to claim 17, wherein a user-reference input is associated with a respective reference-user in dependence on the determined context of the user.

19. An information processing method utilizing at least one computing device, wherein the method comprising:

clustering a database comprising a plurality of information records according to semantic information contained therein and a plurality of context-dependent distance functions, wherein the same information record within the database is classified in a plurality of different clusters in dependence on a respective context-dependent distance function corresponding to a respective cluster, wherein a common semantic query to the database yields different outputs over a range of contexts;

receiving at least a user semantic input from a user;

determining a contextual ambiguity from the at least user semantic input;

soliciting resolution information to the contextual ambiguity from the user;

producing an output identifying information records from the database in dependence on the at least user semantic input, and a determined context with an associated context-dependent distance function;

receiving user feedback on the output;

modifying the associated context-dependent distance function in dependence on the user feedback and the determined context; and producing a follow-up output identifying information records from the database in dependence on at least the at least user semantic input, the resolution information, and at least one context-dependent distance function selected from the plurality of context-dependent distance functions in dependence on the resolution information.

20. The method according to claim 19, further comprising selecting at least one commercial advertisement extrinsic to the information records identified by the follow-up output in the database for presentation to the user, in dependence on at least: the at least user semantic input, and the resolution information.

21. The method according to claim 20, wherein the selecting the at least one commercial advertisement is further dependent on the determined context and the selected at least one context-dependent distance function.

22. The method according to claim 20, wherein the selecting the at least one commercial advertisement is dependent on at least: the at least user semantic input, the resolution information, the determined context, and an appropriate context-dependent distance function.

23. The method according to claim 19, wherein the monitoring comprises monitoring a user interaction with at least one commercial advertisement presented to the user as part of the output, wherein the commercial advertisement is selected in dependence on the determined context and at least one context-dependent distance function, and the at least one context-dependent distance function is modified based on the user interaction with at least one selected advertisement.

24. The method according to claim 19, further comprising re-clustering the database in dependence on the at least one modified context-dependent distance function.

25. The method according to claim 19, further comprising classifying a plurality of users, and distinguishing between different classifications of users with respect to the selection and modifying of respective ones of a plurality of context-dependent distance functions.

26. The method according to claim 19, further comprising assigning a reference-user status to at least one user within a set of users, based on at least one fitness criterion, and selectively weighting a user contribution to a modification of a respective context-dependent distance function dependent on at least the reference-user status of the respective user.

27. The method according to claim 26, wherein the reference-user status is assigned with respect to a context, and a user input of the respective reference-user is associated with a respective context-dependent distance function in dependence on the context.

* * * * *